(12) United States Patent
Bennett et al.

(10) Patent No.: US 11,807,857 B2
(45) Date of Patent: Nov. 7, 2023

(54) METHODS AND COMPOSITIONS FOR DELIVERING NUCLEIC ACIDS TO PLANT CELLS AND REGULATING GENE EXPRESSION

(71) Applicant: Monsanto Technology LLC, St. Louis, MO (US)

(72) Inventors: Michael Bennett, San Francisco, CA (US); Bill L. Hendrix, West Sacramento, CA (US); Alberto Iandolino, Davis, CA (US); Yao Luo, Davis, CA (US); Wei Zheng, Davis, CA (US)

(73) Assignee: Monsanto Technology LLC, St. Louis, MO (US)

(*) Notice: Subject to any disclaimer, the term of this patent is extended or adjusted under 35 U.S.C. 154(b) by 0 days.

(21) Appl. No.: 15/321,969

(22) PCT Filed: Jun. 24, 2015

(86) PCT No.: PCT/US2015/037522
§ 371 (c)(1),
(2) Date: Dec. 23, 2016

(87) PCT Pub. No.: WO2015/200539
PCT Pub. Date: Dec. 30, 2015

(65) Prior Publication Data
US 2017/0130237 A1     May 11, 2017

Related U.S. Application Data

(60) Provisional application No. 62/072,888, filed on Oct. 30, 2014, provisional application No. 62/017,196, filed on Jun. 25, 2014.

(51) Int. Cl.
C12N 15/82     (2006.01)

(52) U.S. Cl.
CPC ..... *C12N 15/8206* (2013.01); *C12N 15/8218* (2013.01); *C12N 15/8274* (2013.01); *C12N 15/8281* (2013.01); *C12N 15/8282* (2013.01); *C12N 15/8283* (2013.01); *C12N 15/8285* (2013.01); *C12N 15/8286* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. | |
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,901,654 A | 8/1975 | Gross | |
| 3,935,074 A | 1/1976 | Rubenstein et al. | |
| 3,984,533 A | 10/1976 | Uzgiris | |
| 3,996,345 A | 12/1976 | Ullman et al. | |
| 4,034,074 A | 7/1977 | Miles | |
| 4,098,876 A | 7/1978 | Piasio et al. | |
| 4,469,863 A | 9/1984 | Ts'o et al. | |
| 4,476,301 A | 10/1984 | Imbach et al. | |
| 4,535,060 A | 8/1985 | Comai | |
| 4,581,847 A | 4/1986 | Hibberd et al. | |
| 4,666,828 A | 5/1987 | Gusella | |
| 4,683,202 A | 7/1987 | Mullis | |
| 4,761,373 A | 8/1988 | Anderson et al. | |
| 4,769,061 A | 9/1988 | Comai | |
| 4,801,531 A | 1/1989 | Frossard | |
| 4,810,648 A | 3/1989 | Stalker | |
| 4,879,219 A | 11/1989 | Wands et al. | |
| 4,940,835 A | 7/1990 | Shah et al. | |
| 4,971,908 A | 11/1990 | Kishore et al. | |
| 5,004,863 A | 4/1991 | Umbeck | |
| 5,011,771 A | 4/1991 | Bellet et al. | |
| 5,013,659 A | 5/1991 | Bedbrook et al. | |
| 5,015,580 A | 5/1991 | Christou et al. | |
| 5,023,243 A | 6/1991 | Tullis | |
| 5,034,506 A | 7/1991 | Summerton et al. | |
| 5,094,945 A | 3/1992 | Comai | |
| 5,141,870 A | 8/1992 | Bedbrook et al. | |

(Continued)

FOREIGN PATENT DOCUMENTS

| AU | 2008258254 B2 | 7/2014 |
|---|---|---|
| AU | 2014262189 B2 | 11/2014 |

(Continued)

OTHER PUBLICATIONS

Kim et al. (Internationaljournal of pharmaceutics 427.1 (2012):123-133). (Year: 2012).*
Sigma AldrichTM website, https://www.sigmaaldrich.com/life-science/custom-oligos/sirna-oligos/n-ter-nanoparticle.html, retrieve Nov. 20, 2018. (Year: 2018).*
Simeoni et al. (Nucleic Acids Research, 2003, vol. 31, No. 11 2717-2724). (Year: 2003)*
Cheon, et al. (J Microbiol Biotechnol 19.8 (2009): 781-6). (Year: 2009).*
Molinaro, et al. (Expert opinion on drug delivery 10.12 (2013): 1653-1668). (Year: 2013).*
Sawahel, (Plant Molecular Biology Reporter 19.4 (2001): 377-377). (Year: 2001).*

(Continued)

*Primary Examiner* — Charles Logsdon
(74) *Attorney, Agent, or Firm* — Morrison & Foerster LLP

(57) ABSTRACT

Transfection of plant cells with dsRNA through foliar application encounters cuticle, cell wall and plasmalemma three major barriers. We developed cationic polymer and sugar based formulations and protocols that can effectively deliver dsRNA into plant cells resulted in gene silencing. This disclosure covers the novel methods to deliver dsRNA into plant suspension cells with 'one step' treatment and plant foliar cells with 'one step' topical application.

12 Claims, 31 Drawing Sheets

Specification includes a Sequence Listing.

(56) References Cited

U.S. PATENT DOCUMENTS

| | | | |
|---|---|---|---|
| 5,145,783 | A | 9/1992 | Kishore et al. |
| 5,159,135 | A | 10/1992 | Umbeck |
| 5,166,315 | A | 11/1992 | Summerton et al. |
| 5,177,196 | A | 1/1993 | Meyer, Jr. et al. |
| 5,185,444 | A | 2/1993 | Summerton et al. |
| 5,188,642 | A | 2/1993 | Shah et al. |
| 5,188,897 | A | 2/1993 | Suhadolnik et al. |
| 5,192,659 | A | 3/1993 | Simons |
| 5,214,134 | A | 5/1993 | Weis et al. |
| 5,216,141 | A | 6/1993 | Benner |
| 5,235,033 | A | 8/1993 | Summerton et al. |
| 5,264,423 | A | 11/1993 | Cohen et al. |
| 5,264,562 | A | 11/1993 | Matteucci |
| 5,264,564 | A | 11/1993 | Matteucci |
| 5,272,057 | A | 12/1993 | Smulson et al. |
| 5,276,019 | A | 1/1994 | Cohen et al. |
| 5,281,521 | A | 1/1994 | Trojanowski et al. |
| 5,286,634 | A | 2/1994 | Stadler et al. |
| 5,286,717 | A | 2/1994 | Cohen et al. |
| 5,304,732 | A | 4/1994 | Anderson et al. |
| 5,310,667 | A | 5/1994 | Eichholtz et al. |
| 5,312,910 | A | 5/1994 | Kishore et al. |
| 5,321,131 | A | 6/1994 | Agrawal et al. |
| 5,331,107 | A | 7/1994 | Anderson et al. |
| 5,339,107 | A | 8/1994 | Henry et al. |
| 5,346,107 | A | 9/1994 | Bouix et al. |
| 5,378,824 | A | 1/1995 | Bedbrook et al. |
| 5,384,253 | A | 1/1995 | Krzyzek et al. |
| 5,390,667 | A | 2/1995 | Kumakura et al. |
| 5,392,910 | A | 2/1995 | Bell et al. |
| 5,393,175 | A | 2/1995 | Courville |
| 5,399,676 | A | 3/1995 | Froehler |
| 5,405,938 | A | 4/1995 | Summerton et al. |
| 5,405,939 | A | 4/1995 | Suhadolnik et al. |
| 5,416,011 | A | 5/1995 | Hinchee et al. |
| 5,453,496 | A | 9/1995 | Caruthers et al. |
| 5,455,233 | A | 10/1995 | Spielvogel et al. |
| 5,459,127 | A | 10/1995 | Feigner et al. |
| 5,460,667 | A | 10/1995 | Moriyuki et al. |
| 5,462,910 | A | 10/1995 | Ito et al. |
| 5,463,174 | A | 10/1995 | Moloney et al. |
| 5,463,175 | A | 10/1995 | Barry et al. |
| 5,466,677 | A | 11/1995 | Baxter et al. |
| 5,470,967 | A | 11/1995 | Huie et al. |
| 5,476,925 | A | 12/1995 | Letsinger et al. |
| 5,489,520 | A | 2/1996 | Adams et al. |
| 5,489,677 | A | 2/1996 | Sanghvi et al. |
| 5,491,288 | A | 2/1996 | Chaubet et al. |
| 5,510,471 | A | 4/1996 | Lebrun et al. |
| 5,518,908 | A | 5/1996 | Corbin et al. |
| 5,519,126 | A | 5/1996 | Hecht |
| 5,536,821 | A | 7/1996 | Agrawal et al. |
| 5,538,880 | A | 7/1996 | Lundquist et al. |
| 5,541,306 | A | 7/1996 | Agrawal et al. |
| 5,541,307 | A | 7/1996 | Cook et al. |
| 5,550,111 | A | 8/1996 | Suhadolnik et al. |
| 5,550,318 | A | 8/1996 | Adams et al. |
| 5,550,398 | A | 8/1996 | Kocian et al. |
| 5,550,468 | A | 8/1996 | Häberlein et al. |
| 5,558,071 | A | 9/1996 | Ward et al. |
| 5,561,225 | A | 10/1996 | Maddry et al. |
| 5,561,236 | A | 10/1996 | Leemans et al. |
| 5,563,253 | A | 10/1996 | Agrawal et al. |
| 5,569,834 | A | 10/1996 | Hinchee et al. |
| 5,571,799 | A | 11/1996 | Tkachuk et al. |
| 5,587,361 | A | 12/1996 | Cook et al. |
| 5,591,616 | A | 1/1997 | Hiei et al. |
| 5,593,874 | A | 1/1997 | Brown et al. |
| 5,596,086 | A | 1/1997 | Matteucci et al. |
| 5,597,717 | A | 1/1997 | Guerineau et al. |
| 5,602,240 | A | 2/1997 | De Mesmaeker et al. |
| 5,605,011 | A | 2/1997 | Bedbrook et al. |
| 5,608,046 | A | 3/1997 | Cook et al. |
| 5,610,289 | A | 3/1997 | Cook et al. |
| 5,618,704 | A | 4/1997 | Sanghvi et al. |
| 5,623,070 | A | 4/1997 | Cook et al. |
| 5,625,050 | A | 4/1997 | Beaton et al. |
| 5,627,061 | A | 5/1997 | Barry et al. |
| 5,633,360 | A | 5/1997 | Bischofberger et al. |
| 5,633,435 | A | 5/1997 | Barry et al. |
| 5,633,448 | A | 5/1997 | Lebrun et al. |
| 5,639,024 | A | 6/1997 | Mueller et al. |
| 5,646,024 | A | 7/1997 | Leemans et al. |
| 5,648,477 | A | 7/1997 | Leemans et al. |
| 5,663,312 | A | 9/1997 | Chaturvedula |
| 5,677,437 | A | 10/1997 | Teng et al. |
| 5,677,439 | A | 10/1997 | Weis et al. |
| 5,719,046 | A | 2/1998 | Guerineau et al. |
| 5,721,138 | A | 2/1998 | Lawn |
| 5,731,180 | A | 3/1998 | Dietrich |
| 5,739,180 | A | 4/1998 | Taylor-Smith |
| 5,746,180 | A | 5/1998 | Jefferson et al. |
| 5,767,361 | A | 6/1998 | Dietrich |
| 5,767,373 | A | 6/1998 | Ward et al. |
| 5,780,708 | A | 7/1998 | Lundquist et al. |
| 5,804,425 | A | 9/1998 | Barry et al. |
| 5,824,877 | A | 10/1998 | Hinchee et al. |
| 5,837,848 | A | 11/1998 | Ely et al. |
| 5,859,347 | A | 1/1999 | Brown et al. |
| 5,866,775 | A | 2/1999 | Eichholtz et al. |
| 5,874,265 | A | 2/1999 | Adams et al. |
| 5,879,903 | A | 3/1999 | Strauch et al. |
| 5,914,451 | A | 6/1999 | Martinell et al. |
| 5,919,675 | A | 7/1999 | Adams et al. |
| 5,928,937 | A | 7/1999 | Kakefuda et al. |
| 5,939,602 | A | 8/1999 | Volrath et al. |
| 5,965,404 | A | 10/1999 | Buschle et al. |
| 5,969,213 | A | 10/1999 | Adams et al. |
| 5,981,840 | A | 11/1999 | Zhao et al. |
| 5,985,793 | A | 11/1999 | Sandbrink et al. |
| RE36,449 | E | 12/1999 | Lebrun et al. |
| 6,040,497 | A | 3/2000 | Spencer et al. |
| 6,056,938 | A | 5/2000 | Unger et al. |
| 6,069,115 | A | 5/2000 | Pallett et al. |
| 6,084,089 | A | 7/2000 | Mine et al. |
| 6,084,155 | A | 7/2000 | Volrath et al. |
| 6,118,047 | A | 9/2000 | Anderson et al. |
| 6,121,513 | A | 9/2000 | Zhang et al. |
| 6,130,366 | A | 10/2000 | Herrera-Estrella et al. |
| 6,140,078 | A | 10/2000 | Sanders et al. |
| 6,153,812 | A | 11/2000 | Fry et al. |
| 6,160,208 | A | 12/2000 | Lundquist et al. |
| 6,177,616 | B1 | 1/2001 | Bartsch et al. |
| 6,194,636 | B1 | 2/2001 | McElroy et al. |
| 6,225,105 | B1 | 5/2001 | Sathasivan et al. |
| 6,225,114 | B1 | 5/2001 | Eichholtz et al. |
| 6,232,526 | B1 | 5/2001 | McElroy et al. |
| 6,245,968 | B1 | 6/2001 | Boudec et al. |
| 6,248,876 | B1 | 6/2001 | Barry et al. |
| 6,252,138 | B1 | 6/2001 | Karimi et al. |
| RE37,287 | E | 7/2001 | Lebrun et al. |
| 6,268,549 | B1 | 7/2001 | Sailland et al. |
| 6,271,359 | B1 | 8/2001 | Norris et al. |
| 6,282,837 | B1 | 9/2001 | Ward et al. |
| 6,288,306 | B1 | 9/2001 | Ward et al. |
| 6,288,312 | B1 | 9/2001 | Christou et al. |
| 6,294,714 | B1 | 9/2001 | Matsunaga et al. |
| 6,326,193 | B1 | 12/2001 | Liu et al. |
| 6,329,571 | B1 | 12/2001 | Hiei |
| 6,348,185 | B1 | 2/2002 | Piwnica-Worms |
| 6,365,807 | B1 | 4/2002 | Christou et al. |
| 6,384,301 | B1 | 5/2002 | Martinell et al. |
| 6,385,902 | B1 | 5/2002 | Schipper et al. |
| 6,399,861 | B1 | 6/2002 | Anderson et al. |
| 6,403,865 | B1 | 6/2002 | Koziel et al. |
| 6,414,222 | B1 | 7/2002 | Gengenbach et al. |
| 6,421,956 | B1 | 7/2002 | Boukens et al. |
| 6,426,446 | B1 | 7/2002 | McElroy et al. |
| 6,433,252 | B1 | 8/2002 | Kriz et al. |
| 6,437,217 | B1 | 8/2002 | McElroy et al. |
| 6,453,609 | B1 | 9/2002 | Soll et al. |
| 6,479,291 | B2 | 11/2002 | Kumagai et al. |
| 6,506,559 | B1 | 1/2003 | Fire et al. |
| 6,506,599 | B1 | 1/2003 | Yoon |

(56) References Cited

U.S. PATENT DOCUMENTS

| | | |
|---|---|---|
| 6,642,435 B1 | 11/2003 | Rafalski et al. |
| 6,644,341 B1 | 11/2003 | Chemo et al. |
| 6,645,914 B1 | 11/2003 | Woznica et al. |
| 6,768,044 B1 | 7/2004 | Boudec et al. |
| 6,992,237 B1 | 1/2006 | Habben et al. |
| 7,022,896 B1 | 4/2006 | Weeks et al. |
| 7,026,528 B2 | 4/2006 | Cheng et al. |
| RE39,247 E | 8/2006 | Barry et al. |
| 7,105,724 B2 | 9/2006 | Weeks et al. |
| 7,119,256 B2 | 10/2006 | Shimizu et al. |
| 7,138,564 B2 | 11/2006 | Tian et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,392,379 B2 | 6/2008 | Le Pennec et al. |
| 7,405,347 B2 | 7/2008 | Hammer et al. |
| 7,406,981 B2 | 8/2008 | Hemo et al. |
| 7,462,379 B2 | 12/2008 | Fukuda et al. |
| 7,485,777 B2 | 2/2009 | Nakajima et al. |
| 7,525,013 B2 | 4/2009 | Hildebrand et al. |
| 7,550,578 B2 | 6/2009 | Budworth et al. |
| 7,622,301 B2 | 11/2009 | Ren et al. |
| 7,657,299 B2 | 2/2010 | Huizenga et al. |
| 7,671,254 B2 | 3/2010 | Tranel et al. |
| 7,714,188 B2 | 5/2010 | Castle et al. |
| 7,738,626 B2 | 6/2010 | Weese et al. |
| 7,807,791 B2 | 10/2010 | Sekar et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,090,164 B2 | 1/2012 | Bullitt et al. |
| 8,143,480 B2 | 3/2012 | Axtell et al. |
| 8,226,938 B1 | 7/2012 | Meikle et al. |
| 8,548,778 B1 | 10/2013 | Hart et al. |
| 8,554,490 B2 | 10/2013 | Tang et al. |
| 9,121,022 B2 | 9/2015 | Sammons et al. |
| 9,422,557 B2 | 8/2016 | Ader |
| 9,445,603 B2 | 9/2016 | Baum et al. |
| 9,777,288 B2 | 10/2017 | Beattie et al. |
| 9,850,496 B2 | 12/2017 | Beattie et al. |
| 9,856,495 B2 | 10/2018 | Beattie et al. |
| 2001/0006797 A1 | 7/2001 | Kumagai et al. |
| 2001/0042257 A1 | 11/2001 | Connor-Ward et al. |
| 2002/0069430 A1 | 6/2002 | Kiaska et al. |
| 2002/0106653 A1 | 8/2002 | Kurane et al. |
| 2002/0114784 A1 | 8/2002 | Li et al. |
| 2003/0150017 A1 | 8/2003 | Mesa et al. |
| 2003/0154508 A1 | 8/2003 | Stevens et al. |
| 2003/0167537 A1 | 9/2003 | Jiang |
| 2003/0221211 A1* | 11/2003 | Rottmann .......... C12N 15/8218 800/278 |
| 2004/0029275 A1 | 2/2004 | Brown et al. |
| 2004/0053289 A1 | 3/2004 | Allen et al. |
| 2004/0055041 A1 | 3/2004 | Labate et al. |
| 2004/0072692 A1 | 4/2004 | Hoffman et al. |
| 2004/0082475 A1 | 4/2004 | Hoffman et al. |
| 2004/0123347 A1 | 6/2004 | Hinchey et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0216189 A1 | 10/2004 | Houmard et al. |
| 2004/0244075 A1 | 12/2004 | Cai et al. |
| 2004/0250310 A1 | 12/2004 | Shukla et al. |
| 2005/0005319 A1 | 1/2005 | della-Cioppa et al. |
| 2005/0044591 A1 | 2/2005 | Yao et al. |
| 2005/0215435 A1 | 9/2005 | Menges et al. |
| 2005/0223425 A1 | 10/2005 | Clinton et al. |
| 2005/0246784 A1 | 11/2005 | Plesch et al. |
| 2005/0250647 A1 | 11/2005 | Hills et al. |
| 2005/0289664 A1 | 12/2005 | Moshiri et al. |
| 2006/0009358 A1 | 1/2006 | Kibler et al. |
| 2006/0021087 A1 | 1/2006 | Baum et al. |
| 2006/0040826 A1 | 2/2006 | Eaton et al. |
| 2006/0111241 A1 | 5/2006 | Gerwick, III et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0223708 A1 | 10/2006 | Hoffman et al. |
| 2006/0223709 A1 | 10/2006 | Helmke et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011775 A1 | 1/2007 | Allen et al. |
| 2007/0021360 A1 | 1/2007 | Nyce et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0250947 A1 | 10/2007 | Boukharov et al. |
| 2007/0259785 A1 | 11/2007 | Heck et al. |
| 2007/0269815 A1 | 11/2007 | Rivory et al. |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0113351 A1 | 5/2008 | Naito et al. |
| 2008/0155716 A1 | 6/2008 | Sonnewald et al. |
| 2008/0214443 A1 | 9/2008 | Baum et al. |
| 2009/0011934 A1 | 1/2009 | Zawierucha et al. |
| 2009/0018016 A1 | 1/2009 | Duck et al. |
| 2009/0036311 A1 | 2/2009 | Witschel et al. |
| 2009/0054240 A1 | 2/2009 | Witschel et al. |
| 2009/0075921 A1 | 3/2009 | Ikegawa et al. |
| 2009/0094717 A1 | 4/2009 | Troukhan et al. |
| 2009/0098614 A1 | 4/2009 | Zamore et al. |
| 2009/0118214 A1 | 5/2009 | Paldi et al. |
| 2009/0137395 A1 | 5/2009 | Chicoine et al. |
| 2009/0144848 A1 | 6/2009 | Kovalic et al. |
| 2009/0165153 A1 | 6/2009 | Wang et al. |
| 2009/0165166 A1 | 6/2009 | Feng et al. |
| 2009/0172838 A1 | 7/2009 | Axtell et al. |
| 2009/0188005 A1 | 7/2009 | Boukharov et al. |
| 2009/0205079 A1 | 8/2009 | Kumar et al. |
| 2009/0215628 A1 | 8/2009 | Witschel et al. |
| 2009/0285784 A1 | 11/2009 | Raemaekers et al. |
| 2009/0293148 A1 | 11/2009 | Ren et al. |
| 2009/0298787 A1 | 12/2009 | Raemaekers et al. |
| 2009/0306189 A1 | 12/2009 | Raemaekers et al. |
| 2009/0307803 A1 | 12/2009 | Baum et al. |
| 2010/0005551 A1 | 1/2010 | Roberts et al. |
| 2010/0048670 A1 | 2/2010 | Biard et al. |
| 2010/0068172 A1 | 3/2010 | Van De Craen |
| 2010/0071088 A1 | 3/2010 | Sela et al. |
| 2010/0099561 A1 | 4/2010 | Selby et al. |
| 2010/0100988 A1 | 4/2010 | Tranel et al. |
| 2010/0152443 A1 | 6/2010 | Hirai et al. |
| 2010/0154083 A1 | 6/2010 | Ross et al. |
| 2010/0192237 A1 | 7/2010 | Ren et al. |
| 2010/0247578 A1 | 9/2010 | Salama |
| 2010/0248373 A1 | 9/2010 | Baba et al. |
| 2011/0015084 A1 | 1/2011 | Christian et al. |
| 2011/0015284 A1 | 1/2011 | Dees et al. |
| 2011/0028412 A1 | 2/2011 | Cappello et al. |
| 2011/0035836 A1 | 2/2011 | Endes et al. |
| 2011/0041400 A1 | 2/2011 | Trias Vila et al. |
| 2011/0053226 A1 | 3/2011 | Rohayem |
| 2011/0098180 A1 | 4/2011 | Michel et al. |
| 2011/0105327 A1 | 5/2011 | Nelson |
| 2011/0105329 A1 | 5/2011 | Song et al. |
| 2011/0112570 A1 | 5/2011 | Mannava et al. |
| 2011/0126310 A1 | 5/2011 | Feng et al. |
| 2011/0126311 A1 | 5/2011 | Velcheva et al. |
| 2011/0152339 A1 | 6/2011 | Brown et al. |
| 2011/0152346 A1 | 6/2011 | Karleson et al. |
| 2011/0152353 A1 | 6/2011 | Koizumi et al. |
| 2011/0160082 A1 | 6/2011 | Woo et al. |

(56) References Cited

U.S. PATENT DOCUMENTS

| | | |
|---|---|---|
| 2011/0166022 A1 | 7/2011 | Israels et al. |
| 2011/0166023 A1 | 7/2011 | Nettleton-Hammond et al. |
| 2011/0171176 A1 | 7/2011 | Baas et al. |
| 2011/0171287 A1 | 7/2011 | Saarma et al. |
| 2011/0177949 A1 | 7/2011 | Krapp et al. |
| 2011/0185444 A1 | 7/2011 | Li et al. |
| 2011/0185445 A1 | 7/2011 | Bogner et al. |
| 2011/0191897 A1 | 8/2011 | Force et al. |
| 2011/0201501 A1 | 8/2011 | Song et al. |
| 2011/0203013 A1* | 8/2011 | Peterson ............ B82Y 5/00 800/279 |
| 2011/0296555 A1 | 12/2011 | Ivashuta et al. |
| 2011/0296556 A1* | 12/2011 | Sammons .......... C12N 15/8207 435/410 |
| 2012/0036594 A1 | 2/2012 | Cardoza et al. |
| 2012/0107355 A1 | 5/2012 | Harris et al. |
| 2012/0108497 A1 | 5/2012 | Paldi et al. |
| 2012/0137387 A1 | 5/2012 | Baum et al. |
| 2012/0150048 A1 | 6/2012 | Kang et al. |
| 2012/0156784 A1 | 6/2012 | Adams, Jr. et al. |
| 2012/0157512 A1 | 6/2012 | Ben-Chanoch et al. |
| 2012/0164205 A1 | 6/2012 | Baum et al. |
| 2012/0174262 A1 | 7/2012 | Azhakanandam et al. |
| 2012/0185967 A1 | 7/2012 | Sela et al. |
| 2012/0198586 A1 | 8/2012 | Narva et al. |
| 2012/0230565 A1 | 9/2012 | Steinberg et al. |
| 2012/0258646 A1 | 10/2012 | Sela et al. |
| 2013/0003213 A1 | 1/2013 | Kabelac et al. |
| 2013/0041004 A1 | 2/2013 | Drager et al. |
| 2013/0047297 A1 | 2/2013 | Sammons et al. |
| 2013/0047298 A1 | 2/2013 | Tang |
| 2013/0060133 A1 | 3/2013 | Kassab et al. |
| 2013/0067618 A1 | 3/2013 | Ader et al. |
| 2013/0084243 A1 | 4/2013 | Goetsch et al. |
| 2013/0096073 A1 | 4/2013 | Sidelman |
| 2013/0097726 A1 | 4/2013 | Ader et al. |
| 2013/0212739 A1 | 8/2013 | Giritch et al. |
| 2013/0226003 A1 | 8/2013 | Edic et al. |
| 2013/0247247 A1 | 9/2013 | Ader et al. |
| 2013/0254940 A1 | 9/2013 | Ader et al. |
| 2013/0254941 A1 | 9/2013 | Ader et al. |
| 2013/0288895 A1 | 10/2013 | Ader et al. |
| 2013/0318657 A1 | 11/2013 | Avniel et al. |
| 2013/0318658 A1 | 11/2013 | Ader et al. |
| 2013/0324842 A1 | 12/2013 | Mittal et al. |
| 2013/0326731 A1 | 12/2013 | Ader et al. |
| 2014/0018241 A1 | 1/2014 | Sammons et al. |
| 2014/0057789 A1 | 2/2014 | Sammons et al. |
| 2014/0109258 A1 | 4/2014 | Van De Craen et al. |
| 2014/0230090 A1 | 8/2014 | Avniel et al. |
| 2014/0274712 A1 | 9/2014 | Finnessy et al. |
| 2014/0275208 A1 | 9/2014 | Hu et al. |
| 2014/0296503 A1 | 10/2014 | Avniel et al. |
| 2015/0096079 A1 | 4/2015 | Avniel et al. |
| 2015/0143580 A1 | 5/2015 | Beattie et al. |
| 2015/0159156 A1 | 6/2015 | Inberg et al. |
| 2015/0203867 A1 | 7/2015 | Beattie et al. |
| 2015/0218569 A1 | 8/2015 | Numata et al. |
| 2015/0240258 A1 | 8/2015 | Beattie et al. |
| 2016/0015035 A1 | 1/2016 | Tao |
| 2016/0029644 A1 | 2/2016 | Tao |

FOREIGN PATENT DOCUMENTS

| | | |
|---|---|---|
| CN | 101279950 A | 10/2008 |
| CN | 101279951 A | 10/2008 |
| CN | 101892247 A | 11/2010 |
| CN | 101914540 A | 12/2010 |
| CN | 102154364 A | 8/2011 |
| CN | 102481311 A | 5/2012 |
| CN | 102822350 A | 12/2012 |
| CN | 102906263 A | 1/2013 |
| DE | 288618 A5 | 4/1991 |
| DE | 10000600 A1 | 7/2001 |
| DE | 10116399 A1 | 10/2002 |
| DE | 10256353 A1 | 6/2003 |
| DE | 10256354 A1 | 6/2003 |
| DE | 10256367 A1 | 6/2003 |
| DE | 10204951 A1 | 8/2003 |
| DE | 10234875 A1 | 2/2004 |
| DE | 10234876 A1 | 2/2004 |
| DE | 102004054666 A1 | 5/2006 |
| DE | 102005014638 A1 | 10/2006 |
| DE | 102005014906 A1 | 10/2006 |
| DE | 102007012168 A1 | 9/2008 |
| DE | 102010042866 A1 | 5/2011 |
| EP | 0 804 600 A1 | 11/1997 |
| EP | 1 155 615 A1 | 11/2001 |
| EP | 1 157 991 A2 | 11/2001 |
| EP | 1 238 586 A1 | 9/2002 |
| EP | 1 416 049 A1 | 5/2004 |
| EP | 1 496 123 A1 | 1/2005 |
| EP | 1 889 902 A1 | 2/2008 |
| EP | 1 964 919 A1 | 9/2008 |
| EP | 2 147 919 A1 | 1/2010 |
| EP | 2 160 098 B1 | 11/2010 |
| EP | 2 530 159 A1 | 3/2011 |
| EP | 2 305 813 A2 | 4/2011 |
| EP | 2 473 024 A2 | 7/2012 |
| EP | 2 545 182 A1 | 1/2013 |
| JP | 2001-253874 A | 9/2001 |
| JP | 2002-080454 A | 3/2002 |
| JP | 2002-138075 A | 5/2002 |
| JP | 2002-145707 A | 5/2002 |
| JP | 2002-220389 A | 8/2002 |
| JP | 2003-064059 A | 3/2003 |
| JP | 2003-096059 A | 4/2003 |
| JP | 2004-051628 A | 2/2004 |
| JP | 2004-107228 A | 4/2004 |
| JP | 2005-008583 A | 1/2005 |
| JP | 2005-239675 A | 9/2005 |
| JP | 2005-314407 A | 11/2005 |
| JP | 2006-232824 A | 9/2006 |
| JP | 2006-282552 A | 10/2006 |
| JP | 2007-153847 A | 6/2007 |
| JP | 2007-161701 A | 6/2007 |
| JP | 2007-182404 A | 7/2007 |
| JP | 2008-074840 A | 4/2008 |
| JP | 2008-074841 A | 4/2008 |
| JP | 2008-133207 A | 6/2008 |
| JP | 2008-133218 A | 6/2008 |
| JP | 2008-169121 A | 7/2008 |
| JP | 2009-508481 A | 3/2009 |
| JP | 2009-067739 A | 4/2009 |
| JP | 2009-114128 A | 5/2009 |
| JP | 2009-126792 A | 6/2009 |
| JP | 2009-137851 A | 6/2009 |
| JP | 2016-532440 A | 10/2015 |
| RU | 2 291 613 C1 | 1/2007 |
| RU | 2 337 529 C1 | 11/2008 |
| WO | WO 89/11789 A1 | 12/1989 |
| WO | WO 95/34659 A1 | 12/1995 |
| WO | WO 95/34668 A2 | 12/1995 |
| WO | WO 96/005721 A1 | 2/1996 |
| WO | WO 96/033270 A1 | 10/1996 |
| WO | WO 96/038567 A2 | 12/1996 |
| WO | WO 96/040964 A2 | 12/1996 |
| WO | WO 97/49816 A1 | 12/1997 |
| WO | WO 99/14348 A1 | 3/1999 |
| WO | WO 99/024585 A1 | 5/1999 |
| WO | WO 99/26467 A1 | 6/1999 |
| WO | WO 99/27116 A2 | 6/1999 |
| WO | WO 99/32619 A1 | 7/1999 |
| WO | WO 99/61631 A1 | 12/1999 |
| WO | WO 99/67367 A1 | 12/1999 |
| WO | WO 00/32757 A1 | 6/2000 |
| WO | WO 00/044914 A1 | 8/2000 |
| WO | WO 01/07601 A2 | 2/2001 |
| WO | WO 2001/085970 A2 | 11/2001 |
| WO | WO 02/14472 A2 | 2/2002 |
| WO | WO 02/066660 A2 | 8/2002 |
| WO | WO 03/000679 A2 | 1/2003 |
| WO | WO 03/004649 | 1/2003 |

(56) References Cited

FOREIGN PATENT DOCUMENTS

| | | |
|---|---|---|
| WO | WO 03/004649 A1 | 1/2003 |
| WO | WO 03/006422 A1 | 1/2003 |
| WO | WO 03/012052 A2 | 2/2003 |
| WO | WO 03/013247 A1 | 2/2003 |
| WO | WO 03/016308 A1 | 2/2003 |
| WO | WO 2003/014357 A1 | 2/2003 |
| WO | WO 03/020704 A1 | 3/2003 |
| WO | WO 03/022051 A1 | 3/2003 |
| WO | WO 03/022831 A1 | 3/2003 |
| WO | WO 03/022843 A1 | 3/2003 |
| WO | WO 03/029243 A2 | 4/2003 |
| WO | WO 03/037085 A1 | 5/2003 |
| WO | WO 03/037878 A1 | 5/2003 |
| WO | WO 03/045878 A2 | 6/2003 |
| WO | WO 03/050087 A2 | 6/2003 |
| WO | WO 03/051823 A1 | 6/2003 |
| WO | WO 03/051824 A1 | 6/2003 |
| WO | WO 03/051846 A2 | 6/2003 |
| WO | WO 03/064625 A2 | 8/2003 |
| WO | WO 03/076409 A1 | 9/2003 |
| WO | WO 03/077648 A2 | 9/2003 |
| WO | WO 03/087067 A1 | 10/2003 |
| WO | WO 03/090539 A1 | 11/2003 |
| WO | WO 03/091217 A1 | 11/2003 |
| WO | WO 03/093269 A2 | 11/2003 |
| WO | WO 03/104206 A2 | 12/2003 |
| WO | WO 2004/002947 A1 | 1/2004 |
| WO | WO 2004/002981 A2 | 1/2004 |
| WO | WO 2004/005485 A2 | 1/2004 |
| WO | WO 2004/009761 A2 | 1/2004 |
| WO | WO 2004/011429 A1 | 2/2004 |
| WO | WO 2004/022771 A2 | 3/2004 |
| WO | WO 2004/029060 A1 | 4/2004 |
| WO | WO 2004/035545 A2 | 4/2004 |
| WO | WO 2004/035563 A1 | 4/2004 |
| WO | WO 2004/035564 A1 | 4/2004 |
| WO | WO 2004/037787 A1 | 5/2004 |
| WO | WO 2004/049806 A1 | 6/2004 |
| WO | WO 2004/062351 A2 | 7/2004 |
| WO | WO 2004/067518 A1 | 8/2004 |
| WO | WO 2004/067527 A1 | 8/2004 |
| WO | WO 2004/074443 A2 | 9/2004 |
| WO | WO 2004/077950 A1 | 9/2004 |
| WO | WO 2005/000824 A1 | 1/2005 |
| WO | WO 2005/003362 A2 | 1/2005 |
| WO | WO 2005/007627 A1 | 1/2005 |
| WO | WO 2005/007860 A1 | 1/2005 |
| WO | WO 2005/040152 A1 | 5/2005 |
| WO | WO 2005/047233 A1 | 5/2005 |
| WO | WO 2005/047281 A1 | 5/2005 |
| WO | WO 2005/061443 A2 | 7/2005 |
| WO | WO 2005/061464 A1 | 7/2005 |
| WO | WO 2005/068434 A1 | 7/2005 |
| WO | WO 2005/070889 A1 | 8/2005 |
| WO | WO 2005/089551 A1 | 9/2005 |
| WO | WO 2005/095335 A1 | 10/2005 |
| WO | WO 2005/107437 A2 | 11/2005 |
| WO | WO 2005/110068 A2 | 11/2005 |
| WO | WO 2006/006569 A1 | 1/2006 |
| WO | WO 2006/024820 A1 | 3/2006 |
| WO | WO 2006/029828 A1 | 3/2006 |
| WO | WO 2006/029829 A1 | 3/2006 |
| WO | WO 2006/037945 A1 | 4/2006 |
| WO | WO 2006/050803 A1 | 5/2006 |
| WO | WO 2006/074400 A2 | 7/2006 |
| WO | WO 2006/090792 A1 | 8/2006 |
| WO | WO 2006/123088 A2 | 11/2006 |
| WO | WO 2006/125687 A1 | 11/2006 |
| WO | WO 2006/125688 A1 | 11/2006 |
| WO | WO 2006/132270 A1 | 12/2006 |
| WO | WO 2006/138638 A1 | 12/2006 |
| WO | WO 2007/003294 A1 | 1/2007 |
| WO | WO 2007/007316 A1 | 1/2007 |
| WO | WO 2007/024783 | 3/2007 |
| WO | WO 2007/026834 A1 | 3/2007 |
| WO | WO 2007/035650 A2 | 3/2007 |
| WO | WO 2007/038788 A2 | 4/2007 |
| WO | WO 2007/039454 A1 | 4/2007 |
| WO | WO 2007/050715 A2 | 5/2007 |
| WO | WO 2007/051462 A2 | 5/2007 |
| WO | WO 2007/070389 A2 | 6/2007 |
| WO | WO 2007/071900 A1 | 6/2007 |
| WO | WO 2007/074405 A2 | 7/2007 |
| WO | WO 2007/077201 A1 | 7/2007 |
| WO | WO 2007/077247 A1 | 7/2007 |
| WO | WO 2007/080126 A2 | 7/2007 |
| WO | WO 2007/080127 A2 | 7/2007 |
| WO | WO 2007/083193 A2 | 7/2007 |
| WO | WO 2007/096576 A1 | 8/2007 |
| WO | WO 2007/051462 A3 | 10/2007 |
| WO | WO 2007/119434 A1 | 10/2007 |
| WO | WO 2007/134984 A1 | 11/2007 |
| WO | WO 2008/007100 A2 | 1/2008 |
| WO | WO 2008/009908 A1 | 1/2008 |
| WO | WO 2008/029084 A1 | 3/2008 |
| WO | WO 2008/042231 A2 | 4/2008 |
| WO | WO 2008/059948 A1 | 5/2008 |
| WO | WO 2008/063203 A2 | 5/2008 |
| WO | WO 2008/071918 A1 | 6/2008 |
| WO | WO 2008/074991 A1 | 6/2008 |
| WO | WO 2008/084073 A1 | 7/2008 |
| WO | WO 2008/100426 A2 | 8/2008 |
| WO | WO 2008/102908 A1 | 8/2008 |
| WO | WO 2008/148223 A1 | 12/2008 |
| WO | WO 2008/152072 A2 | 12/2008 |
| WO | WO 2008/152073 A2 | 12/2008 |
| WO | WO 2009/000757 A1 | 12/2008 |
| WO | WO 2009/005297 A2 | 1/2009 |
| WO | WO 2009/029690 A1 | 3/2009 |
| WO | WO 2009/035150 A2 | 3/2009 |
| WO | WO 2009/037329 A2 | 3/2009 |
| WO | WO 2009/046384 A1 | 4/2009 |
| WO | WO 2009/060429 A2 | 5/2009 |
| WO | WO 2009/063180 A1 | 5/2009 |
| WO | WO 2009/068170 A2 | 6/2009 |
| WO | WO 2009/068171 A2 | 6/2009 |
| WO | WO 2009/086041 A1 | 7/2009 |
| WO | WO 2009/090401 A2 | 7/2009 |
| WO | WO 2009/090402 A2 | 7/2009 |
| WO | WO 2009/115788 A1 | 9/2009 |
| WO | WO 2009/116558 A1 | 9/2009 |
| WO | WO 2009/125401 A2 | 10/2009 |
| WO | WO 2009/144079 A1 | 12/2009 |
| WO | WO 2009/152995 A1 | 12/2009 |
| WO | WO 2009/153607 A1 | 12/2009 |
| WO | WO 2009/158258 A1 | 12/2009 |
| WO | WO 2010/012649 A1 | 2/2010 |
| WO | WO 2010/026989 A1 | 3/2010 |
| WO | WO 2010/034153 A1 | 4/2010 |
| WO | WO 2010/049270 A1 | 5/2010 |
| WO | WO 2010/049369 A1 | 5/2010 |
| WO | WO 2010/049405 A1 | 5/2010 |
| WO | WO 2010/049414 A1 | 5/2010 |
| WO | WO 2010/056519 A1 | 5/2010 |
| WO | WO 2010/063422 A1 | 6/2010 |
| WO | WO 2010/069802 A1 | 6/2010 |
| WO | WO 2010/078906 A2 | 7/2010 |
| WO | WO 2010/078912 A1 | 7/2010 |
| WO | WO 2010/093788 A2 | 8/2010 |
| WO | WO 2010/104217 A1 | 9/2010 |
| WO | WO 2010/108611 A1 | 9/2010 |
| WO | WO 2010/112826 A2 | 10/2010 |
| WO | WO 2010/116122 A2 | 10/2010 |
| WO | WO 2010/119906 A1 | 10/2010 |
| WO | WO 2010/130970 A1 | 11/2010 |
| WO | WO 2011/001434 A1 | 1/2011 |
| WO | WO 2011/003776 A1 | 1/2011 |
| WO | WO 2011/028836 A2 | 3/2011 |
| WO | WO 2011/035874 A1 | 3/2011 |
| WO | WO 2011/045796 A1 | 4/2011 |
| WO | WO 2011/065451 A1 | 6/2011 |
| WO | WO 2011/067745 A2 | 6/2011 |
| WO | WO 2011/075188 A1 | 6/2011 |
| WO | WO 2011/080674 A2 | 7/2011 |

(56) References Cited

FOREIGN PATENT DOCUMENTS

| | | |
|---|---|---|
| WO | WO 2011/112570 A1 | 9/2011 |
| WO | WO 2011/132127 A1 | 10/2011 |
| WO | WO 2012/001626 A1 | 1/2012 |
| WO | WO 2012/056401 A1 | 5/2012 |
| WO | WO 2012/092580 A2 | 7/2012 |
| WO | WO 2012/156342 A1 | 11/2012 |
| WO | WO 2012/164100 A2 | 12/2012 |
| WO | WO 2013/010691 A1 | 1/2013 |
| WO | WO 2013/025670 A1 | 2/2013 |
| WO | WO 2013/039990 A1 | 3/2013 |
| WO | WO 2013/040005 A1 | 3/2013 |
| WO | WO 2013/040021 A1 | 3/2013 |
| WO | WO 2013/040033 A1 | 3/2013 |
| WO | WO 2013/040049 A1 | 3/2013 |
| WO | WO 2013/040057 A1 | 3/2013 |
| WO | WO 2013/040116 A9 | 3/2013 |
| WO | WO 2013/040117 A9 | 3/2013 |
| WO | 2013129698 A1 | 9/2013 |
| WO | WO 2013/153553 A2 | 10/2013 |
| WO | WO 2013/175480 A1 | 11/2013 |
| WO | WO 2014/022739 A2 | 2/2014 |
| WO | WO 2014/106837 A2 | 7/2014 |
| WO | WO 2014/106838 A2 | 7/2014 |
| WO | WO 2014/151255 A1 | 9/2014 |
| WO | WO 2014/164761 A1 | 10/2014 |
| WO | WO 2014/164797 A2 | 10/2014 |
| WO | WO 2015/010026 A2 | 1/2015 |
| WO | WO 2015/200539 A1 | 12/2015 |

OTHER PUBLICATIONS

Agricultural Chemical Usage 2006 Vegetables Summary, Agricultural Statistics Board, NASS, USDA, pp. 1-372 (2007).
Agrios, Plant Pathology (Second Edition), 2:466-470 (1978).
Alarcón-Reverte et al., "Resistance to ACCase-inhibiting herbicides in the weed Lolium multiflorum," Comm. Appl. Biol. Sci., 73(4):899-902 (2008).
Al-Kaff et al., "Plants rendered herbicide-susceptible by cauliflower mosaic virus-elicited suppression of a 35S promoter-regulated transgene," Nature Biotechnology, 18:995-999 (2000).
Amarzguioui et al., "An algorithm for selection of functional siRNA sequences," Biochemical and Biophysical Research Communications, 316:1050-1058 (2004).
Ambrus et al., "The Diverse Roles of RNA Helicases in RNAi," Cell Cycle, 8(21):3500-3505 (2009).
An et al., "Transient RNAi Induction against Endogenous Genes in *Arabidopsis* Protoplasts Using in Vitro-Prepared Double-Stranded RNA," Biosci Biotechnol Biochem, 69(2):415-418 (2005).
Andersen et al., "Delivery of siRNA from lyophilized polymeric surfaces," Biomaterials, 29:506-512 (2008).
Andersson et al., "A novel selection system for potato transformation using a mutated AHAS gene," Plant Cell Reports, 22(4):261-267 (2003).
Anonymous, "Resistant Weeds Spur Research Into New Technologies," Grains Research & Development Corporation, 2013.
Anonymous, "A handbook for high-level expression and purification of 6xHis-tagged proteins," the QiaExpressionist, (2003).
Anonymous, "Agronomy Facts 37: Adjuvants for enhancing herbicide performance," n.p. 1-8, (Jan. 26, 2000), Web, (Jan. 21, 2014).
Anonymous, "Devgen, The mini-Monsanto," KBC Securities (2006).
Anonymous, "Do Monsanto have the next big thing?," Austalian Herbicide Resistance Initiative (AHRI), (Apr. 23, 2013) Web. (Jan. 19, 2015).
Aoki et al., "In Vivo Transfer Efficiency of Antisense Oligonucleotides into the Myocardium Using HVJ-Liposome Method," Biochem Biophys Res Commun, 231:540-545 (1997).
Arpaia et al., "Production of transgenic eggplant (*Solanum melongena* L.) resistant to Colorado Potato Beetle (*Leptinotarsa decemlineata* Say)," (1997) Theor. Appl. Genet., 95:329-334 (1997).

Artymovich, "Using Rna interference to increase crop yield and decrease pest damage," MMG 445 Basic Biotech., 5(1):7-12 (2009).
Asad et al., "Silicon Carbide Whisker-mediated Plant Transformation," Properties and Applicants of Silicon Carbide, pp. 345-358 (2011).
Ascencio-Ibanez et al., "DNA abrasion onto plants is an effective method for geminivirus infection and virus-induced gene silencing," Journal of Virological Methods, 142:198-203 (2007).
Axtell et al., "A Two-Hit Trigger for siRNA Biogenesis in Plants," Cell, 127:565-577 (2006).
Bachman et al., "Characterization of the spectrum of insecticidal activity of a double-stranded RNA with targeted activity against Western Corn Rootworm (*Diabrotica virgifera virgifera* LeConte)," Transgenic Res., pp. 1-16 (2013).
Baerson et al., "Glyphosate-Resistant Goosegrass. Identification of a Mutation in the Target Enzyme 5-Enolpyruvylshikimate-3-Phosphate Synthase," Plant Physiol., 129(3):1265-1275 (2002).
Bai et al., "Naturally Occurring Broad-Spectrum Powdery Mildew Resistance in a Central American Tomato Accession Is Caused by Loss of Mlo Function," MPMI, 21(1):30-39 (2008).
Baker, "Chlorophyll Fluorescence: A Probe of Photosynthesis in Vivo," Annu. Rev. Plant Biol., 59:89-113 (2008).
Balibrea et al., "Extracellular Invertase is an Essential Component of Cytokinin-Mediated Delay of Senescence," The Plant Cell, 16(5):1276-1287.
Bannerjee et al., "Efficient production of transgenic potato (*S. tuberosum* L. ssp. *andigena*) plants via Agrobacterium tumefaciens-mediated transformation," Plant Sci., 170:732 738 (2006).
Bart et al., "A novel system for gene silencing using siRNAs in rice leaf and stem-derived protoplasts," Plant Methods, 2(13):1-9 (2006).
Basu et al., "Weed genomics: new tools to understand weed biology," Trends in Plant Science, 9(8):391-398 (2004).
Bauer et al., "The major protein import receptor of plastids is essential for chloroplast biogenesis," Nature, 403:203-207 (2000).
Baulcombe, RNA silencing in plants, Nature, 431:356-363 (2004).
Baulcombe, "RNA silencing and heritable epigenetic effects in tomato and *Arabidopsis*," Abstract 13th Annual Fall Symposium, Plant Genomes to Phenomes, Donald Danforth Plant Science Center, 28-30 (2011).
Baum et al., "Progress Towards RNAi-Mediated Insect Pest Management" Advances in Insect Physiology, 47:249-295 (2014).
Bayer et al., "Programmable ligand-controlled riboregulators of eukaryotic gene expression," Nature Biotechnol., 23(3):337-343 (2005).
Beal, et al., "Second Structural Motif for Recognition of DNA by Oligonucleotide-Directed Triple-Helix Formation," Science, 251:1360-1363 (1992).
Becker et al., "Fertile transgenic wheat from microprojectile bombardment of scutellar tissue," The Plant Journal, 5(2):299-307 (1994).
Bedell et al., "Sorghum Genome Sequencing by Methylation Filtration," Plos Biology, 3(1):E13/104-115 (2005).
Belhadj et al., "Methyl Jasmonate Induces Defense Responses in Grapevine and Triggers Protection against Erysiphe necator," J. Agric Food Chem., 54:9119-9125 (2006).
Bhargava et al., "Long double-stranded RNA-mediated RNA interference as a tool to achieve site-specific silencing of hypothalamic neuropeptides," Brain Research Protocols, 13:115-125 (2004).
Boletta et al., "High Efficient Non-Viral Gene Delivery to the Rat Kidney by Novel Polycationic Vectors," J. Am Soc. Nephrol., 7:1728 (1996).
Bolognesi et al., "Characterizing the Mechanism of Action of Double-Stranded RNA Activity against Western Corn Rootworm(*Diabrotica virgifera virgifera* LeConte)," PLoS One 7(10):e47534 (2012).
Bolter et al., "A chloroplastic inner envelope membrane protease is essential for plant development," FEBS Letters, 580:789-794 (2006).
Bourgeois et al., "Field and producer survey of ACCase resistant wild oat in Manitoba," Canadian Journal of Plant Science, 709-715 (1997).
Breaker et al., "A DNA enzyme with Mg2+-dependent RNA phosphoesterase activity," Chemistry and Biology, 2:655-660 (1995).

(56) References Cited

OTHER PUBLICATIONS

Brodersen et al., "The diversity of RNA silencing pathways in plants," Trends in Genetics, 22(5):268-280 (2006).
Brugière et al., "Glutamine Synthetase in the Phloem Plays a Major Role in Controlling Proline Production," The Plant Cell, 11:1995-2011 (1999).
Burgos et al., "Review: Confirmation of Resistance to Herbicides and Evaluation of Resistance Levels," Weed Science, 61 (1):4-20 (2013).
Burleigh, "Relative quantitative RT-PCR to study the expression of plant nutrient transporters in arbuscular mycorrhizas," Plant Science, 160:899-904 (2001).
Busch et al., "RNAi for discovery of novel crop protection products," Pflanzenschutz-Nachrichten Bayer, 58(1):34-50 (2005).
Busi et al., "Gene flow increases the initial frequency of herbicide resistance alleles in unselected populations," Agriculture, Ecosystems and Environments, Elsevier, Amsterdam, NL, 142(3):403-409 (2011).
Butler et al., "Priming and re-drying improve the survival of mature seeds of Digitalis purpurea during storage," Annals of Botany, 103:1261-1270 (2009).
Bytebier et al., "T-DNA organization in tumor cultures and transgenic plants of the monocotyledon Asparagus officinalis," Proc. Natl. Acad. Sci. U.S.A., 84:5345-5349 (1987).
Campbell et al., "Gene-knockdown in the honey bee mite Varroa destructor by a non-invasive approach: studies on a glutathione S-transferase," Parasites & Vectors, 3(1):73, pp. 1-10 (2010).
Chabannes et al., "In situ analysis of lignins in transgenic tobacco reveals a differential impact of individual transformations on the spatial patterns of lignin deposition at the cellular and subcellular levels," The Plant Journal, 28(3):271-282 (2001).
Chabbouh et al., "Cucumber mosaic virus in artichoke," FAO Plant Protection Bulletin, 38:52-53 (1990).
Chakravarty et al., "Genetic Transformation in Potato: Approaches and Strategies," Amer J Potato Res, 84:301 311 (2007).
Chang et al., "Dual-target gene silencing by using long, sythetic siRNA duplexes without triggering antiviral responses," Molecules and Cells, 27(6):689-695 (2009).
Chang et al., "Cellular Internalization of Fluorescent Proteins via Arginine-rich Intracellular Delivery Peptide in Plant Cells," Plant Cell Physiol., 46(3):482-488 (2005).
Chee et al., "Transformation of Soybean (*Glycine max*) by Infecting Germinating Seeds with Agrobacterium tumefaciens," Plant Physiol., 91:1212-1218 (1989).
Chen et al., "Exploring MicroRNA-Like Small RNAs in the Filamentous Fungus Fusarium oxysporum," Plos One, 9(8):e104956:1-10 (2014).
Chen et al., "In Vivo Analysis of the Role of atTic20 in Protein Import into Chloroplasts," the Plant Cell, 14:641-654 (2002).
Chen et al., "Transfection and Expression of Plasmid DNA in Plant Cells by an Arginine-Rich Intracellular Delivery Peptide without Protoplast Preparation," FEBS Letters 581, pp. 1891-1897 (2007).
Cheng et al., "Transient Expression of Minimum Linear Gene Cassettes in Onion Epidermal Cells via Direct Transformation," Appl Biochem Biotechnol, 159:739-749 (2009).
Cheng et al., "Production of fertile transgenic peanut (*Arachis hypogaea* L.) plants using Agrobacterium tumefaciens," Plant Cell Reports, 15:653-657 (1996).
Chi et al., "The Function of RH22, a DEAD RNA Helicase, in the Biogenesis of the 50S Ribosomal Subunits of Arabidopsis Chloroplasts," Plant Physiology, 158:693-707 (2012).
Christiaens et al., "The challenge of RNAi-mediated control of hemipterans," Current Opinion in Insect Science, 6:15-21 (2014).
Chupp et al., "Chapter 8: White Rusk" Vegetable Diseases and Their Control, The Ronald Press Company, New York, pp. 267-269 (1960).
Clough et al., "Floral dip: a simplified method for Agrobacterium-mediated transformation of *Arabidopsis thaliana*," The Plant Journal, 16(6):735-743.

CN101914540 Patent Disclosure, "Introduction of RNA into plant by interference," (2010).
Colbourne et al., "The Ecoresponsive Genome of Daphnia Pulex," Science, 331(6017):555-561 (2011).
Colliver et al., "Differential modification of flavonoid and isoflavonoid biosynthesis with an antisense chalcone synthase construct in transgenic Lotus corniculatus," Plant Molecular Biology, 35:509-522 (1997).
Communication pursuant to Article 94(3) EPC dated Jan. 14, 2016, in European Patent Application No. 12 832 415.9.
Communication pursuant to Article 94(3) EPC dated Jun. 26, 2015, in European Patent Application No. 11 753 916.3.
Communication pursuant to Article 94(3) EPC dated Mar. 18, 2016, in European Patent Application No. 12 832 160.1.
Communication pursuant to Article 94(3) EPC dated Mar. 24, 2016, in European Patent Application No. 12 831 684.1.
Communication pursuant to Article 94(3) EPC dated Mar. 4, 2016, in European Patent Application No. 12 830 932.5.
Communication pursuant to Article 94(3) EPC dated Mar. 9, 2016, in European Patent Application No. 12 831 166.9.
Communication pursuant to Article 94(3) EPC dated Oct. 23, 2015, in European Patent Application No. 12 831 945.6.
Communication Pursuant to Article 94(3) EPC dated Sep. 5, 2018, in European Patent Application No. 17152830.0.
Concise Descriptions of Relevance filed by a third party on Nov. 29, 2012, in U.S. Appl. No. 13/042,856.
Constan et al., "An outer envelope membrane component of the plastid protein import apparatus plays an essential role in *Arabidopsis*," The Plant Journal, 38:93-106 (2004).
Cooney et al., "Site-Specific Oligonucleotide Binding Represses Transcription of the Human c-myc Gene in Vitro," Science (1988) ,241:456-459.
Cost Action FA0806 progress report "Plant virus control employing RNA-based vaccines: a novel non-transgenic strategy" (2010).
Coticchia et al., "Calmodulin modulates Akt activity in human breast cancer cell lines," Breast Cancer Res. Treat, 115:545-560 (2009).
Dalakouras et al., "Induction of Silencing in Plants by High-Pressure Spraying of in vitro-Synthesized Small RNAs," Frontiers in Plant Science, 7(1327):1-5 (2016).
Dalmay et al., "An RNA-Depenedent Rna Polymerase Gene in *Arabidopsis* Is Required for Posttranscriptional Gene Silencing Mediated by a Transgene but Not by a Virus," Cell, 101:543-553 (2000).
Database EMBL XP-002781749(BG442539) dated Mar. 20, 2001.
Davidson et al., "Engineering regulatory RNAs," Trends in Biotechnology, 23(3):109-112 (2005).
Dawson et al., "cDNA cloning of the complete genome of tobacco mosaic virus and production of infectious transcripts," Proc. Natl. Acad. Sci. USA, 83:1832-1836 (1986).
Declaration of Jerzy Zabkiewicz executed Nov. 28, 2017, as filed by Opponent in Australian Patent Application No. 2014262189, pp. 1-73.
Declaration of Jerzy Zabkiewicz executed Nov. 28, 2017, as filed by Opponent in Australian Patent Application No. 2014262189, pp. 1-4.
Declaration of Neena Mitter executed Nov. 30, 2017, as filed by Opponent in Australian Patent Application No. 2014262189, pp. 1-114.
Declaration of Neena Mitter executed Nov. 30, 2017, as filed by Opponent in Australian Patent Application No. 2014262189, pp. 1-25.
De Framond, "MINI-Ti: A New Vector Strategy for Plant Genetic Engineering," Nature Biotechnology, 1:262-269 (1983).
Della-Cioppa et al., "Import of a precursor protein into chloroplasts is inhibited by the herbicide glyphosate," the EMBO Journal, 7(5):1299-1305 (1988).
Delye et al., "PCR-based detection of resistance to acetyl-CoA carboxylase-herbicides in black-grass (*Alopecurus myosuroides* Huds) and ryegrass (*Lolium rigidum* Gaud)," Pest Management Science, 58:474-478 (2002).

(56) References Cited

OTHER PUBLICATIONS

Delye et al., "Variation in the gene encoding acetolactate-synthase in *Lolium* species and proactive detection of mutant, herbicide-resistant alleles," Weed Research, 49:326-336 (2009).
Desai et al., "Reduction in deformed wing virus infection in larval and adult honey bees (*Apis mellifera* L.) by double-stranded RNA ingestion," Insect Molecular Biology, 21(4):446-455 (2012).
Desveaux et al., "PBF-2 Is a Novel Single-Stranded DNA Binding Factor Implicated in PR-10α Gene Activation in Potato," The Plant Cell, 12:1477-1489 (2000).
Di Stilio et al., "Virus-Induced Gene Silencing as a Tool for Comparative Functional Studies in Thalictrum," PLoS One, 5(8):e12064 (2010).
Diallo et al., "Long Endogenous dsRNAs Can Induce Complete Gene Silencing in Mammalian Cells and Primary Cultures," Oligonucleotides, 13:381-392 (2003).
Dietemann et al., "Varroa destructor: research avenues towards sustainable control," Journal of Apicultural Research, 51(1):125-132 (2012).
Dietzgen et al., "Transgenic gene silencing strategies for virus control," Australasian Plant Pathology, 35:605-618 (2006).
Dilpreet et al., "Glyphosate Resistance in a Johnsongrass (*Sorghum halepense*) Biotype from Arkansas," Weed Science, 59(3):299-304 (2011).
Downey et al., "Single and dual parasitic mite infestations on the honey bee, *Apis mellifera* L.," Insectes Sociaux, 47(2):171-176 (2000).
Du et al., "A systematic analysis of the silencing effects of an active siRNA at all single-nucleotide mismatched target sites," Nucleic Acids Research, 33(5):1671-1677 (2005).
Duhoux et al., "Reference Genes to Study Herbicide Stress Response in *Lolium* sp.: Up-Regulation of P3450 Genes in Plants Resistant to Acetolactate-Synthase Inhibitors," PLOS One, 8(5):e63576 (2013).
Dunoyer et al., "Small RNA Duplexes Function as Mobile Silencing Signals Between Plant Cells," Science, 328:912-916 (2010).
Eamens et al., "RNA Silencing in Plants: Yesterday, Today, and Tomorrow," Plant Physiology, 147(2):456-468 (2008).
Egli et al., "A Maize Acetyl-Coenzyme A Carboxylase cDNA Sequence," Plant Physiol., 108: 1299-1300 (1995).
Ellington et al., "In vitro selection of RNA molecules that bind specific ligands," Nature, 346:818-822 (1990).
Emery et al., "Radial Patterning of *Arabidopsis* Shoots by Class III HD-ZIP and KANADI Genes," Current Biology, 13:1768-1774 (2003).
Eudes et al., "Cell-penetrating peptides," Plant Signaling & Behavior, 3(8):549-5550 (2008).
European Cooperation in the field of Scientific and Technical Research—Memorandum of Understanding for COST Action FA0806 (2008).
European Search Report dated Sep. 7, 2017, in European Patent Application No. 17152830.0.
Examination Report dated Mar. 1, 2018, in Australian Patent Application No. 2013264742.
Extended European Search Report dated Dec. 19, 2018, in European Patent Application No. 16804395.8.
Extended European Search Report dated Feb. 2, 2015, in European Patent Application No. 12 830 932.5.
Extended European Search Report dated Feb. 27, 2015, in European Patent Application No. 12 832 160.1.
Extended European Search Report dated Feb. 3, 2015, in European Patent Application No. 12 831 945.6.
Extended European Search Report dated Jan. 20, 2016, in European Patent Application No. 13 794 339.5.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Jun. 29, 2015, in European Patent Application No. 12 831 494.5.
Extended European Search Report dated Mar. 17, 2015, in European Patent Application No. 12 831 684.1.
Extended European Search Report dated Mar. 3, 2015, in European Patent Application No. 12 831 166.9.
Extended European Search Report dated Nov. 16, 2018, in European Patent Application No. 18182238.8.
Extended European Search Report dated Nov. 21, 2018, in European Patent Application No. 18175809.5.
Extended European Search Report dated Nov. 7, 2017, in European Patent Application No. 15811092.4.
Extended European Search Report dated Nov. 8, 2017, in European Patent Application No. 15737282.2.
Extended European Search Report dated Oct. 8, 2013, in European Patent Application No. 11753916.3.
Extended European Search Report dated Sep. 28, 2018, in European Patent Application No. 16740770.9.
Extended European Search Report dated Sep. 29, 2016, in European Patent Application No. 14778840.0.
Extended European Search Report issued on Apr. 13, 2018, in European Patent Application No. 15812530.0.
Extended European Search Report issued on Mar. 15, 2018, in European Patent Application No. 17181861.0.
Farooq et al., "Rice seed priming," IPRN, 30(2):45-48 (2005).
Fassler, BLAST Glossary, National Center for Biotechnology Information (2011).
Fernandez et al., "Uptake of Hydrophilic Solutes Through Plant Leaves: Current State of Knowledge and Perspectives of Foliar Fertilization," Critical Reviews in Plant Sciences, 28:36-38 (2009).
Feuillet et al., "Crop genome sequencing: lessons and rationales," Trends Plant Sci., 16:77-88 (2011).
Final Office Action dated Apr. 7, 2016, in U.S. Appl. No. 13/619,980.
Final Office Action dated Dec. 17, 2015, in U.S. Appl. No. 14/335,135.
Final Office Action dated Feb. 17, 2016, in U.S. Appl. No. 13/612,929.
Final Office Action dated Feb. 4, 2016, in U.S. Appl. No. 13/612,936.
Final Office Action dated Jun. 30, 2016, in U.S. Appl. No. 13/901,326.
Final Office Action dated Mar. 2, 2016, in U.S. Appl. No. 13/612,995.
Final Office Action dated Mar. 21, 2016, in U.S. Appl. No. 13/612,925.
Final Office Action dated May 26, 2016, in U.S. Appl. No. 14/532,596.
Final Office Action dated Nov. 10, 2015, in U.S. Appl. No. 13/612,985.
Final Office Action dated Nov. 10, 2016, in U.S. Appl. No. 13/583,302.
Final Office Action dated Nov. 19, 2015, in U.S. Appl. No. 13/612,941.
Final Office Action dated Nov. 30, 2015, in U.S. Appl. No. 13/612,948.
Final Office Action dated Nov. 7, 2013, in U.S. Appl. No. 13/042,856.
Final Office Action dated Oct. 20, 2016, in U.S. Appl. No. 14/480,199.
Final Office Action dated Oct. 22, 2015, in U.S. Appl. No. 14/608,951.
Final Office Action dated Sep. 9, 2016, in U.S. Appl. No. 13/612,954.
Final Office Action dated Sep. 9, 2016, in U.S. Appl. No. 14/608,951.
Final Office Action dated Sep. 9, 2016, in U.S. Appl. No. 14/603,347.
Fire et al., "Potent and specific genetic interference by double-stranded RNA in Caenorhabditis elegans," Nature, 391:806-811 (1998).
First Examination Report dated Apr. 23, 2013, in New Zealand Patent Application No. 601784.
First Examination Report dated Jul. 28, 2014, in New Zealand Patent Application No. 627060.
First Office Action dated Aug. 31, 2015, in Chinese Patent Application No. 201280053985.3.
First Office Action dated Feb. 2, 2016, in Chinese Patent Application No. 201380039346.6.
First Office Action dated Jul. 7, 2015, in Chinese Patent Application No. 201280054820.8.
First Office Action dated Mar. 12, 2015, in Chinese Patent Application No. 201280053984.9.
First Office Action dated Mar. 2, 2015, in Chinese Patent Application No. 201280054819.5.
First Office Action dated May 27, 2015, in Chinese Patent Application No. 201280054179.8.
First Office Action dated Sep. 9, 2015, in Chinese Patent Application No. 201280055409.2.
Fraley et al., "Liposome-mediated delivery of tobacco mosaic virus RNA into tobacco protoplasts: A sensitive assay for monitoring liposome-protoplast interactions," Proc Natl Acad Sci U S A., 79(6):1859-1863 (1982).

(56) References Cited

OTHER PUBLICATIONS

Friedberg, "Automated protein function prediction—the genomic challenge," Briefings in Bioinformatics, 7(3):225-242 (2006).
Fukuhara et al., "Enigmatic Double-Stranded RNA in Japonica Rice," Plant Molecular Biology, 21:1121-1130 (1993).
Fukuhara et al., "The Unusual Structure of a Novel RNA Replicon in Rice," The Journal of Biological Chemistry, 270(30):18147-18149 (1995).
Fukuhara et al., "The wide distribution of endornaviruses, large double-stranded RNA replicons with plasmid-like properties," Archives of Virology, 151:995-1002 (2006).
Fukunaga et al., "dsRNA with 5' overhangs v contributes to endogenous and antiviral RNA silencing pathways in plants," The EMBO Journal, 28(5):545-555 (2009).
Funke et al., "Molecular basis for herbicide resistance in Roundup Ready crops," PNAS, 103:13010-13015 (2006).
Further Examination Report dated May 16, 2014, in New Zealand Patent Application No. 601784.
Gaines et al., "Gene amplification confers glyphosate resistance in Amaranthus Palmeri," Proc. Natl. Acad. Sci. USA, 107(3):1029-1034 (2010).
Gallie et al., "Identification of the motifs within the tobacco mosaic virus 5'leader responsible for enhancing translation," Nucleic Acids Res., 20(17):4631-4638 (1992).
Gan et al., "Bacterially expressed dsRNA protects maize against SCMV infection," Plant Cell Rep, 29(11):1261-1268 (2010).
Gan et al., "Inhibition of Leaf Senescence by Autoregulated Production of Cytokinin," Science, 270:1986-1988 (1995).
Gao et al., "Down-regulation of acetolactate synthase compromises 01-1-mediated resistance to powdery mildew in tomato," BMC Plant Biology, 14 (2014).
Gao et al., "Nonviral Methods for siRNA Delivery," Molecular Pharmaceutics, 6(3):651-658 (2008).
Garbian et al., "Bidirectional Transfer of RNAi between Honey Bee and Varroa destructor: Varroa Gene Silencing Reduces Varroa Population," 8(12):1-9:e1003035 (2012).
Gaskin et al., "Novel organosillicone adjuvants to reduce agrochemical spray volumes on row crops," New Zealand Plant Protection, 53:350-354 (2000).
Gasser et al., "Structure, Expression, and Evolution of the 5-Enolpyruvylshikimate-3-phosphate Synthase Genes of Petunia and Tomato," J. Biol. Chem., 263: 4280-4287 (1988).
Ge et al., "Rapid vacuolar sequestration: the horseweed glyphosate resistance mechanism," Pest Management Sci., 66:345-348 (2010).
GenBank Accession No. AY545657.1 (2004).
GenBank Accession No. CB377464, "CmaE1_37_J02_T3 Cowpea weevil larvae Lambda Zap Express Library Callosobruchus maculatus cDNA, mRNA sequence," (2007).
GenBank Accession No. DY640489, "PU2_plate27_F03 PU2 Prunus persica cDNA similar to expressed mRNA inferred from Prunus persica hypothetical domain/motif cont aining IPR011005:Dihydropteroate synthase-like, MRNA sequence" (2006).
GenBank Accession No. EF143582 (2007).
GenBank Accession No. EU024568, "Amaranthus hypochondriacus acetolactate synthase (ALS) gene" (2007).
GenBank Accession No. EW765249, "ST020010B10C12 Normalized and subtracted western corn rootworm female head cDNA library Diabrotica virgifera virgifera cDNA clone STO20010B10C12 5-, mRNA sequence," (2007).
GenBank Accession No. EW771198, "ST020010B10C12 Normalized and subtracted western corn rootworm female head cDNA library Diabrotica virgifera virgifera cDNA clone STO20010B10C12 5-, mRNA sequence," (2007).
GenBank Accession No. FE348695, "CBIB7954.fwd CBIB_Daphnia_pulex_Chosen_One_Library_2 Daphnia pulex cDNA clone CBIB7954 5, mRNA sequence" (2011).
GenBank Accession No. FJ972198, "Solanum lycopersicum cultivar Ailsa Craig dihydropterin pyrophosphokinase-dihydropteroate synthase (HPPK-DHPS) gene, complete cds" (2010).
GenBank Accession No. GI:186478573 (2014).
GenBank Accession No. GU120406, "Chrysomela tremulae ribosomal protein L7 (RpL7) mRNA, complete cds" (2009).
GenBank Accession No. HD315444, "Sequence 192160 from Patent EP2213738" (2010).
GenBank Accession No. Q4GXM3_BIPLU, "Ribosomal protein L7e" (2006).
GenBank Accession No. U87257.1, "Daucus carota 4-hydroxyphenylpyruvate dioxygenase mRNA, complete cds" (1997).
GenBank Accession No. XM_014456745.1, Predicted: Myotis lucifugus ribonucleoprotein, PTB-binding 2 (RAVER2), transcript variant X3, mRNA,: (2015).
GenBank Accession No. Y08611.1, "P.sativum mRNA for dihydropterin pyrophosphokinase/dihydropteroate synthase " (2006).
GenEmbl Accession No. FJ861243 (2010).
Gilmer et al., "Latent Viruses of Apple I. Detection with Woody Indicators," Plant Pathology, 1(10):1-9 (1971).
Gomez-Zurita et al., "Recalibrated Tree of Leaf Beetles (*Chiysomelidae*) Indicates Independent Diversification of Angiosperms and Their Insect Herbivores," PLoS One, 4(e360):1-8 (2007).
Gong et al., "Silencing of Rieske iron-sulfur protein using chemically synthesised siRNA as a potential biopesticide against Plutella xylostella," Pest Manag Sci, 67:514-520 (2011).
Gossamer Threads, Compendium of Herbicide Adjuvants: Organo-Silicone Surfactant, p. 1-4 (1998).
Gressel et al., "A strategy to provide long-term control of weedy rice while mitigating herbicide resistance transgene flow, and its potential use for other crops with related weeds," Pest Manag Sci, 65(7):723-731 (2009).
Gudkov, "Minireview: The L7/L12 ribosomal domain of the ribosome: structural and functional studies," FEBS Letters, 407:253-256 (1997).
Gutensohn et al., "Functional analysis of the two *Arabidopsis* homologues of Toc34, a component of the chloroplast protein import apparatus," The Plant Journal, 23(6):771-783 (2000).
Guttieri et al., "DNA Sequence Variation in Domain A of the Acetolactate Synthase Genes of Herbicide-Resistant and -Susceptible Weed Biotypes," Weed Science, 40:670-679 (1992).
Hagio, "Chapter 25: Direct Gene Transfer into Plant Mature Seeds via Electroporation After Vacuum Treatment," Electroporation and Sonoporation in Developmental Biology, p. 285-293 (2009).
Haigh, "The Priming of Seeds: Investigation into a method of priming large quantities of seeds using salt solutions," Thesis submitted to Macquarie University (1983).
Hajirezaei et al., "Impact of elevated cytosolic and apoplastic invertase activity on carbon metabolism during potato tuber development," Journal of Experimental Botany, 51:439-445 (2000).
Hamilton et al., "Guidelines for the Identification and Characterization of Plant Herewith Viruses," J. gen. Virol., 54:223-241 (1981).
Hamilton et al., "Two classes of short interfering RNA in RNA silencing" EMBO J., 21(17):4671-4679 (2002).
Han et al., "Molecular Basis for the Recognition of Primary microRNAs by the Drosha-DGCR8 Complex," Cell, 125(5):887-901 (2006).
Hannon, "RNA interference," Nature,481:244-251 (2002).
Hardegree, "Drying and storage effects on germination of primed grass seeds," Journal of Range Management, 47(3):196-199 (1994).
Harrison et al., "Does Lowering Glutamine Synthetase Activity in Nodules Modigy Nitrogen Metabolism and Growth of Lotus japonicus?," Plant Physiology, 133:253-262 (2003).
Heffer et al., "Rapid isolation of gene homologs across taxa: Efficient identification and isolation of gene orthologs from non-model organism genomes, a technical report," EvoDevo Journal, 2(7):1-5 (2011).
Herman et al., "A three-component dicamba O-demethylase from Pseudomonas maltophilia, strain DI-6: gene isolation, characterization, and heterologous expression," J. Biol. Chem., 280: 24759-24767 (2005).
Hess, "Surfactants and Additives," 1999 Proceedings of the California Weed Science Society, 51:156-172 (1999).
Hewezi et al., "Local infiltration of high- and low-molecular-weight RNA from silenced sunflower (*Helianthus annuus* L.) plants trig-

(56) References Cited

OTHER PUBLICATIONS gers post-transcriptional gene silencing in non-silenced plants," Plant Biotechnology Journal, 3:81-89 (2005).
Hidayat et al., "Enhanced Metabolism of Fluazifop Acid in a Biotype of Digitaria sanguinalis Resistant to the Herbicide Fluazifop-P-Butyl," Pesticide Biochem. Physiol., 57:137-146 (1997).
Himber et al., "Transitivity-dependant and -independent cell-to-cell movement of RNA silencing," The EMBO Journal, 22(17):4523-4533 (2003).
Hirschberg et al., "Molecular Basis of Herbicide Resistance in Amaranthus hybridus," Science, 222:1346-1349 (1983).
Hoekema et al., "A binary plant vector strategy based on separation of vir- and T-region of the Agrobacterium tumefaciens Ti-plasmid," Nature, 303:179-180 (1983).
Hofgen et al., "Repression of Acetolactate Synthase Activity through Antisense Inhibition: Molecular and Biochemical Analysis of Transgenic Potato (*Solanum tuberosum* L. cv Desiree) Plants," Plant Physiol., 107(2):469-477 (1995).
Holtra et al., "Assessment of the Physiological Condition of Salvinia Natans L. Exposed to Copper(II) Ions," Environ. Protect. Eng., 41:147-158 (2015).
Hörmann et al., "Tic32, as Essential Component in Chloroplast Biogenesis," The Journal of Biological Chemistry, 279(33):34756-34762 (2004).
Hsieh et al., "A library of siRNA duplexes targeting the phosphoinositide 3-kinase pathway: determinants of gene silencing for use in cell-based screens," Nucleic Acids Res., 32(3):893-901 (2004).
Hu et al., "High efficiency transport of quantum dots into plant roots with the aid of silwet L-77," Plant Physiology and Biochemistry, 48:703-709 (2010).
Huang et al., "In Vivo Analyses of the Roles of Essential Omp85-Related Proteins in the Chloroplast Outer Envelope Membrane," Plant Physiol., 157:147-159 (2011).
Huesken et al., "Design of a genome-wide siRNA library using an artificial neural network," Nature Biotechnology, 23(8): 995-1001 (2005).
Huggett et al., "Real-time RT-PCR normalisation; strategies and considerations," Genes and Immunity, 6:279-284 (2005).
Hunter et al., "RNA Interference Strategy to suppress Psyllids & Leafhoppers," International Plant and Animal Genome XIX, 15-19 (2011).
Ichihara et al., "Thermodynamic instability of siRNA duplex is a prerequisite for dependable prediction of siRNA activities," Nucleic Acids Res., 35(18):e123 (2007).
Inaba et al., "*Arabidopsis* Tic110 Is Essential for the Assembly and Function of the Protein Import Machinery of Plastids," the Plant Cell, 17:1482-1496 (2005).
International Preliminary Report on Patentability (Chapter II) dated Jul. 24, 2015, in International Application No. PCT/US2014/047204.
International Preliminary Report on Patentability dated Sep. 11, 2012, International Application No. PCT/US2011/027528.
International Preliminary Report on Patentability dated Sep. 11, 2014, in International Application No. PCT/IL2013/050447.
International Rice Genome Sequencing Project, The map-based sequence of the rice genome, Nature, 436(11):793-800 (2005).
International Search Report and the Written Opinion dated Feb. 25, 2013, in International Application No. PCT/US2012/054883.
International Search Report and the Written Opinion dated Feb. 27, 2013, in International Application No. PCT/US2012/054814.
International Search Report and the Written Opinion dated Feb. 27, 2013, in International Application No. PCT/US2012/054842.
International Search Report and the Written Opinion dated Feb. 27, 2013, in International Application No. PCT/US2012/054862.
International Search Report and the Written Opinion dated Feb. 27, 2013, in International Application No. PCT/US2012/054894.
International Search Report and the Written Opinion dated Feb. 27, 2013, in International Application No. PCT/US2012/054974.
International Search Report and the Written Opinion dated Feb. 27, 2013, in International Application No. PCT/US2012/054980.
International Search Report and the Written Opinion dated Jul. 15 2014, in International Application No. PCT/US2014/025305.
International Search Report and the Written Opinion dated Jul. 22 2014, in International Application No. PCT/IL2013/051083.
International Search Report and the Written Opinion dated Jul. 22 2014, in International Application No. PCT/IL2013/051085.
International Search Report and the Written Opinion dated Jul. 24 2014, in International Application No. PCT/US2014/026036.
International Search Report and the Written Opinion dated May 10, 2011, in International Application No. PCT/US2011/027528.
International Search Report and the Written Opinion dated Oct. 1, 2013, inInternational Application No. PCT/IL2013/050447.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Feb. 23, 2015, in International Application No. PCT/US2014/063832.
International Search Report and Written Opinion dated Jul. 8, 2015, in International Application No. PCT/US2015/011408.
International Search Report and Written Opinion dated Mar. 26, 2015, in International Application No. PCT/US2014/069353.
International Search Report and Written Opinion dated May 26, 2016, in International Application No. PCT/US2016/014344.
International Search Report and Written Opinion dated Nov. 24, 2015, in International Application No. PCT/US2015/037522.
International Search Report and Written Opinion dated Nov. 27, 2015, in International Application No. PCT/US2015/037015.
International Search Report dated Mar. 12, 2013, in International Application No. PCT/US2012/054789.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Invitation to Pay Additional Fees dated Sep. 8, 2015, in International Application No. PCT/US2015/037015.
Invitation to Pay Additional Fees dated Sep. 9, 2015, in International Application No. PCT/US2015/037522.
Isaacs et al., "Engineered riboregulators enable post-transcriptional control of gene expression," Nature Biotechnology, 22(7):841-847 (2004).
Ivanova et al., "Members of the Toc159 Import Receptor Family Represent Distinct Pathways for Protein Targeting to Plastids," Molecular Biology of the Cell, 15:3379-3392 (2004).
Jacque et al., "Modulation of HIV-1 replication by RNA interference," Nature, 418, 435-438 (2002).
Jang et al., "Resistance to herbicides caused by single amino acid mutations in acetyl-CoA carboxylase in resistant populations of grassy weeds," New Phytologist, 197(4):1110-1116 (2013).
Jarvis et al, "An *Arabidopsis* mutant defective in the plastid general protein import apparatus," Science, 282:100-103 (1998).
Ji et al., "Regulation of small RNA stability: methylation and beyond," Cell Research, 22:624-636 (2012).
Jiang et al., Chapter III Seeds and Seedlings, Botany, Northwest A&F University Press, pp. 87-92 (2009).
Jin et al., "Posttranslational Elevation of Cell Wall Invertase Activity by Silencing its Inhibitor in Tomato Delays Leaf Senescence and Increases Seed Weight and Fruit Hexose Level," The Plant Cell, 21:2072-2089 (2009).
Jofre-Garfias et al., "Agrobacterium-mediated transformation of Amaranthus hypochondriacus: light- and tissue-specific expression of a pea chlorophyll a/b-binding protein promoter," Plant Cell Reports, 16:847-852 (1997).
Jones-Rhoades et al., "MicroRNAs and Their Regulatory Roles in Plants," Annu. Rev. Plant Biol., 57:19-53 (2006).
Josse et al., "A DELLA in Disguise: Spatula Restrains the Growth of the Developing *Arabidopsis* Seedling," Plant Cell, 23:1337-1351 (2011).
Kaloumenos et al., "Identification of a Johnsongrass (Sorghum halepense) Biotype Resistant to ACCase-Inhibiting Herbicides in Northern Greece," Weed Herewith. Technol, 23:470-476 (2009).

(56) References Cited

OTHER PUBLICATIONS

Kam et al., "Nanotube Molecular Transporters: Internalization of Carbon Nanotube-Protein Conjugates into Mammalian Cells," J. Am. Chem. Soc., 126(22):6850-6851 (2004).

Kambiranda et al., "Relationship Between Acid Invertase Activity and Sugar Content in Grape Species," Journal of Food Biochemistry, 35:1646-1652 (2011).

Katoh et al., "Specific residues at every third position of siRNA shape its efficient RNAi activity," Nucleic Acids Res., 35(4): e27 (2007).

Kertbundit et al., "In vivo random ß-glucuronidase gene fusions in *Arabidopsis thaliana*," Proc. Natl. Acad. Sci. U S A., 88:5212-5216 (1991).

Khachigian, "DNAzymes: Cutting a path to a new class of therapeutics," Curr Opin Mol Ther 4(2):119-121 (2002).

Khan et al., "Matriconditioning of Vegetable Seeds to Improve Stand Establishment in Early Field Plantings," J. Amer. Soc. Hort. Sci., 117(1):41-47 (1992).

Khodakovskaya et al., "Carbon Nanotubes Are Able to Penetrate Plant Seed Coat and Dramatically Affect Seed Germination and Plant Growth," ACS Nano, 3(10):3221-3227 (2009).

Kikkert et al., "Stable Transformation of Plant Cells by Particle Bombardment/Biolistics," Methods in Molecular Biology, 286:61-78 (2005).

Kim et al., "Optimization of Conditions for Transient Agrobacterium-Mediated Gene Expression Assays in *Arabidopsis*," Plant Cell Reports, 28:1159-1167 (2009).

Kim et al., "Synthetic dsRNA Dicer substrates enhance RNAi potency and efficacy," Nature Biotechnology, 23(2):222-226 (2005).

Kirkwood, "Herbicides and Plants," Botanical Journal of Scotland, 46(3):447-462 (1993).

Kirkwood, "Use and Mode of Action of Adjuvants for Herbicides: A Review of some Current Work," Pestic Sci., 38:93-102 (1993).

Kirkwood, "Recent developments in our understanding of the plant cuticle as a barrier to the foliar uptake of pesticides," Pestic Sci, 55:69-77 (1999).

Klahre et al., "High molecular weight RNAs and small interfering RNAs induce systemic posttranscriptional gene silencing in plants," Proc. Natl. Acad. Sci. USA, PNAS, 99(18):11981-11986 (2002).

Knudsen, "Promoter2.0: for the recognition of Pol I promoter sequences," Bioinformatics, 15(5):356-361 (1999).

Kovacheva et al., "Further in vivo studies on the role of the molecular chaperone, Hsp93, in plastid protein import," The Plant Journal, 50:364-379 (2007).

Kovacheva et al., "In vivo studies on the roles of Tic100, Tic40 and Hsp93 during chloroplast protein import," The Plant Journal, 41:412-428 (2005).

Kronenwett et al., "Oligodeoxyribonucleotide Uptake in Primary Human Hematopoietic Cells Is Enhanced by Cationic Lipids and Depends on the Hematopoietic Cell Subset," Blood, 91(3):852-862 (1998).

Kumar et al., "Sequencing, De Novo Assembly and Annotation of the Colorado Potato Beetle, Leptinotarsa decemlineata,Transcriptome," PLoS One, 9(1):e86012 (2014).

Kusaba et al., "Low glutelin content1: A Dominant Mutation That Suppresses the Glutelin Multigene Family via RNA Silencing ni Rice," The Plant Cell, 15(6):1455-1467 (2003).

Kusaba, "RNA interference in crop plants," Curr Opin Biotechnol, 15(2):139-143 (2004).

Lavigne et al., "Enhanced antisense inhibition of human immunodeficiency virus type 1 in cell cultures by DLS delivery system," Biochem Biophys Res Commun, 237:566-571 (1997).

Lee et al., "Aptamer Database," Nucleic Acids Research, 32:D95-D100 (2004).

Lein et al., "Target-based discovery of novel herbicides," Current Opinion in Plant Biology, 7:219-225 (2004).

Leopold et al., "Chapter 4: Moisture as a Regulator of Physiological Reaction in Seeds," Seed Moisture, CSSA Special Publication No. 14, pp. 51-69 (1989).

Lermontova et al., "Reduced activity of plastid protoporphyrinogen oxidase causes attenuated photodynamic damage during high-light compared to low-light exposure," The Plant Journal, 48(4):499-510 (2006).

Lesnik et al., "Prediction of rho-independent transcriptional terminators in *Escherichia coli*," Nucleic Acids Research, 29(17):3583-3594 (2001).

Li et al., "A Simplified Seed Transformation Method for Obtaining Transgenic Brassica napus Plants," Agricultural Sciences in China, 8(6):658-663 (2009).

Li et al., "Establishment of a highly efficient transformation system for pepper (*Capsicum annuum* L.)," Plant Cell Reports, 21: 785-788 (2003).

Li et al., "The FAST technique: a simplified Agrobacterium-based transformation method for transient gene expression analysis in seedlings of *Arabidopsis* and other plant species," Plant Methods, 5(6):1-15 (2009).

Li et at., "Long dsRNA but not siRNA initiates RNAi in western corn rootworm larvae and adults," Journal of Applied Entomology, 139(6):432-445 (2015).

Liu et al, "The Helicase and RNaseIIIa Domains of Arabidopsis Dicer-Like1 Modulate Catalytic Parameters during MicroRNA Biogenesis," Plant Physiology, 159:748-758 (2012).

Liu et al., "Carbon Nanotubes as Molecular Transporters for Walled Plant Cells," Nano Letters, 9(3):1007-1010 (2009).

Liu et al., "Comparative study on the interaction of DNA with three different kinds of surfactants and the formation of multilayer films," Bioelectrochemistiy, 70:301-307 (2007).

Liu et al., "DNAzyme-mediated recovery of small recombinant RNAs from a 5S rRNA-derived chimera expressed in *Escherichia coli*," BMC Biotechnology, 10:85 (2010).

Liu et al., "Identification and Application of a Rice Senescence-Associated Promoter," Plant Physiology, 153:1239-1249 (2010).

Liu, "Calmodulin and Cell Cycle," Foreign Medical Sciences Section of Pathophysiology and Clinical Medicine, 18(4):322-324 (1998).

Liu, "Confocal laser scanning microscopy—an attractive tool for studying the uptake of xenobiotics into plant foliage," Journal of Microscopy, 213(Pt 2):87-93 (2004).

Liu, "Influence of Sugars on the Foliar Uptake of Bentazone and Glyphosate," New Zealand Plant Protection, 55:159-162 (2002).

Liu, "The Transformation of Nucleic Acid Degradants in Plants," China Organic Fertilizers, Agriculture Press, ISBN: 7-1091634 (1991) (with English translation).

Llave et al., "Endogenous and Silencing-Associated Small RNAs in Plants," The Plant Cell, 14:1605-1619 (2002).

Lodish et al., Molecular Cell Biology, Fourth Edition, p. 210 (2000).

Lu et al., "OligoWalk: an online siRNA design tool utilizing hybridization thermodynamics," Nucleic Acids Research, 36:W104-W108 (2008).

Lu et al., "RNA silencing in plants by the expression of siRNA duplexes," Nucleic Acids Res., 32(21):e171 (2004).

Lucas et al., "Plasmodesmata—bridging the gap between neighboring plant cells," Trends in Cell Biology, 19:495-503 (2009).

Luft, "Making sense out of antisense oligodeoxynucleotide delivery: getting there is half the fun," J Mol Med, 76:75-76 (1998).

Luque et al., "Water Permeability of Isolated Cuticular Membranes: A Structural Analysis," Archives of Biochemistry and Biophysics, 317(2):417-422 (1995).

Maas et al., "Mechanism and optimized conditions for PEG mediated DNA transfection into plant protoplasts," Plant Cell Reports, 8:148-149 (1989).

MacKenzie et al., "Transgenic Nicotiana debneyii expressing viral coat protein are resistant to potato virus S infection," Journal of General Virology, 71:2167-2170 (1990).

Maher III et al "Inhibition of Dna binding proteins by oligonucleotide-directed triple helix formation," Science, 245(4919):725-730 (1989).

Makkouk et al., "Virus Diseases of Peas, Beans, and Faba Bean in the Mediterranean region," Adv Virus Res, 84:367-402 (2012).

Mandal et al., "Adenine riboswitches and gene activation by disruption of a transcription terminator," Nature Struct. Mol. Biol., 11(1):29-35 (2004).

(56) References Cited

OTHER PUBLICATIONS

Mandal et al., "Gene Regulation by Riboswitches," Nature Reviews | Molecular Cell Biology, 5:451-463 (2004).
Manoharan, "Oligonucleotide Conjugates as Potential Antisense Drugs with Improved Uptake, Biodistribution, Targeted Delivery, and Mechanism of Action," Antisense & Nucleic Acid Drug Development, 12:103-128 (2002).
Maori et al., "IAPV, a bee-affecting virus associated with Colony Collapse Disorder can be silenced by dsRNA ingestion," Insect Molecular Biology, 18(1):55-60 (2009).
Masoud et al., "Constitutive expression of an inducible 13β-1,3-glucanase in alfalfa reduces disease severity caused by the oomycete pathogen Phytophthora megasperma f. spmedicaginis, but does not reduce disease severity of chitincontaining fungi," Transgenic Research, 5(5):313-323 (1996).
Matveeva et al., "Prediction of antisense oligonucleotide efficacy by in vitro methods," Nature Biotechnology, 16:1374-1375 (1998).
McGinnis, "RNAi for functional genomics in plants," Brief Funct Genomics, 9(2):111-7 (2010).
Meinke, et al., "Identifying essential genes in *Arabidopsis thaliana*," Trends Plant Sci., 13(9):483-491 (2008).
Meins et al., "RNA Silencing Systems and Their Relevance to Plant Development," Annu. Rev. Cell Dev. Biol., 21:297-318 (2005).
Melnyk et al., "Intercellular and systemic movement of RNA silencing signals," The EMBO Journal, 30:3553-3563 (2011).
Migge et al., "Greenhouse-grown conditionally lethal tobacco plants obtained by expression of plastidic glutamine synthetase antisense RNA may contribute to biological safety," Plant Science 153:107-112 (2000).
Misawa et al., "Expression of an Erwinia phytoene desaturase gene not only confers multiple resistance to herbicides interfering with carotenoid biosynthesis but also alters xanthophyll metabolism in transgenic plants," The Plant Journal, 6(4):481-489 (1994).
Misawa et al., "Functional expression of the Erwinia uredovora carotenoid biosynthesis gene crt1 in transgenic plants showing an increase of β-carotene biosynthesis activity and resistance to the bleaching herbicide norflurazon," The Plant Journal, 4(5):833-840 (1993).
Miura et al., "The Balance between Protein Synthesis and Degradation in Chloroplasts Determines Leaf Variegation in Arabidopsis yellow variegated Mutants," The Plant Cell, 19:1313-1328 (2007).
Molina et al., "Inhibition of protoporphyrinogen oxidase expression in *Arabidopsis* causes a lesion-mimic phenotype that induces systemic acquired resistance," The Plant Journal, 17(6):667-678 (1999).
Molnar et al., "Plant Virus-Derived Small Interfering RNAs Originate redominantly from Highly Structured Single-Stranded Viral RNAs," Journal of Virology, 79(12):7812-7818 (2005).
Molnar et al., "Small Silencing RNAs in Plants Are Mobile and Direct Epigenetic Modification in Recipient Cells," Science, 328:872-875 (2010).
Mora et al., "How Many Species Are There on Earth and in the Ocean?," Plos Biol., 9(8):e100127, p. 1-8 (2011).
Moriyama et al., "Double-stranded RNA in rice: a novel RNA replicon in plants," Molecular & General Genetics, 248(3):364-369 (1995).
Moriyama et al., "Stringently and developmentally regulated levels of a cytoplasmic double-stranded RNA and its high-efficiency transmission via egg and pollen in rice," Plant Molecular Biology, 31:713-719 (1996).
Morozov et al., "Evaluation of Preemergence Herbicides for Control of Diclofop-resistant Italian Ryegrass (*Lolium multiflorum*) in Virginia," Virginia Polytechnic Institute and State University, pp. 43-71 (2004).
Morrissey et al., "Potent and persistent in vivo anti-HBV activity of chemically modified siRNAs," Nat Biotechnol. 23(8):1002-1007 (2005).
Moser et al., "Sequence-Specific Cleavage of Double Helical DNA by Triple Helix Formation," Science, 238:645-646 (1987).
Mount et al., "Gene and Metabolite Regulatory Network Analysis of Early Developing Fruit Tissues Highlights New Candidate Genes for the Control of Tomato Fruit Composition and Development," Plant Physiology, 149:1505-1528 (2009).
Nemeth, "Virus, mycoplasma and rickettsia diseases of fruit trees," Martinus Nijhoff Publishers, 197-204 (1986).
Non-Final Office Action dated Apr. 11, 2013, in U.S. Appl. No. 13/042,856.
Non-Final Office Action dated Apr. 29, 2016, in U.S. Appl. No. 13/583,302.
Non-Final Office Action dated Aug. 10, 2016, in U.S. Appl. No. 13/612,995.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Aug. 19, 2016, in U.S. Appl. No. 13/612,925.
Non-Final Office Action dated Aug. 19, 2016, in U.S. Appl. No. 13/612,929.
Non-Final Office Action dated Aug. 3, 2016, in U.S. Appl. No. 14/015,715.
Non-Final Office Action dated Aug. 5, 2016, in U.S. Appl. No. 14/015,785.
Non-Final Office Action dated Aug. 8, 2016, in U.S. Appl. No. 13/612,936.
Non-Final Office Action dated Dec. 17, 2015, in U.S. Appl. No. 14/532,596.
Non-Final Office Action dated Feb. 10, 2016, in U.S. Appl. No. 13/901,326.
Non-Final Office Action dated Feb. 23, 2016, in U.S. Appl. No. 14/603,347.
Non-Final Office Action dated Feb. 23, 2016, in U.S. Appl. No. 14/608,951.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated Mar. 1, 2016, in U.S. Appl. No. 13/612,954.
Non-Final Office Action dated Mar. 21, 2018, in U.S. Appl. No. 13/619,980.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Non-Final Office Action dated Nov. 9, 2016, in U.S. Appl. No. 14/901,003.
Non-Final Office Action dated Oct. 3, 2016, in U.S. Appl. No. 14/403,491.
Non-Final Office Action dated Sep. 1, 2015, in U.S. Appl. No. 13/612,954.
Non-Final Office Action dated Sep. 11, 2015, in U.S. Appl. No. 13/612,925.
Non-Final Office Action dated Sep. 4, 2015, in U.S. Appl. No. 13/612,995.
Non-Final Office Action dated Sep. 6, 2016, in U.S. Appl. No. 14/335,135.
Nookaraju et al., "Molecular approaches for enhancing sweetness in fruits and vegetables," Scientia Horticulture, 127:1-15 (2010).
Nord-Larsen et al., "Cloning, characterization and expression analysis of tonoplast intrinsic proteins and glutamine synthetase in ryegrass (*Lolium perenne* L.)," Plant Cell Reports, 28(10):1549-1562 (2009).
Notice of Allowance dated Apr. 11, 2016, in U.S. Appl. No. 13/612,985.
Notice of Allowance dated Apr. 19, 2016, in U.S. Appl. No. 13/612,941.

(56) References Cited

OTHER PUBLICATIONS

Notice of Allowance dated Apr. 20, 2016, in U.S. Appl. No. 13/612,948.
Notice of Allowance dated Feb. 23, 2015, in U.S. Appl. No. 13/042,856.
Notice of Allowance dated Jun. 2, 2015, in U.S. Appl. No. 13/042,856.
Notice of Allowance dated Oct. 5, 2015, in U.S. Appl. No. 13/583,302.
Nowak et al., "A new and efficient method for inhibition of Rna viruses by DNA interference," The FEBS Journal, 276:4372-4380 (2009).
Office Action dated Apr. 13, 2016, in Chinese Patent Application No. 201280053985.3.
Office Action dated Aug. 1, 2017, in European Patent Application No. 12 830 932.5.
Office Action dated Aug. 14, 2017, in Israeli Patent Application No. 235878.
Office Action dated Aug. 22, 2017, in Korean Patent Application No. 10-2012-7023415.
Office Action dated Aug. 25, 2016, in Eurasian Patent Application No. 201201264.
Office Action dated Aug. 28, 2013, in Chinese Patent Application No. 201180012795.2.
Office Action dated Aug. 3, 2017, in Chinese Patent Application No. 201480014392.5 (with English translation).
Office Action dated Aug. 3, 2017, in European Patent Application No. 12 831 684.1.
Office Action dated Aug. 8, 2017, in Chilean Patent Application No. 201501874.
Office Action dated Aug. 9, 2018, in Canadian Patent Application No. 2,848,371.
Office Action dated Dec. 13, 2016, in Ukrainian Patent Application No. a 2014 03843.
Office Action dated Dec. 14, 2016, in Ukrainian Patent Application No. a 2014 03850.
Office Action dated Dec. 15, 2016, in Ukrainian Patent Application No. a 2014 03845.
Office Action dated Dec. 15, 2016, in Ukrainian Patent Application No. a 2014 03852.
Office Action dated Dec. 15, 2016, in Ukrainian Patent Application No. a 2014 03849.
Office Action dated Dec. 27, 2016, in Ukrainian Patent Application No. a 2012 11548.
Office Action dated Dec. 5, 2017, in Japanese Patent Application No. 2016-502033.
Office Action dated Feb. 17, 2014, in Mexican Patent Application No. MX/a/2012/010479.
Office Action dated Feb. 21, 2018, in Mexican Patent Application No. MX/a/2015/012632 (with English translation).
Office Action dated Feb. 24, 2014, in Eurasian Patent Application No. 201201264.
Office Action dated Jul. 11, 2017, in Mexican Patent Application No. MX/a/2015/013118 (with English translation).
Office Action dated Jul. 18, 2016, in Indonesian Patent Application No. W00201203610.
Office Action dated Jul. 23, 2015, in Ukrainian Patent Application No. 201211548.
Office Action dated Jul. 3, 2017, in Mexican Patent Application No. MX/a/2015/012632 (with English translation).
Office Action dated Jul. 30, 2018, in Canadian Patent Application No. 2,848,576.
Office Action dated Jul. 6, 2017, in Mexican Patent Application No. MX/a/2015/013103 (with English translation).
Office Action dated Jun. 20, 2016, in Chinese Patent Application No. 201280054819.5.
Office Action dated Jun. 24, 2016, in Chinese Patent Application No. 201280053984.9.
Office Action dated Mar. 16, 2017, in Chinese Patent Application No. 201280054819.5.
Office Action dated Mar. 8, 2018 (with English translation), in Chilean Patent Application No. 201403192.
Office Action dated May 3, 2016, in Chilean Patent Application No. 201601057.
Office Action dated Nov. 15, 2016, in Mexican Patent Application No. MX/a/2014/003068 (with English translation).
Office Action dated Sep. 20, 2018, in Chilean Patent Application No. 201601440 (with English translation).
Office Action dated Sep. 5, 2016, in Ukrainian Patent Application No. a 2014 03846.
Office Action dated Sep. 6, 2017, in Chinese Patent Application No. 2014800154012 (with English translation).
Office Action dated Nov. 3, 2014, in Chinese Patent Application No. 201180012795.2.
Office Action dated Jan. 6, 2015, in Japanese Patent Application No. 2012-557165.
Office Action dated Nov. 19, 2014, in Eurasian Patent Application No. 201201264/28.
Office Action dated Oct. 5, 2015, in Eurasian Patent Application No. 201201264/28.
Ongvarrasopone et al., "A Simple and Cost Effective Method to Generate dsRNA for RNAi Studies in Invertebrates," Science Asia, 33:35-39 (2007).
Orbović et al., "Foliar-Applied Surfactants and Urea Temporarily Reduce Carbon Assimilation of Grapefruit Leaves," J. Amer. Soc. Hort. Sci., 126(4):486-490 (2001).
Ouellet et al., "Members of the Acetohydroxyacid Synthase Muligene Family of *Brassica napus* Have Divergent Patterns of Expression," The Plant Journal, Blackwell Scientific Publications, Oxford, GB, 2(3):321-330 (1992).
Paddison et al., "Stable suppression of gene expression by RNAi in mammalian cells," Proc. Natl Acad. Sci. USA, 99(3):1443-1448 (2002).
Palauqui et al., "Activation of systemic acquired silencing by localised introduction of DNA," Current Biology, 9:59-66 (1999).
Parera et al., "Dehydration Rate after Solid Matrix Priming Alters Seed Performance of Shrunken-2 Corn," J. Amer. Soc. Hort. Sci., 119(3):629-635 (1994).
Partial European Search Report dated Jun. 29, 2018, in European Patent Application No. 18157745.3.
Partial European Search Report dated Dec. 6, 2017, in European Patent Application No. 17181861.0.
Partial Supplementary European Search Report dated Jan. 11, 2018, in European Patent Application No. 15812530.2.
Partial Supplementary European Search Report dated Mar. 2, 2015, in European Patent Application No. 12 831 494.5.
Partial Supplementary European Search Report dated Jan. 11, 2018, in European Patent Application No. 15812530.0.
Patent Examination Report No. 1 dated Feb. 8, 2016, in Australian Patent Application No. 2014262189.
Patent Examination Report No. 1 dated Jun. 17, 2016, in Australian Patent Application No. 2012308659.
Patent Examination Report No. 1 dated Jun. 17, 2016, in Australian Patent Application No. 2012308660.
Patent Examination Report No. 1 dated Jun. 8, 2017, in Australian Patent Application No. 2012308686.
Patent Examination Report No. 1 dated Nov. 11, 2013, in Australian Patent Application No. 2011224570.
Paungfoo-Lonhienne et al., "DNA is Taken up by Root Hairs and Pollen, and Stimulates Root and Pollen Tube Growth," Plant Physiology, 153:799-805 (2010).
Paungfoo-Lonhienne et al., "DNA uptake by *Arabidopsis* induces changes in the expression of CLE peptides which control root morphology," Plant Signaling & Behavior, 5(9):1112-1114 (2010).
Pei et al., "On the art of identifying effective and specific siRNAs," Nature Methods, 3(9):670-676 (2006).
Peretz et al., "A Universal Expression/Silencing Vector in Plants," Plant Physiology, 145:1251-1263 (2007).
Pornprom et al., "Glutamine synthetase mutation conferring target-site-based resistance to glufosinate in soybean cell selections," Pest Manag Sci, 2009; 65(2):216-222 (2009).
Powles et al., "Evolution in Action: Plants Resistant to Herbicides," Annual Review of Plant Biology, 61(1):317-347 (2010).

(56) References Cited

OTHER PUBLICATIONS

Pratt et al., "Sorghum Expressed Sequence Tags Identify Signature Genes for Drought, Pathogenesis, and Skotomorphogenesis from a Milestone Set of 16,801 Unique Transcripts," Plant Physiology, 139:869-884 (2005).
Pratt et al., "Amaranthus rudis and A. tuberculatus, One Species or Two?," Journal of the Torrey Botanical Society, 128(3):282-296 (2001).
Preston et al., "Multiple effects of a naturally occurring proline to threonine substitution within acetolactate synthase in two herbicide-resistant populations of Lactuca serriola," Pesticide Biochem. Physiol., 84(3):227-235 (2006).
Promoter Prediction for SEQ ID No. 1702 from 13/612929/MK/, Promoter 2.0 Prediction Results, pp. 1-4 (2016).
Promoter Prediction for SEQ ID No. 4 from 13/612995/MK/, Promoter 2.0 Prediction Results, pp. 1-3 (2016).
Promoter Prediction for SEQ ID No. 7 from 13/612936/Mk/, Promoter 2.0 Prediction Results, pp. 1-2 (2016).
Promoter Prediction for SEQ ID No. 8 from 13/612,925/MK/, Promoter 2.0 Prediction Results, pp. 1-6 (2016).
Qiwei, "Advance in DNA interference," Progress in Veterinary Medicine, 30(1):71-75 (2009).
Rajur et al., "Covalent Protein-Oligonucleotide Conjugates for Efficient Delivery of Antisense Molecules," Bioconjug Chem., 8:935-940 (1997).
Rakoczy-Trojanowska, "Alternative Methods of Plant Transformation—a short review," Cellular & Molecular Biology Letters, 7:849-858 (2002).
Reddy et al "Organosilicone Adjuvants Increased the Efficacy of Glyphosate for Control of Weeds in Citrus (*Citrus* spp.)" HortScience 27(9):1003-1005 (1992).
Reddy et al., "Aminomethylphosphonic Acid Accumulation in Plant Species Treated with Glyphosate," J. Agric. Food Chem., 56(6):2125-2130 (2008).
Regalado, "The Next Great GMO Debate," MIT Technology Review,pp. 1-19 (2015) <https://www.technologyreview.com/s/540136/the-next-great-gmo-debate/>.
Reither et al., "Specificity of DNA triple helix formation analyzed by a FRET assay," BMC Biochemistry, 3:27 (2002).
Restriction Requirement dated Apr. 21, 2015, in U.S. Appl. No. 13/612,954.
Restriction Requirement dated Feb. 12, 2015, in U.S. Appl. No. 13/612,985.
Restriction Requirement dated Jul. 15, 2016, in U.S. Appl. No. 14/143,748.
Restriction Requirement dated Jul. 18, 2016, in U.S. Appl. No. 14/143,836.
Restriction Requirement dated Mar. 12, 2015, in U.S. Appl. No. 13/612,948.
Restriction Requirement dated Mar. 4, 2015, in U.S. Appl. No. 13/612,941.
Restriction Requirement dated May 4, 2015, in U.S. Appl. No. 13/612,929.
Restriction Requirement dated May 5, 2015, in U.S. Appl. No. 13/612,936.
Restriction Requirement dated May 7, 2015, in U.S. Appl. No. 13/612,925.
Restriction Requirement dated May 7, 2015, in U.S. Appl. No. 13/612,995.
Restriction Requirement dated Oct. 13, 2016, in U.S. Appl. No. 14/206,707.
Restriction Requirement dated Oct. 2, 2012, in U.S. Appl. No. 13/042,856.
Restriction Requirement dated Oct. 21, 2014, in U.S. Appl. No. 13/583,302.
Restriction Requirement dated Oct. 28, 2015, in U.S. Appl. No. 14/603,347.
Restriction Requirement dated Sep. 2, 2015, in U.S. Appl. No. 14/532,596.
Reverdatto et al., "A Multisubunit Acetyl Coenzyme A Carboxylase from Soybean," Plant Physiol., 119: 961-978 (1999).
Rey et al., "Diversity of Dicotyledenous-Infecting Geminiviruses and Their Associated DNA Molecules in Southern Africa, Including the South-West Indian Ocean Islands," Viruses, 4:1753-1791 (2012).
Reynolds et al., "Rational siRNA design for RNA interference," Nature Biotechnology, 22:326-330 (2004).
Richardson et al., "Targeting and assembly of components of the TOC protein import complex at the chloroplast outer envelope membrane," Frontiers in Plant Science, 5:1-14 (2014).
Riggins et al., "Characterization of de novo transcriptome for waterhemp (*Amaranthus tuberculatus*) using GS-FLX 454 pyrosequencing and its application for studies of herbicide target-site genes," Pest Manag. Sci., 66:1042-1052 (2010).
Roberts, "Fast-track applications: The potential for direct delivery of proteins and nucleic acids to plant cells for the discovery of gene function," Plant Methods, 1(12):1-3 (2005).
Robson et al., "Leaf senescence is delayed in maize expressing the Agrobacterium IPT gene under the control of a novel maize senescence-enhanced promoter," Plant Biotechnology Journal, 2:101-112 (2004).
Roitsch et al., "Extracellular invertase: key metabolic enzyme and PR protein," Journal of Experimental Botany, 54(382):513-524 (2003).
Roitsch et al., "Function and regulation of plant invertases: sweet sensations," Trades in Plant Science, 9(12):606-613 (2004).
Rose et al., "Functional polarity is introduced by Dicer processing of short substrate RNAs," Nucleic Acids Research, 33(13):4140-4156 (2005).
Rothnie et al., "Pararetroviruses and Retroviruses: A Comparative Review of Viral Structure and Gene Expression Strategies," Advances in Virus Research, 44:1-67 (1994).
Ruan et al., "Suppression of Sucrose Synthase Gene Expression Represses Cotton Fiber Cell Initiation, Elongation, and Seed Development," The Plant Cell, 15:952-964 (2003).
Ryabov et al., "Cell-to-Cell, but Not Long-Distance, Spread of RNA Silencing That Is Induced in Individual Epidermal Cells," Journal of Virology, 78(6):3149-3154 (2004).
Ryan, "Human endogenous retroviruses in health and disease: a symbiotic perspective," Journal of the Royal Society of Medicine, 97:560-565 (2004).
Salanenka et al., "Seedcoat Permeability: Uptake and Post-germination Transport of Applied Model Tracer Compounds," HortScience, 46(4):622-626 (2011) Herewith.
Sammataro et al., "Some Volatile Plant Oils as Potential Control Agents for Varroa Mites (Acari: Varroidae) in Honey Bee Colonies (Hymenoptera: Apidae)," American Bee Journal, 138(9):681-685 (1998).
Santoro et al., "A general purpose RNA-cleaving DNA enzyme," Proc. Natl. Acad. Sci. USA, 94:4262-4266 (1997).
Sathasivan et al., "Nucleotide sequence of a mutant acetolactate synthase gene from an imidazolinone-resistant *Arabidopsis thaliana* var. Columbia," Nucleic Acids Research, 18(8):2188-2193 (1990).
Schönherr et al., "Size selectivity of aqueous pores in astomatous cuticular membranes isolated from Populus canescens (Aiton) Sm. Leaves," Planta, Herewith. 219:405-411 (2004).
Schönherr, "Water Permeability of Isolated Cuticular Membranes: The Effect of pH and Cations on Diffusion, Hydrodynamic Permeability and Size of Polar Pores in the Cutin Matrix," Planta, 128:113-126 (1976).
Schwab et al., "RNA silencing amplification in plants: Size matters," PNAS, 107(34):14945-14946 (2010).
Schweizer et al., "Double-stranded RNA interferes with gene function at the single-cell level in cereals," The Plant Journal, 24(6):895-903 (2000) Herewith..
Schwember et al., "Drying Rates following Priming Affect Temperature Sensitivity of Germination and Longevity of Lettuce Seeds," HortScience, 40(3):778-781 (2005).
Scott et al., Botanical Insecticides for Controlling Agricultural Pests: Piperamides and the Colorado Potato Beetle *Leptinotarsa decemlineata* Say (Coleoptera: Chrysomelidae), Archives of Insect Biochemistry and Physiology, 54:212-225 (2003).

(56) References Cited

OTHER PUBLICATIONS

Search Report dated Jul. 24, 2017, in Chinese Patent Application No. 201480014392.5 (with English translation).
Search Report dated Oct. 20, 2017, in Chinese Patent Application No. 201380039346.6.
Second Chinese Office Action dated Jun. 10, 2014, in Chinese Patent Application No. 201180012795.2.
Second Office Action dated Feb. 25, 2016, in Chinese Patent Application No. 201280054179.8.
Second Office Action dated Mar. 4, 2016, in Chinese Patent Application No. 201280054820.8.
Seidman et al., "The potential for gene repair via triple helix formation," J Clin Invest., 112(4):487-494 (2003).
Selvarani et al., "Evaluation of seed priming methods to improve seed vigour of onion (*Allium cepa* cv. Aggregatum) and carrot (*Daucus carota*)," Journal of Agricultural Technology, 7(3):857-867 (2011).
Senthil-Kumar et al., "A systematic study to determine the extent of gene silencing in Nicotiana benthamiana and other *Solanaceae* species when heterologous gene sequences are used for virus-induced gene silencing," New Phytologist, 176:782-791 (2007).
Sharma et al., "A simple and efficient Agrobacterium-mediated procedure for transformation of tomato," J. Biosci., 34(3):423 433 (2009).
Shintani et al., "Antisense Expression and Overexpression of Biotin Carboxylase in Tobacco Leaves," Plant Physiol., 114:881-886 (1997).
Showalter, "Structure and Function of Plant Cell Wall Proteins," The Plant Cell, 5:9-23 (1993).
Sijen et al. "On the Role of RNA Amplification in dsRNA-Triggered Gene Silencing," Cell, 107:465-476 (2001).
Silwet L-77 Spray Adjuvant for agricultural applications, product description from Momentive Performance Materials, Inc. (2003).
Singh et al., "Absorption and translocation of glyphosate with conventional and organosilicone adjuvants," Weed Biology and Management, 8:104-111 (2008).
Small, "RNAi for revealing and engineering plant gene functions," Current Opinion in Biotechnology, 18:148-153 (2007).
Snead et al., "Molecular basis for improved gene silencing by Dicer substrate interfering RNA compared with other siRNA variants," Nucleic Acids Research, 41(12):6209-6221 (2013).
Song et al., "Herbicide," New Heterocyclic Pesticide, Chemical Industry Press, 354-356 (2011).
Statement of Grounds and Particulars dated Sep. 1, 2017, in Australian Patent No. 2014262189.
Steeves et al., "Transgenic soybeans expressing siRNAs specific to a major sperm protein gene suppress Heterodera glycines reproduction," Funct. Plant Biol., 33:991-999 (2006).
Stevens et al., "New Formulation Technology—Silwet® Organosilicone Surfactants Have Physical and Physiological Properties Which Enhance the Performance of Sprays," Proceedings of the 9th Australian Weeds Conference, pp. 327-331 (1990).
Stevens, "Formulation of Sprays to Improve the Efficacy of Foliar Fertilisers," New Zealand Journal of Forestry Science, pp. 24(1):27-34 (1994).
Stevens, "Organosilicone Surfactants as Adjuvants for Agrochemicals," Journal of Pesticide Science, 38:103-122 (1993).
Stock et al., "Possible Mechanisms for Surfactant-Induced Foliar Uptake of Agrochemicals," Pestic. Sci., 38:165-177 (1993).
Strat et al., "Specific and nontoxic silencing in mammalian cells with expressed long dsRNAs," Nucleic Acids Research, 34(13):3803-3810 (2006).
Street "Why is DNA (and not RNA) a stable storage form for genetic information?," Biochemistry Revisited, pp. 1-4 (2008).
Sudarsan et al., "Metabolite-binding RNA domains are present in the genes of eukaryotes," RNA, 9:644-647 (2003).
Summons to Attend Oral Proceedings Pursuant to Rule 115(1) EPC, dated Aug. 7, 2017, in European Patent Application No. 12832160.1.

Sun et al., "A Highly efficient Transformation Protocol for Micro-Tom, a Model Cultivar for Tomato Functional Genomics," Plant Cell Physiol., 47(3):426-431 (2006).
Sun et al., "Antisense oligodeoxynucleotide inhibition as a potent strategy in plant biology: identification of SUSIBA2 as a transcriptional activator in plant sugar signalling," The Plant Journal, 44:128-138 (2005).
Sun et al., "Sweet delivery—sugar translocators as ports of entry for antisense oligodeoxynucleotides in plant cells," The Plant Journal, 52:1192-1198 (2007).
Sun, "Characterization of Organosilicone Surfactants and Their Effects on Sulfonylurea Herbicide Activity," Thesis Submitted to the Faculty of the Virginia Polytechnic Institute and State University dated Apr. 5, 1996.
Sutton et al., "Activity of mesotrione on resistant weeds in maize," Pest Manag. Sci., 58:981-984 (2002).
Takasaki et al., "An Effective Method for Selecting siRNA Target Sequences in Mammalian Cells," Cell Cycle, 3:790-795 (2004).
Tang et al., "Efficient delivery of small interfering RNA to plant cells by a nanosecond pulsed laser-induced stress wave for post-transcriptional gene silencing," Plant Science, 171:375-381 (2006).
Tank Mixing Chemicals Applied to Peanut Crops: Are the Chemicals Compatible?, College of Agriculture & Life Sciences, NC State University, AGW-653, pp. 1-11 (2004).
Taylor, "Seed Storage, Germination and Quality," The Physiology of Vegetable Crops, pp. 1-36 (1997).
Temple et al., "Can glutamine synthetase activity levels be modulated in transgenic plants by the use of recombinant DNA technology?" Transgenic Plants and Plant Biochemistry, 22(4):915-920 (1994).
Temple et al., "Down-regulation of specific members of the glutamine synthetase gene family in Alfalfa by antisense RNA technology," Plant Molecular Biology, 37:535-547 (1998).
Templeton et al., "Improved DNA: liposome complexes for increased systemic delivery and gene expression," Nature Biotechnology, 15:647-652 (1997).
Teng et al., "Tic21 Is an Essential Translocon Component for Protein Translocation across the Chloroplast Inner Envelope Membrane," The Plant Cell, 18:2247-2257 (2006).
Tenllado et al., "Crude extracts of bacterially expressed dsRNA can be used to protect plants against virus infections," BMC Biotechnology, 3:1-11 (2003).
Tenllado et al., "Double-Stranded RNA-Mediated Interference with Plant Virus Infection," Journal of Virology, 75(24):12288-12297 (2001).
Tenllado et al., "RNA interference as a new biotechnological tool for the control of virus diseases in plants," Virus Research, 102:85-96 (2004).
Tepfer, "Risk assessment of virus resistant transgenic plants," Annual Review of Phytopathology, 40:467-491 (2002).
The Seed Biology Place, Website Gerhard Leubner Lab Royal Holloway, University of London, <http://www.seedbiology.de/seedtechnology.asp.
Third Party Submission filed on Nov. 29, 2012 in U.S. Appl. No. 13/042,856.
Thomas et al., "Size constraints for targeting post-transcriptional gene silencing and for RNA-directed methylation in Nicotiana benthamiana using a potato virus X vector," The Plant Journal, 25(4):417-425 (2001).
Thompson, et al., "CLUSTAL W: improving the sensitivity of progressive multiple sequence alignment through sequence weighting, position-specific gap penalties and weight matrix choice," Nucl. Acids Res., 22(22):4673-4680 (1994).
Tice, "Selecting the right compounds for screening: does Lipinski's Rule of 5 for pharmaceuticals apply to agrochemicals?," Pest Management Science, 57(1):3-16 (2001).
Timmons et al., "Specific interference by ingested dsRNA," Nature, 395:854 (1998).
Tomari et al., "Perspective: machines for RNAi," Genes & Dev., 19:517-529 (2005).
Tomlinson et al., "Evidence that the hexose-to-sucrose ratio does not control the switch to storage product accumulation in oilseeds:

(56) References Cited

OTHER PUBLICATIONS analysis of tobacco seed development and effects of overexpressing apoplastic invertase," Journal of Experimental Botany, 55(406):2291-2303 (2004).
Töpfer et al., "Uptake and Transient Expression of Chimeric Genes in Seed-Derived Embryos," Plant Cell, 1:133-139 (1989).
Toriyama et al., "Transgenic Rice Plants After Direct Gene Transfer Into Protoplasts," Bio/Technology, 6:1072-1074 (1988).
Tran et al., "Control of specific gene expression in mammalian cells by co-expression of long complementary RNAs," FEBS Lett.;573(1-3):127-134 (2004).
Tranel et al., "Resistance of weeds to ALS-inhibiting herbicides: what have we learned?," Weed Science, 50:700-712 (2002).
Trucco et al., "Amaranthus hybridus can be pollinated frequently by A. tuberculatus under filed conditions," Heredity, 94:64-70 (2005).
Tsugawa et al., "Efficient transformation of rice protoplasts mediated by a synthetic polycationic amino polymer," Theor Appl Genet, 97:1019-1026 (1998).
Turina et al., "Tospoviruses in the Mediterranean Area," Advances in Virus Research, 84:403-437 (2012).
Tuschl, "Expanding small RNA interference," Nature Biotechnol., 20: 446-448 (2002).
Tuschl, "RNA Interference and Small Interfering RNAs," ChemBiochem. 2(4):239-245 (2001).
Ui-Tei et al., "Guidelines for the selection of highly effective siRNA sequences for mammalian and chick RNA interference," Nucleic Acids Res., 32(3): 936-948 (2004).
Ulrich et al., "Large scale RNAi screen in Tribolium reveals novel target genes for pest control and the proteasome as prime target," BMC genomics, 16(1):671 (2015).
Unnamalai et al., "Cationic oligopeptide-mediated delivery of dsRNA for post-transcriptional gene silencing in plant cells," FEBS Letters, 566:307-310 (2004).
Unniraman et al., "Alternate Paradigm for Intrinsic Transcription Termination in Eubacteria," The Journal of Biological Chemistry, 276(45)(9):41850-41855 (2001).
Unniraman et al., "Conserved Economics of Transcription Termination in Eubacteria," Nucleic Acids Research, 30(3):675-684 (2002).
Urayama et al., "Knock-down of OsDCL2 in Rice Negatively Affects Maintenance of the Endogenous dsRNA Virus, Oryza sativa Endornavirus," Plant and Cell Physiology, 51(1):58-67 (2010).
Van de Wetering et al., "Specific inhibition of gene expression using a stably integrated, inducible small-interfering-RNA vector," EMBO Rep., 4(6):609-615 (2003).
Vasil et al., "Herbicide Resistant Fertile Transgenic Wheat Plants Obtained by Microprojectile Bombardment of Regenerable Embryogenic Callus," Bio/Technology,10:667-674 (1992).
Vaucheret, "Post-transcriptional small RNA pathways in plants: mechanisms and regulations," Genes Dev., 20:759-771 (2006).
Vencill et al., "Resistance of Weeds to Herbicides," Herbicides and Environment, 29:585-594 (2011).
Verma et al., "Modified oligonucleotides: synthesis and strategy for users," Annu. Rev. Biochem., 67:99-134 (1998).
Vermeulen et al., "The contributions of dsRNA structure to Dicer specificity and efficiency," RNA, 11(5):674-682 (2005).
Vert et al., "An accurate and interpretable model for siRNA efficacy prediction," BMC Bioinformatics, 7:520 (2006).
Voinnet et al., "Systemic Spread of Sequence-Specific Transgene RNA Degradation in Plants Is Initiated by Localized Introduction of Ectopic Promoterless DNA," Cell, 95:177-187 (1998).
Voinnet, "Origin, Biogenesis, and Activity of Plant MicroRNAs," Cell, 136:669-687 (2009).
Wakelin et al., "A target-site mutation is present in a glyphosate-resistant Lolium rigidum population," Weed Res. (Oxford), 46(5):432-440 (2006).
Walton et al., "Prediction of antisense oligonucleotide binding affinity to a structured RNA target," Biotechnol Bioeng 65(1):1-9 (1999).
Wan et al., "Generation of Large Numbers of Independently Transformed Fertile Barley Plants," Plant Physiol., 104:37-48 (1994).
Wang et al., "Foliar uptake of pesticides-Present status and future challenge," ScienceDirect, 87:1-8 (2007).
Wardell, "Floral Induction of Vegetative Plants Supplied a Purified Fraction of Deoxyribonucleic Acid from Stems of Flowering Plants," Plant Physiol, 60:885-891 (1977).
Wardell, "Floral Activity in Solutions of Deoxyribonucleic Acid Extracted from Tobacco Stems," Plant Physiol, 57:855-861 (1976).
Waterhouse et al., "Virus resistance and gene silencing in plants can be induced by simultaneous expression of sense and antisense RNA," Proc Natl Acad Sci USA, 95 13959-13964 (1998).
Welch et al., "Expression of ribozymes in gene transfer systems to modulate target RNA levels," Curr Opin Biotechnol. 9(5):486-496 (1998).
Widholm et al., "Glyphosate selection of gene amplification in suspension cultures of 3 plant species," Phyisologia Plantarum, 112:540-545 (2001).
Wiesman et al., "Novel cationic vesicle platform derived from vernonia oil for efficient delivery of DNA through plant cuticle membranes," Journal of Biotechnology, 130:85-94 (2007).
Wild Carrot Noxious Weed Control Board (NWCB) of Washington State (2010) <www.nwcb.wa.gov/detail.asp?weed=46>.
Wilson, et al., "Transcription termination at intrinsic terminators: The role of the RNA hairpin," Proc. Natl. Acad. Sci. USA, 92:8793-8797 (1995).
Winkler et al., "Thiamine derivatives bind messenger RNAs directly to regulate bacterial gene expression," Nature, 419:952-956 (2002).
Wool et al., "Structure and evolution of mammalian ribosomal proteins," Biochem. Cell Biol., 73:933-947 (1995).
Written Opinion dated Apr. 7, 2016, in Singapore Patent Application No. 201206152-9.
Written Opinion dated Mar. 6, 2017, in Singaporean Patent Application No. 2012061529.
Written Opinion dated May 8, 2014, in International Application No. PCT/IL2013/050447.
Written Opinion dated Sep. 1, 2014, in Singapore Patent Application No. 201206152-9.
Xu et al "Characterization and Functional Analysis of the Calmodulin-Binding Domain of Rac1 GTPase," PLoS One, 7(8):e42975 (2012).
Yin et al., "Production of double-stranded RNA for interference with TMV infection utilizing a bacterial prokaryotic expression system," Appl. Microbiol. Biotechnol., 84(2):323-333 (2009).
YouTube video by General Electric Company "Silwet Surfactants," screen shot taken on Jan. 11, 2012 of video of www.youtube.com/watch?v=WBw7nXMqHk8 (uploaded Jul. 13, 2009).
Yu et al., "Diversity of Acetyl-Coenzyme A Carboxylase Mutations in Resistant Lolium Populations: Evaluation Using Clethodim," Plant Physiology, 145:547-558 (2007).
Yu et al., "Glyphosate, paraquat and ACCase multiple herbicide resistance evolved in a Lolium rigidum biotype," Planta, 225:499-513 (2007).
Zabkiewicz, "Adjuvants and herbicidal efficacy—present status and future prospects," Weed Research, 40:139-149 (2000).
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," PNAS, 98(12):6617-6622 (2001).
Zhang et al., "Development and Validation of Endogenous Reference Genes for Expression Profiling of Medaka (*Oryzias latipes*) Exposed to Endocrine Disrupting Chemicals by Quantitative Real-Time RT-PCR," Toxicological Sciences, 95(2):356-368 (2007).
Zhang et al., "Progress in research of honey bee mite Varro destructor," Journal of Environmental Entomology, 34(3):345-353 (2012).
Zhang et al., "A novel rice gene, NRR responds to macronutrient deficiency and regulates root growth," Mol Plant, 5(1):63-72 (2012).
Zhang et al., "Agrobacterium-mediated transformation of *Arabidopsis thaliana* using the floral dip method," Nature Protocols, 1(2):1-6 (2006).
Zhang et al., "Cationic lipids and polymers mediated vectors for delivery of siRNA," Journal of Controlled Release, 123:1-10 (2007).

(56) References Cited

OTHER PUBLICATIONS

Zhang et al., "DEG: a database of essential genes," Nucleic Acids Res., 32:D271-D272 (2004).
Zhang et al., "Transgenic rice plants produced by electroporation-mediated plasmid uptake into protoplasts," The Plant Cell Rep., 7:379-384 (1988).
Zhang, "Artificial trans-acting small interfering RNA: a tool for plant biology study and crop improvements," Planta, 239:1139-1146 (2014).
Zhang, Chapter 10: New Characteristics of Pesticide Research & Development, p. 209 (2010).
Zhao et al., "Ps0r1, a potential target for RNA interference-based pest management," Insect Molecular Biology, 20(1):97-104 (2011).
Zhao et al., "Phyllotreta striolata (Coleoptera: Chrysomelidae): Arginine kinase cloning and RNAi-based pest control," European Journal of Entomology, 105(5):815-822 (2008).
Zhao et al., "Vegetable Statdardized Production Technology," Hangzhou: Zhejiang Science and Technology Press, p. 19 (2008).
Zhong et al., "A forward genetic screen to explore chloroplast protein import in vivo identifies Moco sulfurase, pivotal for ABA and IAA biosynthesis and purine turnover," The Plant Journal, 63:44-59 (2010).
Zhong et al., "A pea antisense gene for the peptidase yields seedling lethals in *Arabidopsis*: chloroplast stromal processing survivors show defective GFP (2003) import in vivo," The Plant Journal, 34:802-812.
Zhu et al., "Ingested RNA interference for managing the populations of the Colorado potato beetle, *Leptinotarsa decemlineata*," Pest Manag Sci, 67:175-182 (2010).
Zotti et al., "RNAi technology for insect management and protection of beneficial insects from diseases: lessons, challenges and risk assessments," Neotropical Entomology, 44(3):197-213 (2015).
Communication pursuant to Article 94(3) EPC dated Mar. 16, 2020, in European Patent Application No. 17194281.6.
Communication pursuant to Article 94(3) EPC dated Mar. 27, 2020, in European Patent Application No. 15811092.4.
Cong et al., "Multiplex Genome Engineering Using CRISPR/Cas Systems," Science, 339:819-823 (2013).
Danka et al., "Field Test of Resistance to Acarapis woodi (Acari: Tarsonemidae) and of Colony Production by Four Stocks of Honey Bees (Hymenoptera: Apidae)," Journal of Economic Entomology, 88(3):584-591 (1995).
De Block et al., "Engineering herbicide resistance in plants by expression of a detoxifying enzyme," EMBO J., 6(9):2513-2519 (1987).
Decision to Grant dated Feb. 24, 2020, in Ukrainian Patent Application No. a 2016 08743 (with English language translation).
Declaration of Professor Robert James Henry executed Mar. 1, 2018, as filed by Applicant in Australian Patent Application No. 2014262189, pp. 1-119.
Drobyazko, "Reliable and environmentally friendly insecticide," *Protection and quarantine of plants*, pp. 52-53 (2012) (with English language translation).
Extended European Search Report dated Mar. 25, 2020, in European Patent Application No. 19192942.1.
Gao et al., "DNA-guided genome editing using the Natronobacterium gregoryi Argonaute," Nature Biotechnology, 34(7):768-773 (2016).
Horsch et al., "Inheritance of Functional Foreign Genes in Plants," Science, 223:496-498 (1984).
Hsu et al., "DNA targeting specificity of RNA-guided Cas9 nucleases," Nature Biotechnology, 31:827-832 (2013).
Hwa et al., "Fixation of hybrid vigor in rice: opportunities and challenges," Euphytica, 160:287-293 (2008).
International Search Report dated Oct. 13, 2016, in International Patent Application No. PCT/US2016/35500.
Jasieniuk et al., "Glyphosate-Resistant Italian Ryegrass (*Lolium multiflorum*) in California: Distribution, Response to Glyphosate, and Molecular Evidence for an Altered Target Enzyme," Weed Science, 56(4):496-502 (2008).

Khanbekova et al., "The defeat of the honey bee *Apis melifera* caucasica Gorb. By viruses and parasites, and condition of bee colonies in different ecogeographical conditions of Greater Caucasus," *Agricultural Biology*. 2013 (p. 43) (with English language translation).
N-TER Nanoparticle siRNA, Sigma Aldrich TM website, Web. 20 Nov 2018 <https://www.sigmaaldrich.com/life-science/custom-oligos/sirna-oligos/n-ter-nanoparticle.html>.
Office Action dated Feb. 20, 2020, in Canadian Patent Application No. 2,905,104.
Office Action dated Feb. 25, 2020, in Japanese Patent Application No. 2017-538699 (with English language translation).
Ossowski et al., "Gene silencing in plants using artificial microRNAs and other small RNAs," *The Plant Journal*, 53:674-690 (2008).
Partial European Search Report dated Dec. 6, 2019, in European Patent Application No. 19185431.4.
Prado et al., "Design and optimization of degenerated universal primers for the doing of the plant acetolactate synthase conserved domains," Weed Science, 52:487-491 (2004).
Qi et al., "RNA processing enables predictable programming of gene expression," Nature Biotechnology, 30:1002-1007 (2012).
Riar et al., "Glyphosate Resistance in a Johnsongrass (*Sorghum halepense*) Biotype from Arkansas," Weed Science, 59:299-304 (2011).
Simeoni et al., "Insight into the mechanism of the peptide-based gene delivery system MPG: implications for delivery of siRNA into mammalian cells," Nucleic Acids Research, 31(11):2717-2724 (2003).
Subramoni et al., "Lipases as Pathogenicity Factors of Plant Pathogens," Handbook of Hydrocarbon and Lipid Microbiology, 3269-3277 (2010).
Swarts et al., "Argonaute of the archaeon Pyrococcus furiosus is a DNA-guided nuclease that targets cognate DNA," Nucleic Acid Res., 43(10):5120-5129 (2015).
Swarts et al., "DNA-guided DNA interference by a prokaryotic Argonaute," Nature, 507(7491):258-61 (2014).
Townsend et al., "High frequency modification of plant genes using engineered zinc finger nucleases," Nature, 459:442-445 (2009).
TransIT-TKO® Transfection Reagent, Frequently Asked Questions, Web. 2019 <https://www.mirusbio.com/tech-resources/faqs/transit-tko-faqs>.
Van der Meer et al., "Promoted analysis of the chalcone synthase (chs A) gene of Petunia hybrid: a 67 bp promoter region directs flower-specific expression," Plant Mol. Biol., 15:95-109 (1990).
Vila-Aiub et al., "Glyphosate resistance in perennial *Sorghum halepense* (Johnsongrass), endowed by reduced glyphosate translocation and leaf uptake," Pest Manag Sci, 68:430-436 (2012).
Walton, "Deconstructing the Cell Wall," Plant Physiol., 104:1113-1118 (1994).
Wang et al., "Principle and technology of genetic engineering in plants," in Plant genetic engineering principles and techniques, *Beijing: Science Press*, pp. 313-315 (1998).
Watson et al., "RNA silencing platforms in plants," *FEBS Letters*, 579:5982-5987 (2005).
Yan et al., Seed Science, China Agriculture Press, pp. 101-103, Tables 2-37 (2001).
Yibrah et al., "Antisense RNA inhibition of uidA gene expression in transgenic plants: Evidence for interaction between first and second transformation events," Hereditas, 118:273-280 (1993).
Zidack et al., "Promotion of Bacterial Infection of Leaves by an Organosilicone Surfactant: Implications for Biological Weed Control," Biological Control, 2:111-117 (1992).
Zipperian et al., "Silicon Carbide Abrasive Grinding," *Quality Matters Newsletter*, PACE Technologies 1(2):1-3 (2002).
Gary, D. J. et al. (Aug. 16, 2007). "Polymer-based SiRNA Delivery: Perspectives on the Fundamental and Phenomenological Distinctions from Polymer-based DNA Delivery," Journal of Controlled Release 121(1-2):64-73.

* cited by examiner

Leaf infiltration with trigger/polybrene/MM400 formulation

Infiltrated leaf tissue collected for analysis (20 HAT)

Expected sliced fragment: ~ 500 nt
KD will be evaluated by QG or qPCR

Trigger Delivery in 16c Plant – Leaf Infiltration of Trigger/Polyb/SM400 Formulation

Formulation : polybrene+MMG

Tissue collected: Application leaf

Top leaf

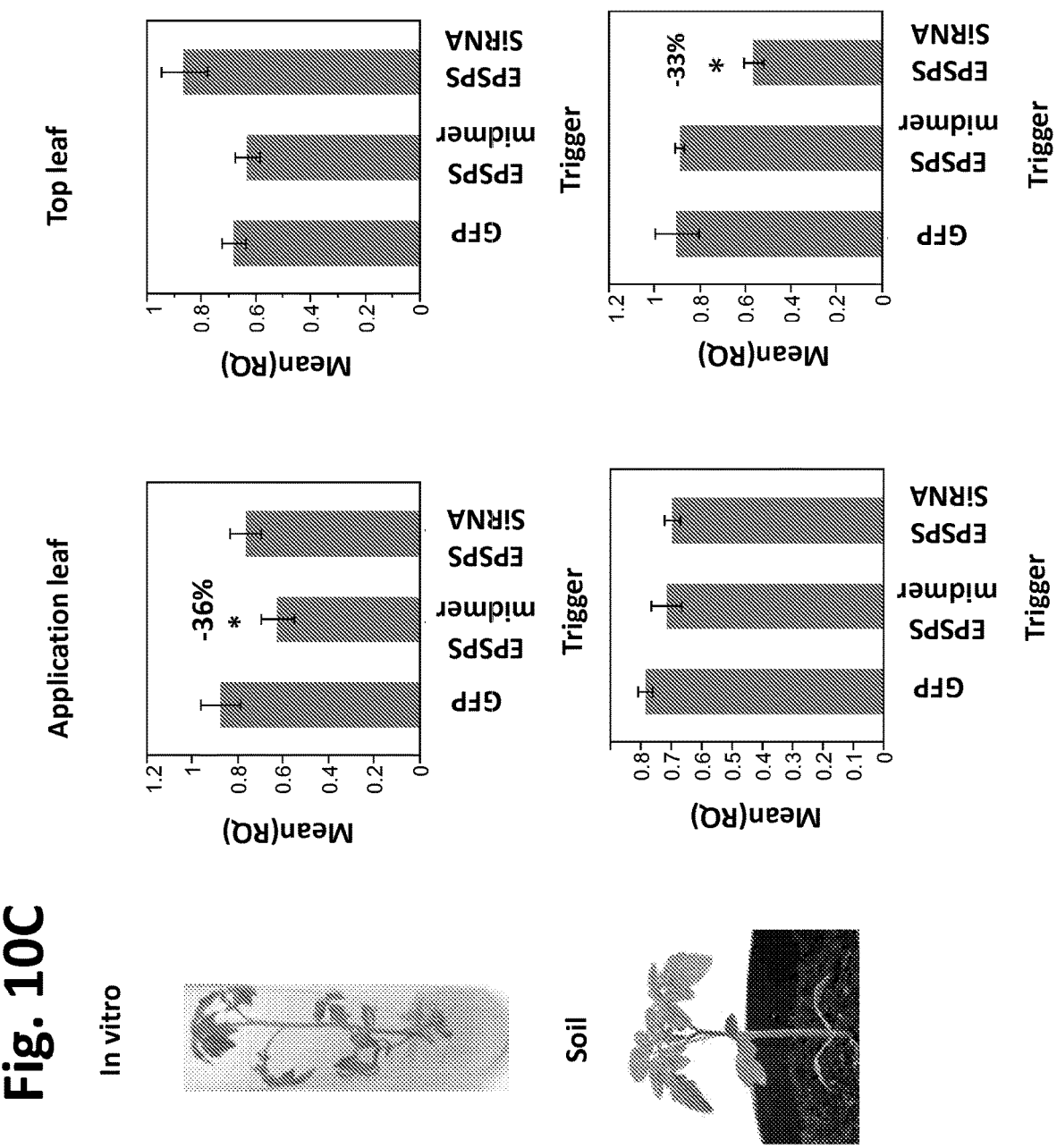

Fig. 11B

| sample: | rep | growth condition | northern blot | | | KD |
|---|---|---|---|---|---|---|
| | | | AL | TL | | |
| EPSPS midmer | 2 | in vitro | Strong band | No | | -40% |
| EPSPS midmer | 3 | in vitro | Weak band | No | | -33% |
| EPSPS midmer | 4 | in vitro | No | No | | 25% |
| EPSPS midmer | 7 | in vitro | No | No | | -35% |
| EPSPS midmer | 8 | in vitro | Strong band | | | -49% |
| GFP | 2 | in vitro | negative control | | | |
| GFP | 3 | in vitro | negative control | | | |
| GFP | 4 | in vitro | negative control | | | |
| EPSPS midmer | 1 | soil | No band | | | -20% |
| EPSPS midmer | 2 | soil | No band | | | -8% |
| EPSPS midmer | 3 | soil | No band | | | -7% |
| EPSPS midmer | 4 | soil | No band | | | -19% |
| EPSPS midmer | 5 | soil | No band | | | 14% |

| Promoter | Origin | Expression pattern |
|---|---|---|
| 35S | CaMV | Constitutive expression. High expression in fruits. |
| Lipid Transfer Protein 1 (LTP1) | *Arabidopsis* | Expression primarily in epidermis and vascular tissues; Columella and placental tissue of fruit. |

Trigger

GFP siRNA

GFP midmer

Formulation

| Index | Description | Reps | Vol/pla nt | Total vol | Trig con. | Trig/pla nt | Tot Trig vol | Tot Polyb | H₂O | 2xMMg | Total vol |
|---|---|---|---|---|---|---|---|---|---|---|---|
| 1 | EPSPS/Polyb | 16 | 4 | 64 | 3.6 | 3.5 | 15.56 | 4.2 | 15.44 | 28.8 | 64.00 |
| 2 | LTPGFP21/polyb | 16 | 4 | 64 | 7.15 | 3.5 | 7.83 | 4.2 | 23.17 | 28.8 | 64.00 |
| 3 | LTPGFP48mer/p olyb | 16 | 4 | 64 | 8.17 | 3.5 | 6.85 | 4.2 | 24.15 | 28.8 | 64.00 |

EXPERIMENT 1 (EPSPS) (Celebrity)

EXPERIMENT 2 (EPSPS) (Celebrity)

METHODS AND COMPOSITIONS FOR DELIVERING NUCLEIC ACIDS TO PLANT CELLS AND REGULATING GENE EXPRESSION

CROSS-REFERENCE TO RELATED APPLICATIONS

This application is a U.S. National Stage Application of International Application No. PCT/US2015/037522 filed Jun. 24, 2015, which claims the benefit of U.S. Provisional Application No. 62/017,196, filed Jun. 25, 2014 and U.S. Provisional Application No. 62/072,888, filed Oct. 30, 2014, which are incorporated by reference in their entireties herein.

INCORPORATION OF SEQUENCE LISTING

A computer readable form of a sequence listing is filed with this application by electronic submission and is incorporated into this application by reference in its entirety. The sequence listing is contained in a file named P34162US02_SEQ.txt, which is 14,893 bytes in size (measured in operating system MS windows) and was created on Dec. 23, 2016.

FIELD

The present disclosure provides compositions and methods for the regulation of gene expression through the topical application of nucleic acids via RNA-mediated silencing.

BACKGROUND

Topical application of nucleic acids targeting gene transcripts and/or promoter region has been demonstrated to produce desired phenotypes in different plant species. See, e.g., U.S. patent application Ser. No. 13/042,856. This approach of gene regulation has many advantages over transgene-based conventional RNAi technique in regulation of gene expression in plants. Efficient incorporation of inhibitory nucleic acids into the interior of plant cells is the critical first step of the topical approach. Plants possess multiple barriers to nucleic acid entry, such as the cuticle, cell wall and plasma membrane. It is therefore a challenge to deliver large macromolecules, such as nucleic acids, through intact plant cell walls.

SUMMARY

The present disclosure provides compositions and methods for the regulation of gene expression through the topical application of nucleic acids, e.g., double stranded ribonucleic acid (dsRNA) via RNA-mediated silencing.

The present disclosure provides a method for delivering one or more polynucleotides into a plant cell, comprising applying onto a plant or a part thereof a mixture comprising: a) a cationic polyelectrolyte; and b) the one or more polynucleotides, wherein the one or more polynucleotides comprise at least one segment of 18 or more contiguous nucleotides that shares about 90% to about 100% sequence identity to a fragment of a target gene, or the complement thereof. In some embodiments, an osmolyte is further applied.

The present disclosure also provides a composition for delivering one or more polynucleotides into a plant cell, comprising: a) a cationic polyelectrolyte; and b) the one or more polynucleotides, wherein the one or more polynucleotides comprise at least one segment of 18 or more contiguous nucleotides that shares about 90% to about 100% sequence identity to a fragment of a target gene, or the complement thereof. In some embodiments, the composition further comprises an osmolyte.

In one aspect, the polynucleotide suppresses expression of the target gene. In some embodiments, the target gene encodes a protein that provides resistance to a chemical herbicide, and the mixture or composition further comprises the chemical herbicide.

In some embodiments, the cationic polyelectrolyte is a polymer or a polypeptide. In some embodiments, the osmolyte comprises a carbohydrate or a sugar alcohol. In some embodiments, the mixture or composition further comprises a surfactant. In some embodiments, the mixture or composition further comprises Endoporter.

BRIEF DESCRIPTION OF THE DRAWINGS

FIGS. 10A-10C: Transfection of intact tomato leaves. FIG. 10A illustrates the polynucleotide trigger sequences for EPSPS siRNA (SEQ ID NO:9/SEQ ID NO:10) and EPSPS midmcr (SEQ ID NO:11) used in transfection experiments in intact tomato leaves. FIG. 10B shows the composition of the formulation tested as well as a photo depicting the type and location of the tissue collected. FIG. 10C shows the results of the Quantigene® analysis relative to GFP trigger for EPSPS in both application and top leaves for plants that were grown and treated in vitro or in soil.

FIGS. 11A and 11B: Northern blot analysis of Tomato plants transfected with dsRNA triggers grown either in vitro or in soil. Both application and top leaves were analyzed after transfection. The EPSPS midmcr (lane 8) was detected in both the Application leaf (AL) and Terminal leaf (TL) in the in vitro grown tomato plants where it accounted for a 49% reduction in signal strength. FIG. 11B is a summary table of results presented in FIG. 11A (Northern blot).

FIG. 12A depicts the promoter, species origin and expression pattern for both 35S constitutive promoter and LTP1 (lipid transfer protein 1) promoters. FIG. 12B illustrates the polynucleotide trigger sequences used for transfection, GFPsiRNA (SEQ ID NO:20/SEQ ID NO:21) and GFP midmer (SEQ ID NO:18/SEQ ID NO:19). The lower portion of FIG. 12B illustrates in table format the formulations used for transfection of tomato leaves.

Figure 21:
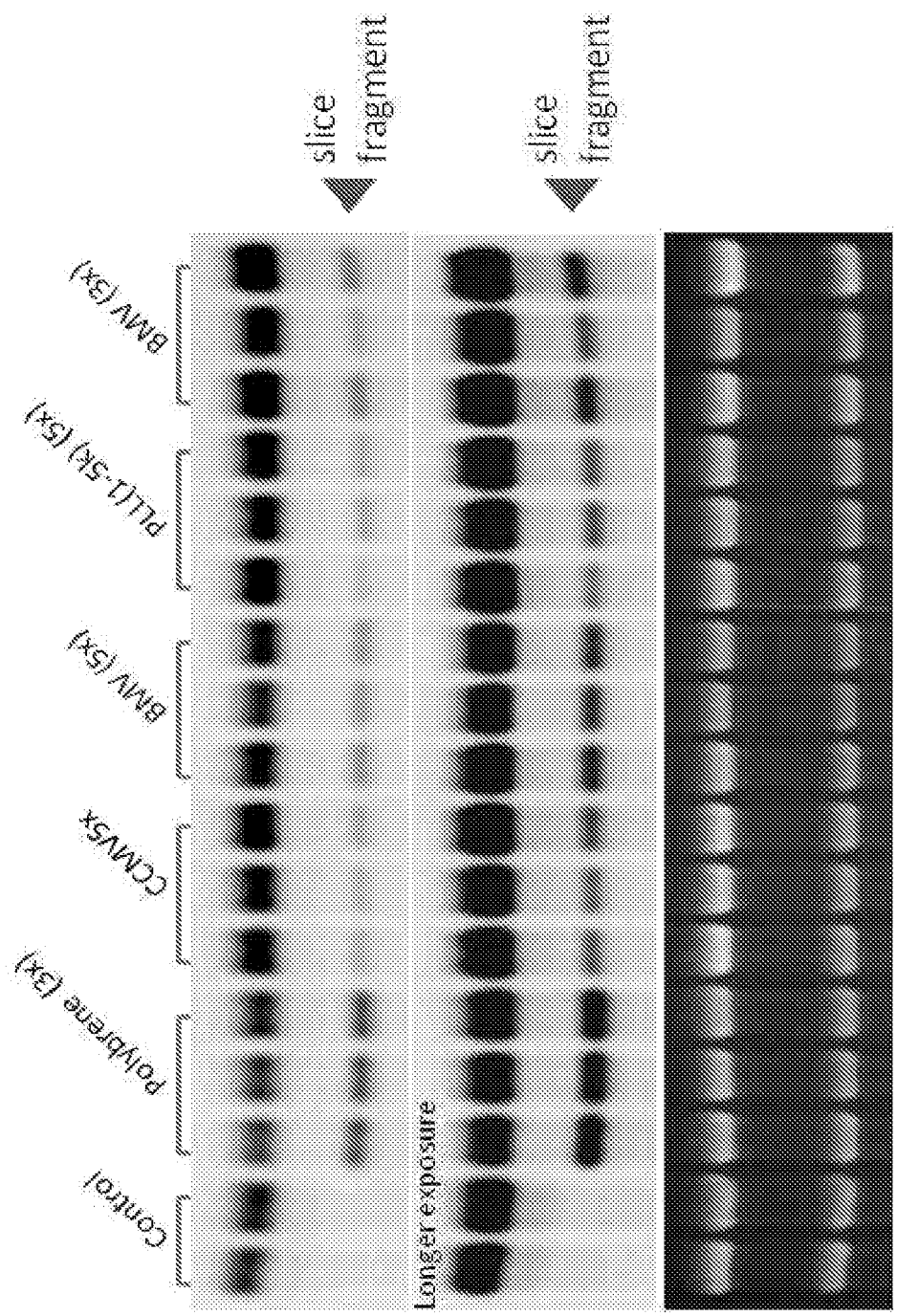

FIG. 21: Northern blot analysis of transfected BY_2 extracts treated with different transfection reagents. Transfections were carried out using the GFP22-3 dsRNA (SEQ ID NO:1/SEQ ID NO:2) in formulations containing Polybrene®, or formulations containing CCMV, BMV, or PLL as outlined in Table 14. A sliced fragment was observed in all formulations tested.

Figure 22:
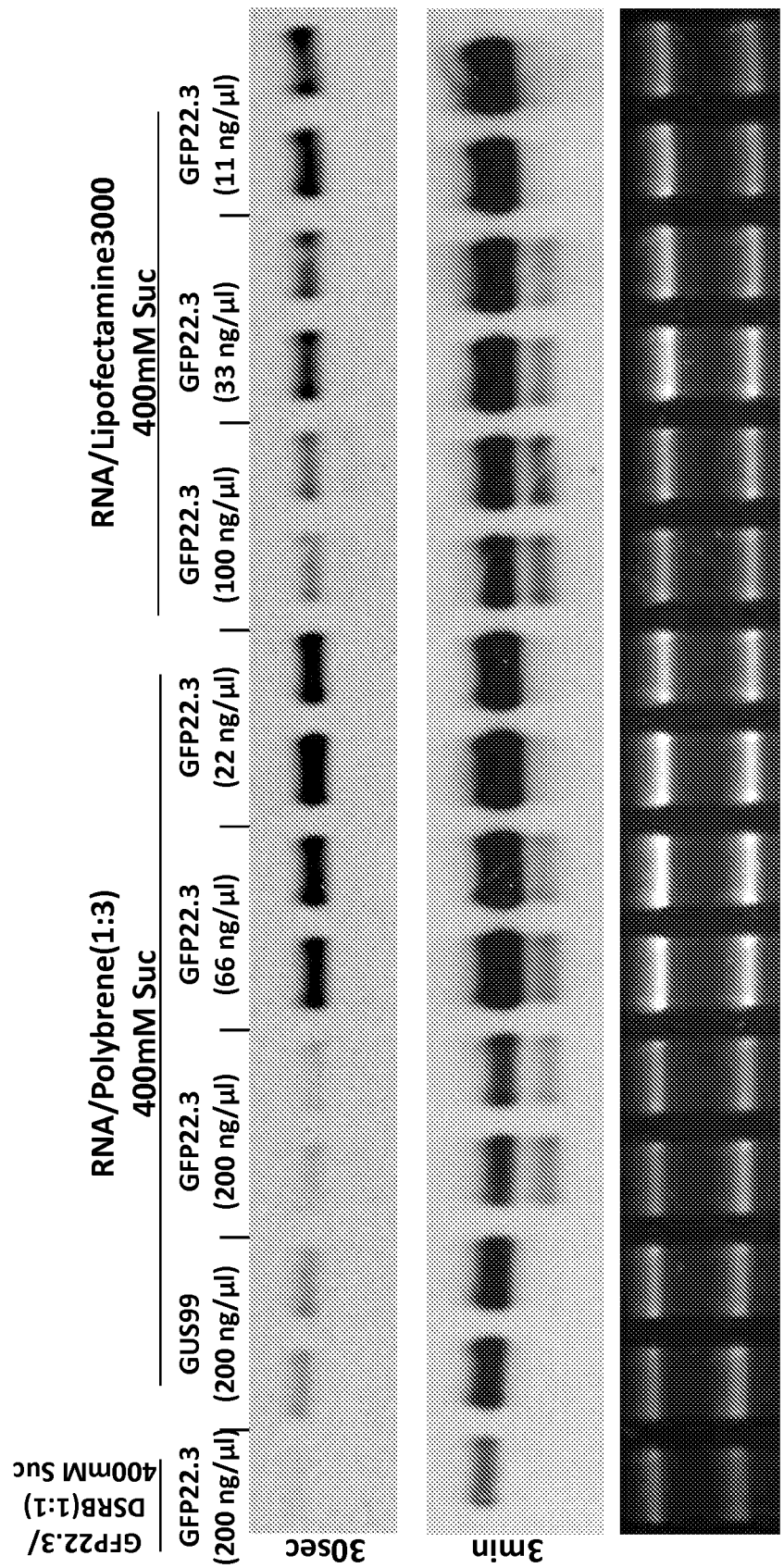

FIG. 22: Northern blot analysis of a transfection comparison of Polybrene® and Lipofectamine® 3000 containing formulation. Cells were transfected with different dsRNAs in formulations containing either Polybrene® or Lipofectamine® 3000 and 400 mM Sucrose.

Figure 23:
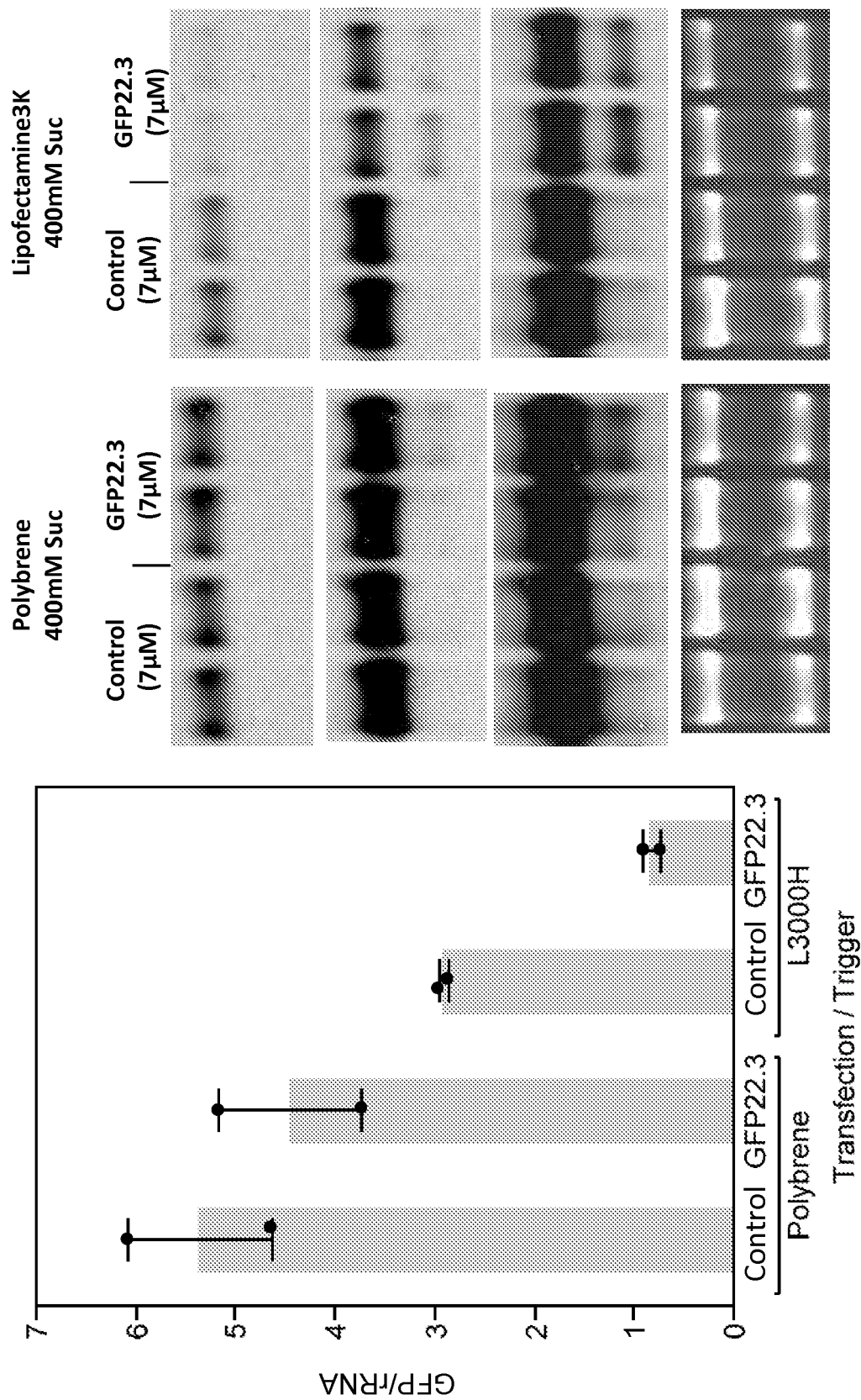

FIG. 23: On the left side of this Figure is the quantification of the RNA levels in extracts treated with the off target control compared to the GFP22-3 dsRNAs in formulations containing either Polybrene® or Lipofectamine® 3000 (L3000H). On the right side of the Figure is the Northern blot analysis of the transfection with different exposures.

Figure 24:
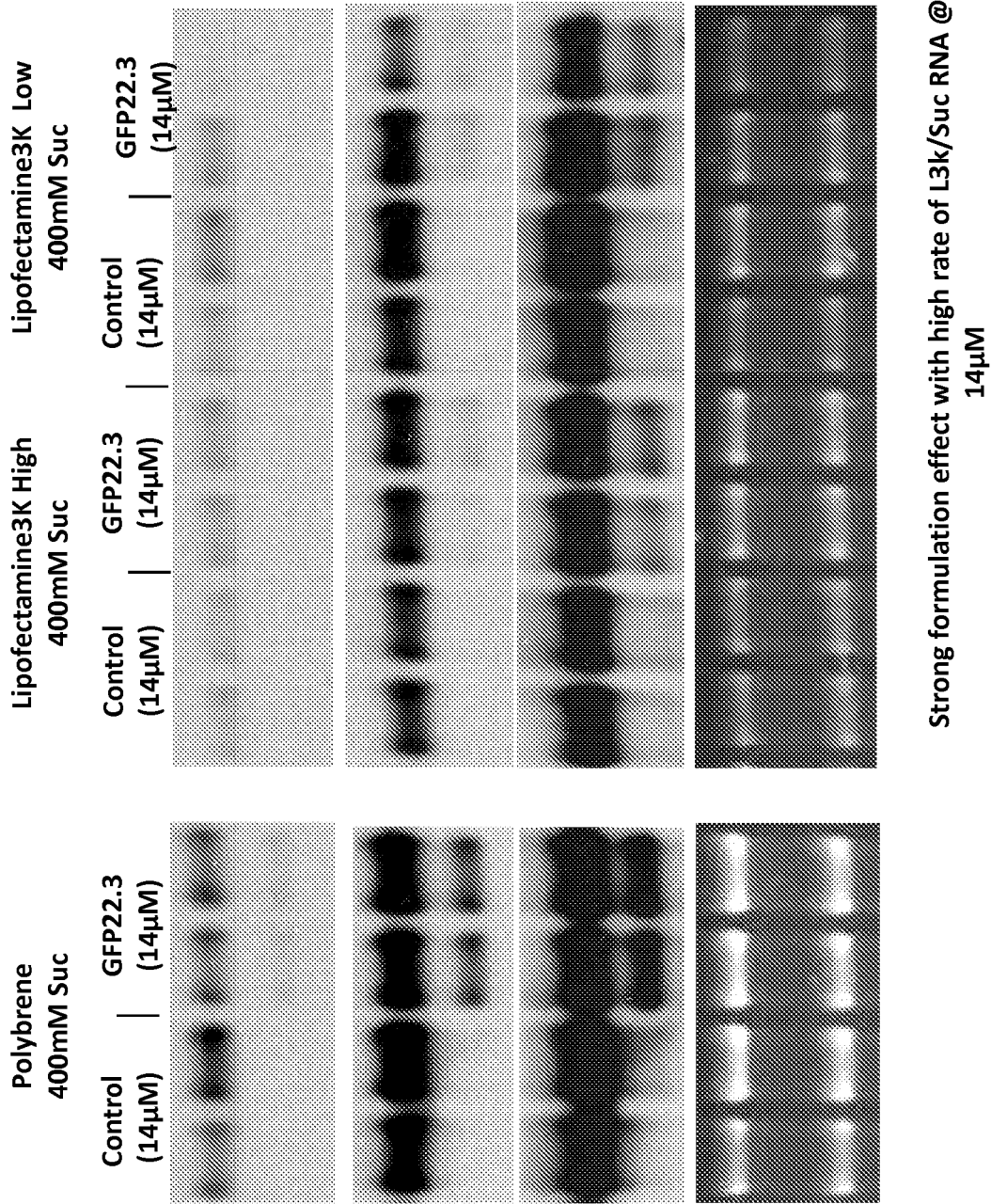

FIG. 24: Northern blot analysis of extracts from BY_2 transfection experiments comparing Polybrene® and Lipofectamine®. L3000 was diluted into SM400 at a rate of 0.75 ("Low") or 1.5 ("High") microliters per microgram of siRNA.

Figure 25:
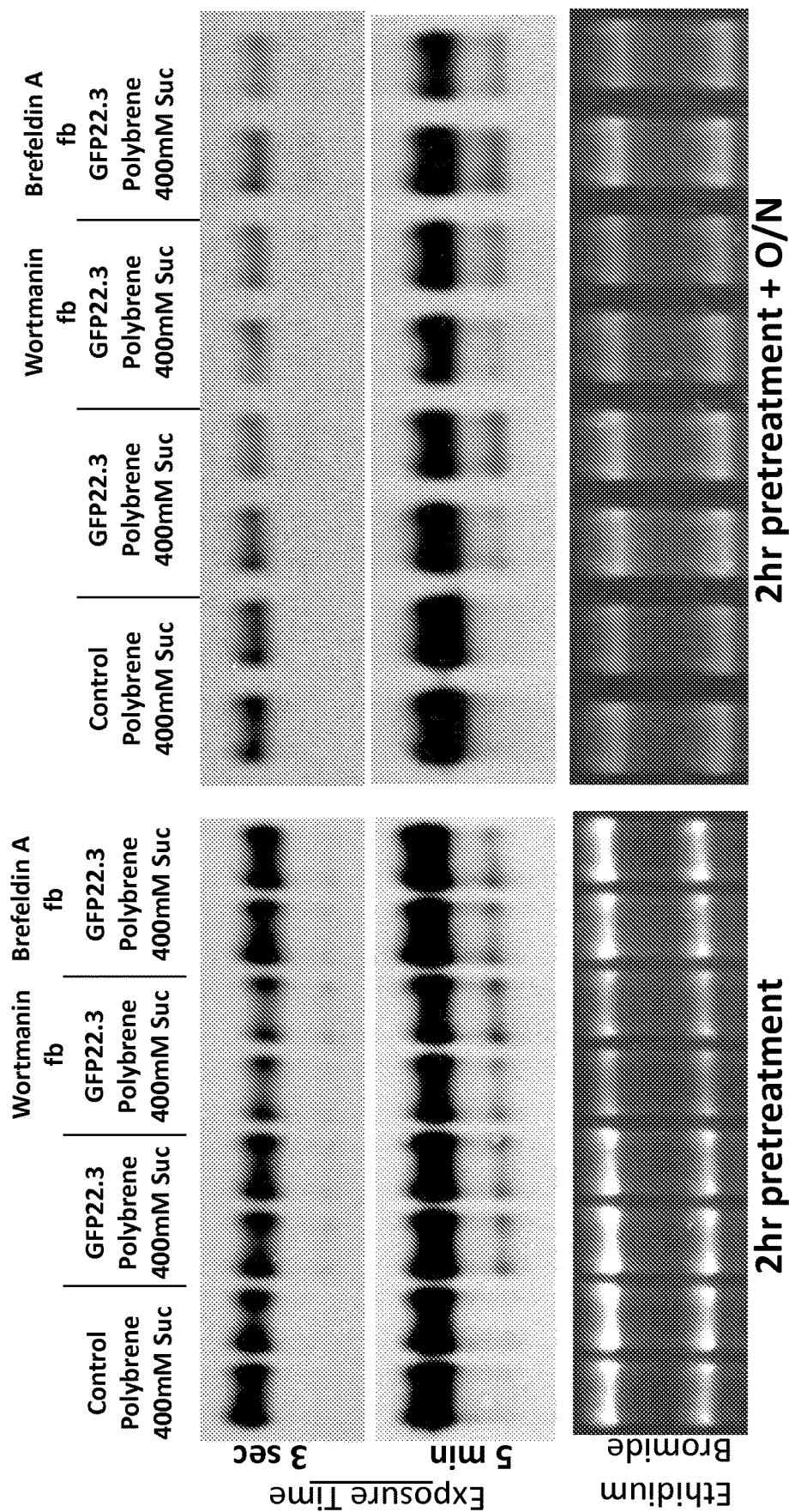

FIG. 25: Northern blot analysis of RNA levels after treatments with Polybrene®, Wortmanin or Brefeldin A and dsRNA targeting GFP (GFP22-3, SEQ ID NO:1/SEQ ID NO:2). Extracts were analyzed after treatments with different formulations and either a 2 hr pretreatment or an additional overnight incubation with formulation.

Figure 26:
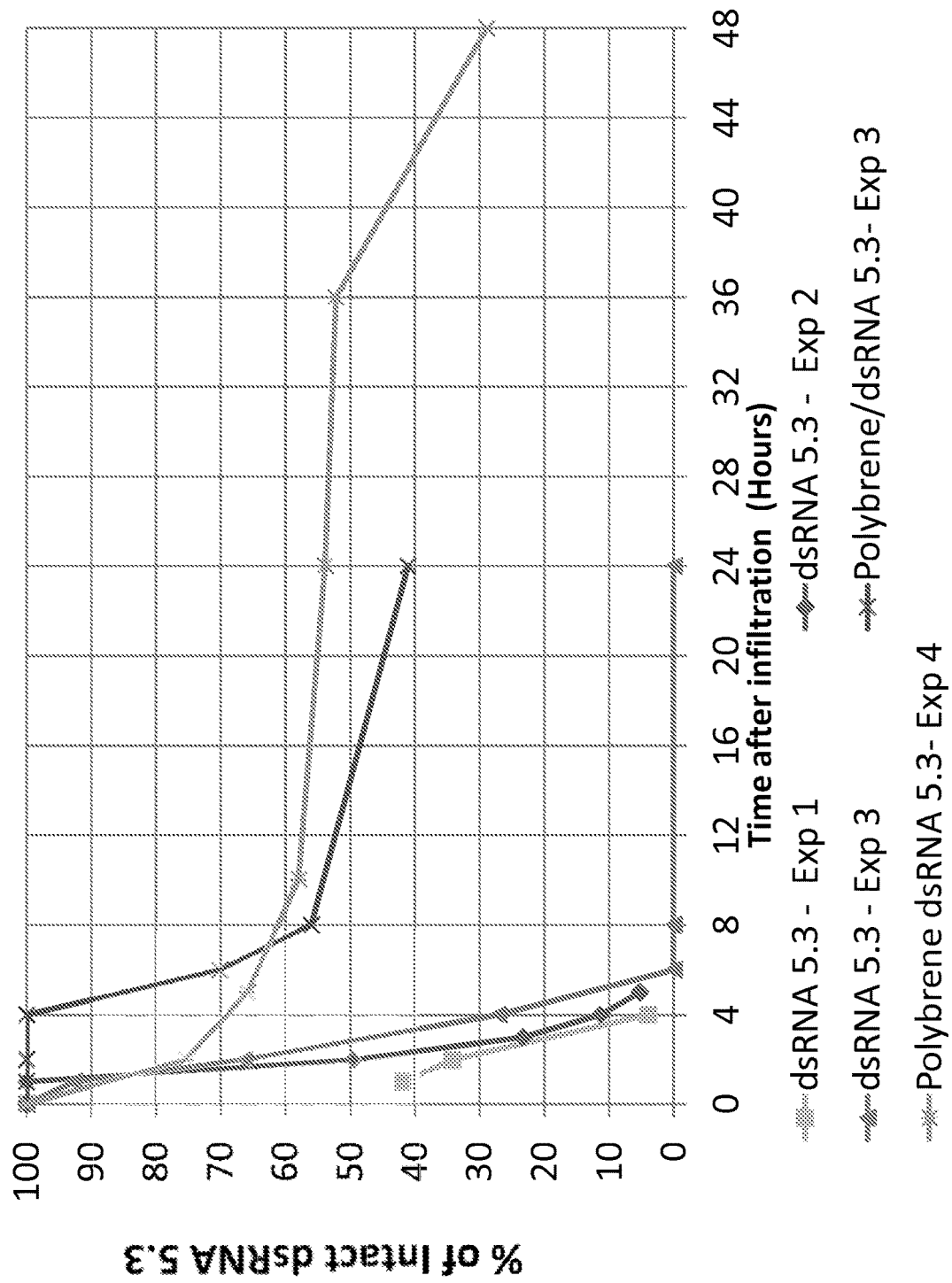

FIG. 26: Anion exchange HPLC analysis of RNA after leaf infiltration in *N. benthamiana* leaves. The integrity of uncomplexed or complexed dsRNA was measured using anion exchange HPLC for the dsRNA 5.3 (SEQ ID NO:3/SEQ ID NO:4).

Figure 27:
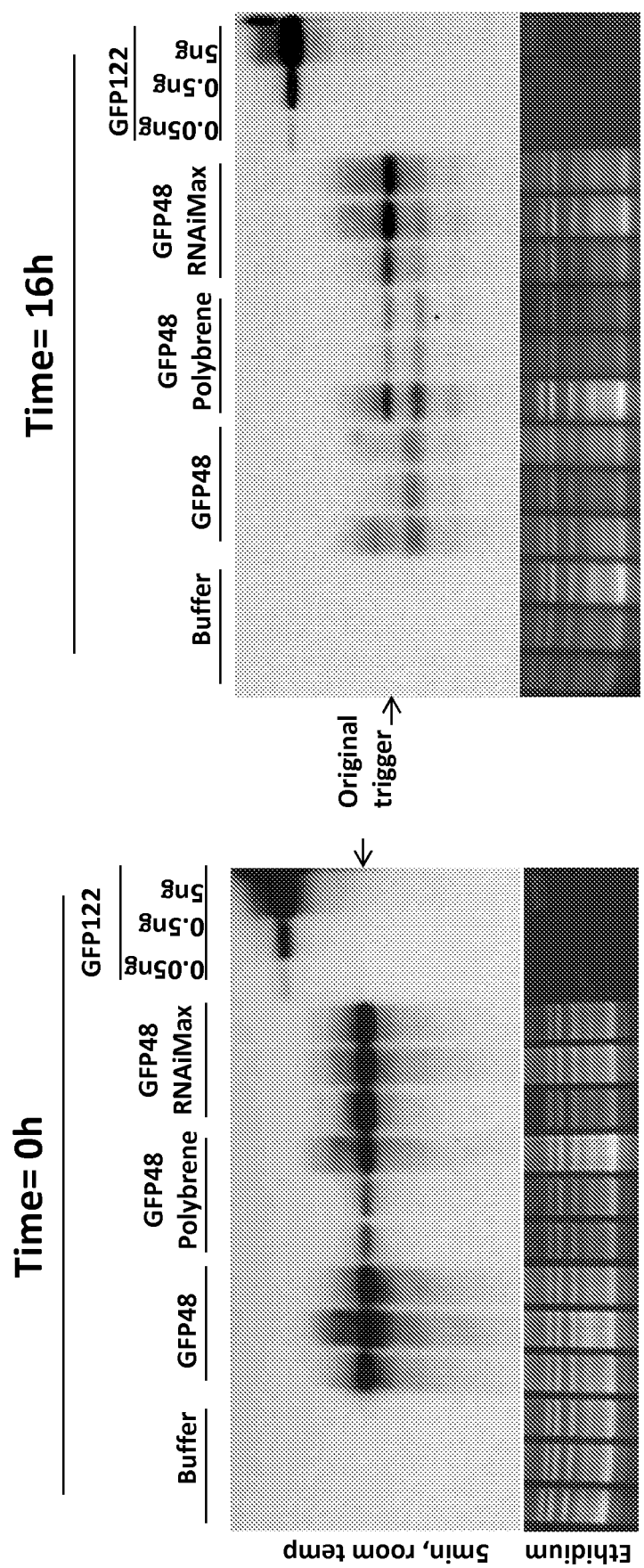

FIG. 27: Northern blot analysis of RNA after leaf infiltration in *N. benthamiana* leaves at 0 hr after infiltration or 16 hr after infiltration. The stability of dsRNA was analyzed by Northern blot for uncomplexed dsRNA GFP48 (SEQ ID NO:25) or dsRNA GFP48 complexed with either Polybrene® or RNAiMAX.

DETAILED DESCRIPTION

Unless defined otherwise, technical and scientific terms as used herein have the same meaning as commonly understood by one of ordinary skill in the art. One skilled in the art will recognize many methods can be used in the practice of the present disclosure. Indeed, the present disclosure is in no way limited to the methods and materials described. Moreover, the present disclosure is not intended to be limited by any particular scientific theory. For purposes of the present disclosure, the following terms are defined below.

Any references cited herein are incorporated by reference in their entireties.

As used herein, the singular form "a," "an," and "the" include plural references unless the context clearly dictates otherwise. For example, the term "a compound" or "at least one compound" may include a plurality of compounds, including mixtures thereof.

As used herein, the term "about" refers to ±10%.

As used herein, "polynucleotide" refers to a nucleic acid molecule containing multiple nucleotides and generally refers both to "oligonucleotides" (a polynucleotide molecule of 18-25 nucleotides in length) and polynucleotides of 26 or more nucleotides. Aspects of this disclosure include compositions including oligonucleotides having a length of 18-25 nucleotides (e.g., 18-mers, 19-mers, 20-mers, 21-mers, 22-mers, 23-mers, 24-mers, or 25-mers), or medium-length polynucleotides having a length of 26 or more nucleotides (e.g., polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e.g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target gene including coding or non-coding or both coding and non-coding portions of the target gene). Where a polynucleotide is double-stranded, its length can be similarly described in terms of base pairs.

As used herein, the term "polyelectrolyte" refers to a molecule in which a substantial portion of the constitutional units have ionizable or ionic groups, or both. Examples of polyelectrolytes include, but are not limited to, cationic proteins and cationic polymers.

As used herein, the term "osmolyte" refers to a compound that affects osmosis. Natural osmolytes include, for example, sucrose, mannitol, fructose, galactose, sodium chloride, glycerol, sorbitol, polyalchohols, proline, trehalose, trimethylamine N-oxide (TMAO), dimethylsulfoniopropionate, trimethylglycine, sarcosine, betaine, glycerophosphorylcholine, myo-inositol, taurine, and *glycine*.

As used herein, a "dsRNA" molecule refers to a molecule comprising two antiparallel ribonucleotide strands bound together by hydrogen bonds, each strand of which comprises ribonucleotides linked by phosphodiester bonds running in the 5'-3' direction in one and in the 3'-5' direction in the other. Two antiparallel strands of a dsRNA can be perfectly complementary to each other or comprise one or more mismatches up to a degree where any one additional mismatch causes the disassociation of the two antiparallel strands. A dsRNA molecule can have perfect complementarity over the entire dsRNA molecule, or comprises only a portion of the entire molecule in a dsRNA configuration. Two antiparallel strands of a dsRNA can also be from a continuous chain of ribonucleotides linked by phosphodiester bonds, e.g., a hairpin-like structure (often also called a stem-loop structure). In some embodiments, a dsRNA molecule is identified by two SEQ ID NOs, where the first SEQ ID NO represents the sense strand of the dsRNA and the second SEQ ID NO represents the antisense strand of the dsRNA. In other embodiments, a dsRNA molecule is identified by one SEQ ID NO that represents the sense strand of the dsRNA.

As used herein, in the context of RNA-mediated gene silencing, the sense strand of a dsRNA molecule refers to a strand comprising a sequence that is identical or nearly identical to a target sequence. The antisense strand of a dsRNA molecule refers to a strand having a sequence complementary to a target sequence. In a DNA context, the term "antisense" refers to a nucleotide sequence that is inverted relative to its normal orientation for transcription or function and so expresses an RNA transcript that is complementary to a target sequence (e.g., it can hybridize to the target gene mRNA molecule or single stranded genomic DNA through Watson-Crick base pairing) or that is complementary to a target DNA molecule such as, for example, genomic DNA present in the host cell.

As used herein, "small RNA (sRNA)" refers to any RNA molecule that is about 15-30 nucleotides long, preferably 21-24 nucleotides long. A "21-24mer small RNA" or "21-24mer sRNA" refers to a small RNA of 21-24 nucleotides which may be double- or single-stranded. A double-stranded 21-24mer sRNA can comprise at one or both ends one or more structures selected from the group consisting of blunt, 3' overhang, and 5' overhang. A double-stranded 21-24mer sRNA processed by a Dicer-like protein from a dsRNA precursor molecule typically comprise a 2-nt overhang at both ends.

Small RNA includes, without limitation, siRNA (small interfering RNA), miRNA (microRNA), ta-siRNA(trans activating siRNA), activating RNA (RNAa), nat-siRNA (natural anti-sense siRNA), hc-siRNA (heterochromatic siRNA), cis-acting siRNA, lmiRNA (long miRNA), lsiRNA (long siRNA) and easiRNA (epigenetically activated siRNA). Preferred sRNA molecules of the disclosure are siRNA molecules. A sRNA, in its mature form, can be either double-stranded or single-stranded, although the biogenesis of a sRNA often involves a sRNA duplex which is a double-stranded form of sRNA. While not limited by a particular theory, a sRNA duplex is often processed from a dsRNA precursor by proteins, such as Dicer-like proteins.

As used herein, the term "siRNA" (also referred to herein interchangeably as "small interfering RNA"), is a class of double-stranded RNA molecules having about 18-25 nucleotides in length (e.g., 18-mers, 19-mers, 20-mers, 21-mers, 22-mers, 23-mers, 24-mers, or 25-mers). A double-stranded siRNA generally has perfect or near perfect complementarity. Without being limited by any theory, a role of siRNA is its involvement in the RNA interference (RNAi) pathway, where it interferes with the expression of a specific target gene.

As used herein, the term "functional siRNA" refers to a siRNA which is effective in silencing an intended target gene.

As used herein, the phrase "RNA silencing" refers to a group of regulatory mechanisms (e.g., RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding target gene.

As used herein, a "synthetic sequence" refers to a nucleic acid sequence which lacks a corresponding sequence that naturally occurs.

As used herein, a "target-specific sequence" refers to a nucleic acid sequence that is essentially identical, nearly identical, identical, or complement of any, to a target nucleotide sequence. For example, a target-specific sequence can be derived from a sequence of a messenger RNA (mRNA) which, when hybridizes with a small RNA molecule and leads to the attenuation of target gene expression. Conversely, a "non-target-specific sequence" refers to any nucleic acid sequence that is not a target-specific sequence. In some embodiments, the target nucleotide sequence is a coding region of a mRNA, a 5' untranslated region, a 3' untranslated region, an intron, a promoter, an enhancer, a terminator, an rRNA, a tRNA, a small nuclear RNA (snRNA), a small nucleolar RNA (snoRNA), a non-coding RNA involved in RNA interference, and any combination thereof.

As used herein, a "trigger" or "trigger polynucleotide" is an exogenous nucleic acid molecule which comprises a sequence essentially identical, nearly identical, identical, or complement of any, to a polynucleotide sequence of a target gene or an RNA expressed from the target gene or a fragment thereof, and functions to cause the silencing of the target gene. A trigger molecule can be a dsRNA, a single-stranded RNA, a RNA-DNA hybrid, a double-stranded or single-stranded DNA. A trigger molecule may comprise naturally-occurring nucleotides, modified nucleotides, nucleotide analogues or any combination thereof. In some aspects, a trigger molecule may be incorporated within a larger nucleic acid molecule, for example in a pri-miRNA molecule. In some aspects, a trigger molecule may be processed into a siRNA.

Polynucleotide compositions used in the various aspects of this disclosure include compositions including oligonucleotides or polynucleotides or a mixture of both, including RNA or DNA or RNA/DNA hybrids or chemically modified oligonucleotides or polynucleotides or a mixture thereof. In some aspects, the polynucleotide may be a combination of ribonucleotides and deoxyribonucleotides, e.g., synthetic polynucleotides consisting mainly of ribonucleotides but with one or more terminal deoxyribonucleotides or synthetic polynucleotides consisting mainly of deoxyribonucleotides but with one or more terminal dideoxyribonucleotides. In some aspects, the polynucleotide includes non-canonical nucleotides such as inosine, thiouridine, or pseudouridine. In some aspects, the polynucleotide includes chemically modified nucleotides. Examples of chemically modified oligonucleotides or polynucleotides are well known in the art; see, e.g., Verma and Eckstein (1998) Annu. Rev. Biochem., 67:99-134. For example, the naturally occurring phosphodiester backbone of an oligonucleotide or polynucleotide can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labeled with a fluorescent moiety (e.g., fluorescein or rhodamine) or other label (e.g., biotin).

The polynucleotides can be single- or double-stranded RNA or single- or double-stranded DNA or double-stranded DNA/RNA hybrids or modified analogues thereof, and can be of oligonucleotide lengths or longer. In more specific aspects of the disclosure the polynucleotides that provide single-stranded RNA in the plant cell are selected from the group consisting of (a) a single-stranded RNA molecule, (b) a single-stranded RNA molecule that self-hybridizes to form a double-stranded RNA molecule, (c) a double-stranded RNA molecule, (d) a single-stranded DNA molecule, (e) a single-stranded DNA molecule that self-hybridizes to form a double-stranded DNA molecule, and (f) a single-stranded DNA molecule including a modified Pol III gene that is transcribed to an RNA molecule, (g) a double-stranded DNA molecule, (h) a double-stranded DNA molecule including a modified Pol III gene that is transcribed to an RNA molecule, (i) a double-stranded, hybridized RNA/DNA molecule, or combinations thereof. In some aspects these polynucleotides include chemically modified nucleotides or non-canonical nucleotides. In aspects of the method the polynucleotides include double-stranded DNA formed by intramolecular hybridization, double-stranded DNA formed by intermolecular hybridization, double-stranded RNA formed by intramolecular hybridization, or double-stranded RNA formed by intermolecular hybridization. In one aspect the polynucleotides include single-stranded DNA or single-stranded RNA that self-hybridizes to form a hairpin structure having an at least partially double-stranded structure including at least one segment that will hybridize under physiological conditions in the cell to RNA transcribed from the gene targeted for suppression. Not intending to be bound by any mechanism, it is believed that such polynucleotides are or will produce single-stranded RNA with at least one segment that will hybridize under physiological conditions in a cell to RNA transcribed from the gene targeted for suppression. In certain other aspects the polynucleotides further includes a promoter, generally a promoter functional in a plant, e.g., a Pol II promoter, a Pol III promoter, a Pol IV promoter, or a Pol V promoter.

The polynucleotides are designed to induce systemic regulation or suppression of an endogenous gene in a plant and are designed to have a sequence essentially identical or essentially complementary to the sequence (which can be coding sequence or non-coding sequence) of an endogenous gene of a plant or to the sequence of RNA transcribed from an endogenous gene of a plant. By "essentially identical" or "essentially complementary" is meant that the polynucleotides (or at least one strand of a double-stranded polynucleotide) are designed to hybridize under physiological conditions in cells of the plant to the endogenous gene or to RNA transcribed from the endogenous gene to effect regulation or suppression of the endogenous gene.

Aspects of single-stranded polynucleotides functional in this disclosure have sequence complementarity that need not be 100% but is at least sufficient to permit hybridization to RNA transcribed from the target gene to form a duplex under physiological conditions in a plant cell to permit cleavage by a gene silencing mechanism. Thus, in aspects the segment is designed to be essentially identical to, or essentially complementary to, a sequence of 18 or more contiguous nucleotides in either the target gene or messenger RNA transcribed from the target gene. By "essentially identical" is meant having 100% sequence identity or at least about 83, 84, 85, 86, 87, 88, 89, 90, 91, 92, 93, 94, 95, 96, 97, 98, or 99% sequence identity when compared to the sequence of 18 or more contiguous nucleotides in either the target gene or RNA transcribed from the target gene; by "essentially complementary" is meant having 100% sequence complementarity or at least about 83, 84, 85, 86, 87, 88, 89, 90, 91, 92, 93, 94, 95, 96, 97, 98, or 99% sequence complementarity when compared to the sequence of 18 or more contiguous nucleotides in either the target gene or RNA transcribed from the target gene. In some aspects of this disclosure polynucleotide molecules are designed to have 100% sequence identity with or complementarity to one allele of a given target gene (e.g., coding or non-coding sequence of a gene for an herbicide-tolerance protein, an herbicide-deactivating protein, a stress-response gene, or an essential gene); in other aspects the polynucleotide molecules are designed to have 100% sequence identity with or complementarity to multiple alleles of a given target gene.

In one aspect of the disclosure the polynucleotides are modified RNA polymerase III genes, e.g., genes that transcribe 7SL signal recognition particle RNA or U6 spliceosomal RNA (Pol III genes) or polynucleotides containing a functional Pol III promoter sequence. In one aspect, the polynucleotides are modified Pol III genes containing sense and anti-sense DNA corresponding to RNA of the targeted gene identified for regulation replacing the DNA sequence originally transcribed by the Pol III gene.

The polynucleotides useful in this disclosure typically effect regulation or modulation (e.g., suppression) of gene expression during a period during the life of the treated plant of at least 1 week or longer and typically in systemic fashion. For instance, within days of treating a plant leaf with a polynucleotide composition of this disclosure, primary and transitive siRNAs can be detected in other leaves lateral to and above the treated leaf and in apical tissue.

Methods of making polynucleotides are well known in the art. Commercial preparation of oligonucleotides often provides 2 deoxyribonucleotides on the 3' end of the sense strand. Long polynucleotide molecules can be synthesized from commercially available kits, e.g., kits from Ambion have DNA ligated on the 5' end that encodes a bacterial T7 polymerase promoter that makes RNA strands that can be assembled into a dsRNA. Alternatively, dsRNA molecules can be produced from expression cassettes in bacterial cells that have regulated or deficient RNase III enzyme activity. Long polynucleotide molecules can also be assembled from multiple RNA or DNA fragments. In some aspects design parameters such as Reynolds score and Tuschl rules are known in the art and are used in selecting polynucleotide sequences effective in gene silencing. In some aspects random design or empirical selection of polynucleotide sequences is used in selecting polynucleotide sequences effective in gene silencing. In some aspects the sequence of a polynucleotide is screened against the genomic DNA of the intended plant to minimize unintentional silencing of other genes.

The polynucleotide compositions of this disclosure are useful in compositions, such as solutions of polynucleotide molecules, at low concentrations, alone or in combination with other components (e.g., surfactants, salts, and non-polynucleotide herbicides) either in the same solution or in separately applied solutions. While there is no upper limit on the concentrations and dosages of polynucleotide molecules that can useful in the methods of this disclosure, lower effective concentrations and dosages will generally be sought for efficiency. The concentrations can be adjusted in consideration of the volume of spray applied to plant leaves. In one aspect, a useful treatment for herbaceous plants using 25-mer oligonucleotide molecules is about 1 nanomole of oligonucleotide molecules per plant, e.g., from about 0.05 to 1 nanomole per plant. Other aspects for herbaceous plants include useful ranges of about 0.05 to about 100 nanomoles, or about 0.1 to about 20 nanomoles, or about 1 nanomole to about 10 nanomoles of polynucleotides per plant. Very large plants, trees, or vines may require correspondingly larger amounts of polynucleotides. When using long dsRNA molecules that can be processed into multiple oligonucleotides, lower concentrations can be used. In the examples to below to illustrate aspects of the disclosure the factor 1X when applied to oligonucleotide molecules is arbitrarily used to denote a treatment of 0.8 nanomoles of polynucleotide molecule per plant; 10X, 8 nanomoles of polynucleotide molecule per plant; and 100X, 80 nanomoles of polynucleotide molecule per plant, for example, in Example 23 plants were treated with an aqueous solution comprising a 100X treatment of EPSPS dsRNA (264 micrograms or 80 nanomoles) per plant.

In one aspect, a herbicide composition as disclosed herein can comprise one or more target-specific sequences essentially identical or identical to a sequence (which can be coding sequence or non-coding sequence) selected from the group consisting of a plant endogenous gene sequence, a plant phytopathogen gene sequence, a plant viral gene sequence, a plant insect gene sequence, and combinations thereof. In one aspect, a polynucleotide composition as disclosed herein can induce systemic regulation or suppression of an endogenous gene in a plant.

In one aspect, a herbicide composition as disclosed herein has one or more target genes of interest which encode herbicide-tolerance proteins. Examples of a protein that provides tolerance to an herbicide include e.g., a 5-cnolpyruvylshikimatc-3-phosphate synthase (EPSPS), a glyphosate oxidoreductase (GOX), a glyphosate decarboxylase, a glyphosate-N-acetyl transferase (GAT), a dicamba monooxygenase, a phosphinothricin acetyltransferase, a 2,2-dichloropropionic acid dehalogenase, an acetohydroxyacid synthase, an acetolactate synthase, a haloarylnitrilasc, an acetyl-coenzyme A carboxylase, a dihydropteroate synthase, a phytoene desaturase, a protoporphyrin IX oxygenase, a hydroxyphenylpyruvate dioxygenase, a para-aminobenzoate synthase, a glutamine synthase, a cellulose synthase, a beta-tubulin, and a serine hydroxymethyltransferase. Examples of nucleic acids encoding proteins conferring tolerance to herbicides include 5-enolpyruvylshikimate-3-phosphate synthases (EPSPS; see, e.g., U.S. Pat. Nos. 5,627,061, 5,633,435 RE39,247, 6,040,497, and 5,094,945, and PCT International Application Publications WO04074443 and WO04009761), glyphosate oxidoreductase (GOX; U.S. Pat. No. 5,463,175), glyphosate decarboxylase (PCT International Application Publication WO05003362, U.S. Pat. No. 7,405,347, and U.S. Patent Application Publication 2004/0177399), glyphosate-N-acetyl transferase (GAT; U.S. Pat. No. 7,714,188) conferring tolerance to glyphosate; dicamba monooxygenase conferring tolerance to auxin-like herbicides such as dicamba (U.S. Pat. No. 7,105,724); phosphinothricin acetyltransferase (pat or bar) conferring tolerance to phosphinothricin or glufosinate (U.S. Pat. No. 5,646,024); 2,2-dichloropropionic acid dehalogenase conferring tolerance to 2,2-dichloropropionic acid (Dalapon) (PCT International Application Publication WO9927116); acetohydroxyacid synthase or acetolactate synthase conferring tolerance to acetolactate synthase inhibitors such as sulfonylurca, imidazolinonc, triazolopyrimidine, pyrimidyloxybenzoates and phthalidc (U.S. Pat. No. 6,225,105); haloarylnitrilase (Bxn) for conferring tolerance to bromoxynil (U.S. Pat. No. 4,810,648); modified acetyl-coenzyme A carboxylase for conferring tolerance to cyclohexanedione (sethoxydim) and aryloxyphenoxypropionate (haloxyfop) (U.S. Pat. No. 6,414,222); dihydropteroate synthase (sul I) for conferring tolerance to sulfonamide herbicides (U.S. Pat. No. 5,719,046); 32 kDa photosystem II polypeptide (psbA) for conferring tolerance to triazine herbicides (Hirschberg et al., 1983, Science, 222:1346-1349); anthranilate synthase for conferring tolerance to 5-methyltryptophan (U.S. Pat. No. 4,581,847); dihydrodipicolinic acid synthase (dap A) for conferring to tolerance to aminoethyl cysteine (PCT International Application Publication WO8911789); phytoene desaturase (crtI) for conferring tolerance to pyridazinone herbicides such as norflurazon (Japan Patent JP06343473); hydroxyphenylpyruvate dioxygenase, a 4-hydroxyphenylacetic acid oxidase and a 4-hydroxyphenylacetic 1-hydrolase (U.S. Pat. No. 7,304,209) for conferring tolerance to cyclopropylisoxazole herbicides such as isoxaflutole (U.S. Pat. No. 6,268,549); modified protoporphyrinogen oxidase I (protox) for conferring tolerance to protoporphyrinogen oxidase inhibitors (U.S. Pat. No. 5,939,602); aryloxyalkanoate dioxygenase (AAD-1) for conferring tolerance to an herbicide containing an aryloxyalkanoate moiety (PCT International Application Publication WO05107437); a serine hydroxymethyltransferase (U.S. Patent Application Publication 2008/0155716), a glufosinate-tolerant glutamine synthase (U.S. Patent Application Publication 2009/0018016). Examples of such herbicides include phenoxy auxins (such as 2,4-D and dichlorprop), pyridyloxy auxins (such as fluroxypyr and triclopyr), aryloxyphenoxypropionates (AOPP) acetyl-coenzyme A carboxylase (ACCase) inhibitors (such as haloxyfop, quizalofop, and diclofop), and 5-substituted phenoxyacetate protoporphyrinogen oxidase 1x inhibitors (such as pyraflufen and flumiclorac). All foregoing cited patents and patent application publications, including sequences of the nucleic acids encoding herbicide-tolerance proteins and sequences of the herbicide-tolerance proteins disclosed therein, are incorporated herein by reference in their entireties.

In one aspect, a herbicide composition as disclosed herein comprises one or more modified nucleotides of any kind in any part of the polynucleotide molecule. Examples of modified RNA nucleotides can be found in Limbach et al. Summary: the modified nucleosides of RNA. Nucleic Acids Res. 1994, 22(12):2183-96; and Abeydeera et al. 2008, Modified Nucleosides in RNA. Wiley Encyclopedia of Chemical Biology. 1-14, both of which are incorporated by reference in their entireties. Further exemplary modified nucleotides can comprise a modified base including, but not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosinc, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. In another aspect, a polynucleotide composition as disclosed herein comprises a non-canonical nucleotide such as inosine, thiouridine, or pseudouridine.

In another aspect, a herbicide composition as disclosed herein comprises a modified polynucleotide backbone including, but not limited to, phosphorothioates, chiral phosphorothioates, phosphorodithioates, phosphotriesters, aminoalkyl phosphotriesters, methyl and other alkyl phosphonates, phosphinates, phosphoramidates, thionophosphoramidates, thionoalkylphosphonates, thionoalkylphosphotriesters, and boranophosphates.

In another aspect, a polynucleotide composition as disclosed herein comprises one or more active ingredients of a herbicidal, insecticidal, or pesticidal composition. A polynucleotide composition of the instant disclosure can further comprise various molecules or agents. In one aspect, a polynucleotide composition as disclosed herein is formulated with counter-ions or other molecules that are known to associate with nucleic acid molecules, e.g., tetraalkyl ammonium ions, trialkyl ammonium ions, sulfonium ions, lithium ions, and polyamines such as spermine, spermidine, or putrescine. In another aspect, a polynucleotide composition as disclosed herein is formulated with one or more non-polynucleotide herbicides (e.g., glyphosate, 2,4-dichloropropionic acid, bromoxynil, sulfonylurea, imidazolinone, triazolopyrimidine, pyrimidyloxybenzoates, phthalide, bialaphos, phosphinothricin, glufosinate, atrazine, dicamba, cyclohexanedione (sethoxydim), and aryloxyphenoxypropionate (haloxyfop)).

In a further aspect, a polynucleotide composition herein is formulated with at least one transferring agent or permeability-enhancing agent which conditions the surface of a plant tissue, e.g., seed, leaves, stems, roots, flowers, or fruits, for permeation by the polynucleotide into plant cells. The transfer of a polynucleotide composition as disclosed herein into plant cells can be facilitated by the prior or contemporaneous application of a transferring agent to the plant tissue. The transferring agent enables a pathway for a dsRNA through cuticle wax barriers, stomata and/or cell wall or membrane barriers and into plant cells.

Methods and Compositions for Delivering Polynucleotides

The present disclosure provides a method for delivering one or more polynucleotides into a plant cell, comprising applying onto a plant or a part thereof a mixture comprising: a) a cationic polyelectrolyte; and b) the one or more polynucleotides, and wherein the one or more polynucleotides comprise at least one segment of 18 or more contiguous nucleotides that shares about 90% to 100% sequence identity to a fragment of a target gene, or the complement thereof. In some embodiments, the mixture further comprises an osmolyte. In some embodiments, an osmolyte is applied to the plant or part thereof prior to, concomitant with, or subsequent to application of the cationic polyelectrolyte and one or more polynucleotides. In one embodiment, the present disclosure provides a method for delivering one or more polynucleotides into a plant cell, comprising applying onto a plant or a part thereof a mixture comprising a cationic polyelectrolyte and the one or more polynucleotides, wherein the one or more polynucleotides comprise at least one segment of 18 or more contiguous nucleotides that shares about 90% to 100% sequence identity to a fragment of a target gene, or the complement thereof. In one embodiment, the mixture comprising a cationic polyelectrolyte and the one or more polynucleotides does not comprise an osmolyte. In one aspect, the polynucleotide suppresses expression of the target gene. In some embodiments, the polynucleotide comprises one segment of 18 or more contiguous nucleotides that shares at least about 91%, 92%, 93%, 94%, 95%, 96%, 97%, 98%, or 99% sequence identity to a fragment of a target gene, or the complement thereof. In some embodiments, the target gene encodes a protein that provides resistance to a chemical herbicide, and the mixture further comprises the chemical herbicide. In some embodiments, the cationic polyelectrolyte and the one or more polynucleotides form a complex. In some embodiments, the cationic polyelectrolyte and the one or more polynucleotides do not form a complex.

The present disclosure also provides a composition for delivering a polynucleotide into a plant cell, comprising: a) a cationic polyelectrolyte; and b) the polynucleotide, and wherein the polynucleotide comprises at least one segment of 18 or more contiguous nucleotides that shares about 90% to 100% sequence identity to a fragment of a target gene, or the complement thereof. In some embodiments, the composition further comprises an osmolyte. In one aspect, the polynucleotide suppresses expression of the target gene. In some embodiments, the polynucleotide comprises one segment of 18 or more contiguous nucleotides that shares at least about 91%, 92%, 93%, 94%, 95%, 96%, 97%, 98%, or 99% sequence identity to a fragment of a target gene, or the complement thereof. In some embodiments, the target gene encodes a protein that provides resistance to a chemical herbicide, and the composition further comprises the chemical herbicide.

In some embodiments, the cationic polyelectrolyte comprises a hydrophilic modification. In some embodiments, the hydrophilic modification is PEGylation, quaternization, or a combination thereof. In other embodiments, the cationic polyelectrolyte comprises a hydrophobic modification. In some embodiments, the hydrophobic modification is deoxycholic acid modification, alkylation, thiolation, or a combination thereof.

In some embodiments, the polyelectrolyte is cationic independent of pH. In some embodiments, the polyelectrolyte is cationic at a pH of less than about 9.0, less than about 8.0, or less than about 7.0. In some embodiments, the polyelectrolyte is not cationic at a pH higher than about 6.0, higher than about 7.0, or higher than about 8.0.

In some embodiments, the polyelectrolyte is a polymer. In some embodiments, the polymer is linear or branched. Examples of polymers include, but are not limited to, polyethyleneimine (PEI), Polybreneg(Polyb or PB), poly(dimethyl aminoethyl methacrylate), p(DMAEMA), poly(trimethyl aminoethyl methacrylate, p(TMAEMA), poly(vinylpyridine), chitosan, diethylaminoethyl dextran (DEAE-dextran), polyamidoamine (PAMAM) dendrimers, poly(lactide-co-glycolide).

In some embodiments, the polyelectrolyte is a cationic peptide. Examples of cationic peptides include, but are not limited to, poly-arginine, poly-lysine, Endoporter, and other cell penetrating peptides. Non-limiting examples or cell penetrating peptides include peptides from the coat protein of Cowpea Chlorotic Mottle Virus (CCMV, e.g., SEQ ID NO:27), peptides from the coat protein of Brome Mosaic Virus (BMV, e.g., SEQ ID NO:28), HIV Tat (YGRKKRRQRRR, SEQ ID NO:29), HIV Rev (TRQARRNRRRRWRERQR, SEQ ID NO:30), FHV coat (RRRRNRTRRNRRRVR, SEQ ID NO:31), HSV-1 protein VP22 (DAATATRGRSAASRPTERPRAPARSASR-PRRPVD, SEQ ID NO:32), Penetratin (RQIK1WFQNRRMKWK.K, SEQ ID NO:33), EB1 (penetratin analog) (LIRLWSHLIHIWFQNRRLKWKKK, SEQ ID NO:34), MPG (GALFLGFL-GAAGSTMGAWSQPKKKRKV, SEQ ID NO:35), PR9 (FFLIPKGRRRRRRRRR, SEQ ID NO:36), SR9 (RRRRRRRRR, SEQ ID NO:37), IR9 (GLFEAIEGFIEN-GWEGMIDGWYGRRRRRRRRR, SEQ ID NO:38), HR9 (CHHHHHRRRRRRRRRHHHHHC, SEQ ID NO:39), Transportan (CLIKKALAALAKLNIKLLYGASNLTWG, SEQ ID NO:40), CADY (GLWRALWRLLRSLWRLL-WRA, SEQ ID NO:41), C6 (RLLRLLLRLWRRLLRLLR, SEQ ID NO:42), C6M1 (RLWRLLWRLWRRLWRLLR, SEQ ID NO:43), PF20 (LLKLLKKLLKLLKKLLKLL, SEQ ID NO:44), NAP (KALKLKLALALLAKLKLA, SEQ ID NO:45), Steryl-NAP (Stearyl-KALKLKLALALLAK-LKLA, SEQ ID NO:45), POD (GGG[ARKKAAKA]4, SEQ ID NO:46), 10H (CHHHHHRKKRRQRRRRHHHHHC, SEQ ID NO:47), HR9 (CHHHHHRRRRRRRR-RHHHHHC, SEQ ID NO:48), PasR8 (FFLIPKGRRRRRRRRGC, SEQ ID NO:49), PR9 (FFLIPKGRRRRRRRRR, SEQ ID NO:50), GALA (WEAALAEALAEALAEHLAEALAEALEALAA, SEQ ID NO:51), and Polyornithine.

In some embodiments, the cationic polyelectrolyte binds to the polynucleotide via an ionic bond. In other embodiments, the cationic polyelectrolyte and polynucleotide do not form a complex.

In some embodiments, the ratio of the polyelectrolyte and the polynucleotide in the complex is from about 100:1 to about 1:2 (w/w). In some embodiments, the complex has a ratio of nitrogen of the polymer to phosphate of the polynucleotide (N/P ratio) of about 1:1 to about 100:1. In some embodiments, the complex has a N/P ratio of about 90:1, about 80:1, about 70:1, about 60:1, about 50:1, about 40:1, about 30:1, about 20:1, about 10:1, about 5:1, about 4:1, about 3:1, or about 2:1. In some embodiments, the complex has a N/P ratio of at least 3:1.

In some embodiments, the polyelectrolyte is biodegradable. In other embodiments, the polyelectrolyte is a polypeptide. In some embodiments, the polypeptide comprises poly-lysine, poly-arginine, or a combination thereof.

In some embodiments, the polyelectrolyte is at a concentration from about 0.01 µg/ml to about 1000 µg/ml. In certain embodiments, the polyelectrolyte is at a concentration from about 0.01 µg/ml to about 500 µg/ml, from about 0.01 µg/ml to about 250 µg/ml, from about 0.01 µg/ml to about 100 µg/ml, from about 0.01 µg/ml to about 50 µg/ml, from about 0.01 µg/ml to about 25 µg/ml, from about 0.01 µg/ml to about 10 µg/ml, from about 0.01 µg/ml to about 5 µg/ml, from about 0.01 pig/ml to about 1 pig/ml, from about 0.01 µg/ml to about 0.5 µg/ml, from about 0.01 µg/ml to about 0.1 µg/ml, from about 0.05 µg/ml to about 1000 µg/ml, from about 0.05 µg/ml to about 500 µg/ml, from about 0.05 µg/ml to about 250 µg/ml, from about 0.05 µg/ml to about 100 µg/ml, from about 0.05 µg/ml to about 50 µg/ml, from about 0.05 µg/ml to about 25 µg/ml, from about 0.05 µg/ml to about 10 µg/ml, from about 0.05 µg/ml to about 5 µg/ml, from about 0.05 µg/ml to about 1 µg/ml, from about 0.05 µg/ml to about 0.5 µg/ml, from about 0.05 µg/ml to about 0.1 µg/ml, from about 0.1 µg/ml to about 1000 µg/ml, from about 0.1 µg/ml to about 500 µg/ml, from about 0.1 µg/ml to about 250 µg/ml, from about 0.1 µg/ml to about 100 µg/ml, from about 0.1 pig/ml to about 50 µg/ml, from about 0.1 µg/ml to about 25 µg/ml, from about 0.1 µg/ml to about 10 µg/ml, from about 0.1 µg/ml to about 5 µg/ml, from about 0.1 µg/ml to about 1 µg/ml, from about 1 µg/ml to about 1000 µg/ml, from about 1 µg/ml to about 500 µg/ml, from about 1 µg/ml to about 250 µg/ml, from about 1 µg/ml to about 100 µg/ml, from about 1 µg/ml to about 50 µg/ml, from about 1 µg/ml to about 25 µg/ml, from about 1 µg/ml to about 10 µg/ml, from about 1 pig/ml to about 5 µg/ml, from about 10 µg/ml to about 1000 µg/ml, from about 10 µg/ml to about 500 µg/ml, from about 10 µg/ml to about 250 µg/ml, from about 10 µg/ml to about 100 µg/ml, from about 10 µg/ml to about 50 µg/ml, from about 10 µg/ml to about 25 µg/ml, from about 50 µg/ml to about 1000 µg/ml, from about 50 µg/ml to about 500 µg/ml, from about 50 µg/ml to about 250 µg/ml, from about 50 µg/ml to about 100 µg/ml, from about 100 µg/ml to about 1000 µg/ml, from about 100 µg/ml to about 500 µg/ml, or from about 100 µg/ml to about 250 µg/ml.

In some embodiments, the osmolyte comprises a carbohydrate or a sugar alcohol. In some embodiments, the carbohydrate is a monosaccharide or disaccharide. In some embodiments, the carbohydrate has 2, 3, 4, 5, 6, 7, or 8 carbons per monosaccharide unit. In certain embodiments, the carbohydrate is selected from the group consisting of glyceraldehyde, dihydroxyacetone, ribose, ribulose, glucose, fructose, galactose, or sucrose. In some embodiments, the sugar alcohol is selected from ethylene glycol, glycerol, erythritol, threitol, arabitol, xylitol, ribitol, galactitol, fucitol, iditol, inositol, sorbitol, or mannitol. Other examples of osmolytes include, but are not limited to, trimethylamine N-oxide (TMAO), dimethylsulfoniopropionate, trimethylglycine, sarcosine, betaine, glycerophosphorylcholine, myo-inositol, taurine, and *glycine*.

In some embodiments, the osmolyte comprises sucrose. In some embodiments, the sucrose is at a concentration of at least about 100 mM, at least about 150 mM, at least about 200 mM, at least about 250 mM, at least about 300 mM, at least about 350 mM, at least about 400 mM, at least about 450 mM, at least about 500 mM, at least about 550 mM, or at least about 600 mM, at least about 700 mM, at least about 800 mM, at least about 900 mM, at least about 1 M, at least about 1.1 M, at least about 1.2 M, at least about 1.3 M, at least about 1.4 M, at least about 1.5 M, at least about 1.6 M, at least about 1.7 M, at least about 1.8 M, at least about 1.9 M, at least about 2 M, at least about 2.5 M, at least about 3 M, at least about 3.5 M, at least about 4 M, at least about 4.5 M, or at least about 5 M. In some embodiments, the sucrose is at a concentration from about 100 mM to about 1 M, from about 200 mM to about 1 M, from about 300 mM to about 1 M, from about 400 mM to about 1 M, from about 500 mM to about 1 M, from about 100 mM to about 1.5 M, from about 200 mM to about 1.5 M, from about 300 mM to about 1.5 M, from about 400 mM to about 1.5 M, from about 500 mM to about 1.5 M, from 500 mM to about 2 M, from 500 mM to about 2.5 M, from 500 mM to about 3 M, from 500 mM to about 3.5 M, from 500 mM to about 4 M, from 500 mM to about 5 M. In some embodiments, the sucrose is at a concentration of about 100 mM, about 150 mM, about 200 mM, about 250 mM, about 300 mM, about 350 mM, about 400 mM, about 450 mM, about 500 mM, about 550 mM, about 600 mM, about 650 mM, about 700 mM, about 750 mM, about 800 mM, about 900 mM, about 1 M mM, about 1.2 M, about 1.5 M, about 2 M, about 2.5 M, about 3 M, about 3.5 M, about 4 M, about 4.5 M, or about 5 M.

In some embodiments, the osmolyte comprises mannitol. In some embodiments, the mannitol is at a concentration of at least about 100 mM, at least about 150 mM, at least about 200 mM, at least about 250 mM, at least about 300 mM, at least about 350 mM, at least about 400 mM, at least about 450 mM, at least about 500 mM, at least about 550 mM, or at least about 600 mM, at least about 700 mM, at least about 800 mM, at least about 900 mM, at least about 1 M, at least about 1.1 M, at least about 1.2 M, at least about 1.3 M, at least about 1.4 M, at least about 1.5 M, at least about 1.6 M, at least about 1.7 M, at least about 1.8 M, at least about 1.9 M, at least about 2 M, at least about 2.5 M, at least about 3 M, at least about 3.5 M, at least about 4 M, at least about 4.5 M, or at least about 5 M. In some embodiments, the mannitol is at a concentration from about 100 mM to about 1 M, from about 200 mM to about 1 M, from about 300 mM to about 1 M, from about 400 mM to about 1 M, from about 500 mM to about 1 M, from about 100 mM to about 1.5 M, from about 200 mM to about 1.5 M, from about 300 mM to about 1.5 M, from about 400 mM to about 1.5 M, from about 500 mM to about 1.5 M, from 500 mM to about 2 M, from 500 mM to about 2.5 M, from 500 mM to about 3 M, from 500 mM to about 3.5 M, from 500 mM to about 4 M, from 500 mM to about 5 M. In some embodiments, the mannitol is at a concentration of about 100 mM, about 150 mM, about 200 mM, about 250 mM, about 300 mM, about 350 mM, about 400 mM, about 450 mM, about 500 mM, about 550 mM, about 600 mM, about 650 mM, about 700 mM, about 750 mM, about 800 mM, about 900 mM, about 1 M mM, about 1.2 M, about 1.5 M, about 2 M, about 2.5 M, about 3 M, about 3.5 M, about 4 M, about 4.5 M, or about 5 M.

In some embodiments, the osmolyte comprises glycerol. In some embodiments, the glycerol is at a concentration of at least about 100 mM, at least about 150 mM, at least about 200 mM, at least about 250 mM, at least about 300 mM, at least about 350 mM, at least about 400 mM, at least about 450 mM, at least about 500 mM, at least about 550 mM, or at least about 600 mM, at least about 700 mM, at least about 800 mM, at least about 900 mM, at least about 1 M, at least about 1.1 M, at least about 1.2 M, at least about 1.3 M, at least about 1.4 M, at least about 1.5 M, at least about 1.6 M, at least about 1.7 M, at least about 1.8 M, at least about 1.9 M, at least about 2 M, at least about 2.5 M, at least about 3 M, at least about 3.5 M, at least about 4 M, at least about 4.5 M, or at least about 5 M. In some embodiments, the glycerol is at a concentration from about 100 mM to about 1 M, from about 200 mM to about 1 M, from about 300 mM to about 1 M, from about 400 mM to about 1 M, from about 500 mM to about 1 M, from about 100 mM to about 1.5 M, from about 200 mM to about 1.5 M, from about 300 mM to about 1.5 M, from about 400 mM to about 1.5 M, from about 500 mM to about 1.5 M, from 500 mM to about 2 M, from 500 mM to about 2.5 M, from about 500 mM to about 3 M, from 500 mM to about 3.5 M, from about 500 mM to about 4 M, from 500 mM to about 5 M. In some embodiments, the glycerol is at a concentration of about 100 mM, about 150 mM, about 200 mM, about 250 mM, about 300 mM, about 350 mM, about 400 mM, about 450 mM, about 500 mM, about 550 mM, about 600 mM, about 650 mM, about 700 mM, about 750 mM, about 800 mM, about 900 mM, about 1 M mM, about 1.2 M, about 1.5 M, about 2 M, about 2.5 M, about 3 M, about 3.5 M, about 4 M, about 4.5 M, or about 5 M.

In some embodiments, the polynucleotide is a DNA, an RNA, or a DNA/RNA hybrid. In some embodiments, the polynucleotide is single-stranded or double-stranded. In some embodiments, the polynucleotide is at least 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides (nt) in length. In some embodiments, the polynucleotide is at least 100, at least 200, at least 300, at least 400, at least 500, at least 600, at least 700, at least 800, at least 900, or at least 1000 nt in length. In some embodiments, the polynucleotide is from about 18 to about 1000 nt, from about 20 to about 1000 nt, from about 25 to about 1000 nt, from about 30 to about 1000 nt, from about 35 to about 1000 nt, from about 40 to about 1000 nt, from about 45 to about 1000 nt, from about 50 to about 1000 nt, from about 60 to about 1000 nt, from about 70 to about 1000 nt, from about 80 to about 1000 nt, from about 90 to about 1000 nt, from about 100 to about 1000 nt, from about 20 to about 50 nt, from about 20 to about 100 nt, from about 20 to about 200 nt, from about 20 to about 300 nt, or from about 20 to about 500 nt in length.

In some embodiments, the polynucleotide is a double-stranded RNA. In some embodiments, the double-stranded RNA is double-stranded RNA formed by intramolecular hybridization. In other embodiments, the double-stranded RNA is double-stranded RNA formed by intermolecular hybridization.

In some embodiments, the target gene comprises a coding sequence, a non-coding sequence, or a combination thereof. In some embodiments, the target gene comprises a non-coding sequence selected from the group consisting of a 5'UTR sequence, a 3'UTR sequence, a promoter, an intron sequence, and combinations thereof.

In some embodiments, the target gene is an endogenous gene or a transgene. In some embodiments, the target gene is (a) an essential gene for maintaining the growth or life of the plant; (b) a gene encoding a protein that provide herbicide resistance to the plant; or (c) a gene that transcribes to an RNA regulatory agent. In some embodiments, the essential gene is selected from: genes involved in DNA or RNA replication, gene transcription, RNA-mediated gene regulation, protein synthesis, energy production, cell division, and any combination thereof.

In certain embodiments, the gene is involved in the synthesis of a protein selected from: a 5-enolpyruvylshikimate-3-phosphate synthase (EPSPS), a glyphosate oxidoreductase (GOX), a glyphosate decarboxylase, a glyphosate-N-acetyl transferase (GAT), a dicamba monooxygenase, a phosphinothricin acetyltransferase, a 2,2-dichloropropionic acid dehalogenase, an acetohydroxyacid synthase, an acetolactate synthase, a haloarylnitrilase, an acetyl-coenzyme A carboxylase, a dihydropteroate synthase, a phytoene desaturase, a protoporphyrin IX oxygenase, a hydroxyphenylpyruvate dioxygenase, a para-aminobenzoate synthase, a glutamine synthase, a cellulose synthase, a beta-tubulin, and a serine hydroxymethyltransferase.

In some embodiments, the polynucleotide is a RNA regulatory molecule. In certain embodiments, the RNA regulatory molecule is selected from: a promoter, a micro RNA (miRNA), a miRNA precursor, a small interfering RNA (siRNA), a Piwi interacting RNA (piRNA), a trans-acting siRNA, an aptamer, and a riboswitch.

In some embodiments, the target gene is an endogenous gene of an invertebrate plant pest or a pathogen of the plant. In some embodiments, the invertebrate plant pest is an insect, a nematode, or a mite. In some embodiments, the invertebrate plant pest is an insect. In some embodiments, the pathogen is a viral pathogen, a fungal pathogen, or a bacterial pathogen.

In some embodiments, the plant is a weed or a volunteer plant. In some embodiments, the weed or volunteer plant is selected from: pigweed, velvetleaf, waterhemp, prickly lettuce, dandelion, alfalfa, corn, soybean, canola, cotton, sugar beet, sugarcane, wheat, rice, and a vegetable. In some embodiments, the weed or volunteer plant is growing in a field of crop plants. In one embodiment, the field comprises a refuge area.

In some embodiments, crop plants are selected from: corn, soybean, cotton, canola, sugar beet, alfalfa, sugarcane, rice, wheat, a fruit crop, a vegetable crop, or any combination thereof.

In some embodiments, the mixture or composition that is applied to the plant or a part thereof is dissolved or dispersed in an aqueous solution. In some embodiments, the aqueous solution has a pH from about 5 to about 9.

In some embodiments, the mixture or composition is a gel, a powder, an emulsion, a suspension, a cream, an aerosol, a paste, a spray, a solid dispersion, or a supersaturated solution.

In some embodiments, the mixture or composition is applied to a leaf of the plant. In some embodiments, the mixture is applied to the leaf via infiltration.

In some embodiments, the concentration of the polynucleotide in the mixture or composition to be applied is from about 0.01 µg/ml to about 1000 µg/ml. In certain embodiments, the concentration of the polynucleotide in the mixture or composition to be applied is from about 0.01 µg/ml to about 500 µg/ml, from about 0.01 µg/ml to about 250 µg/ml, from about 0.01 µg/ml to about 100 µg/ml, from about 0.01 µg/ml to about 50 µg/ml, from about 0.01 µg/ml to about 25 µg/ml, from about 0.01 µg/ml to about 10 µg/ml, from about 0.01 µg/ml to about 5 µg/ml, from about 0.01 µg/ml to about 1 µg/ml, from about 0.01 µg/ml to about 0.5 µg/ml, from about 0.01 µg/ml to about 0.1 µg/ml, from about 0.05 µg/ml to about 1000 µg/ml, from about 0.05 µg/ml to about 500 µg/ml, from about 0.05 µg/ml to about 250 µg/ml, from about 0.05 µg/ml to about 100 µg/ml, from about 0.05 µg/ml to about 50 µg/ml, from about 0.05 µg/ml to about 25 µg/ml, from about 0.05 µg/ml to about 10 µg/ml, from about 0.05 µg/ml to about 5 µg/ml, from about 0.05 µg/ml to about 1 µg/ml, from about 0.05 µg/ml to about 0.5 µg/ml, from about 0.05 µg/ml to about 0.1 µg/ml, from about 0.1 µg/ml to about 1000 µg/ml, from about 0.1 µg/ml to about 500 µg/ml, from about 0.1 µg/ml to about 250 µg/ml, from about 0.1 µg/ml to about 100 µg/ml, from about 0.1 µg/ml to about 50 µg/ml, from about 0.1 µg/ml to about 25 µg/ml, from about 0.1 µg/ml to about 10 µg/ml, from about 0.1 µg/ml to about 5 µg/ml, from about 0.1 µg/ml to about 1 µg/ml, from about 1 µg/ml to about 1000 µg/ml, from about 1 µg/ml to about 500 µg/ml, from about 1 µg/ml to about 250 µg/ml, from about 1 µg/ml to about 100 µg/ml, from about 1 µg/ml to about 50 µg/ml, from about 1 µg/ml to about 25 µg/ml, from about 1 µg/ml to about 10 µg/ml, from about 1 µg/ml to about 5 µg/ml, from about 10 µg/ml to about 1000 µg/ml, from about 10 µg/ml to about 500 µg/ml, from about 10 µg/ml to about 250 µg/ml, from about 10 µg/ml to about 100 µg/ml, from about 10 µg/ml to about 50 µg/ml, from about 10 µg/mi to about 25 µg/ml, from about 50 µg/ml to about 1000 µg/ml, from about 50 µg/ml to about 500 µg/ml, from about 50 µg/ml to about 250 µg/ml, from about 50 µg/ml to about 100 µg/ml, from about 100 µg/ml to about 1000 µg/ml, from about 100 µg/ml to about 500 µg/ml, or from about 100 µg/ml to about 250 µg/ml.

In some embodiments, the final concentration of the polynucleotide on the leaf is from about 0.01 µg/ml to about 1000 µg/ml. In certain embodiments, the concentration of the polynucleotide on the leaf is from about 0.01 µg/ml to about 500 µg/ml, from about 0.01 µg/ml to about 250 µg/ml, from about 0.01 µg/ml to about 100 µg/ml, from about 0.01 µg/ml to about 50 µg/ml, from about 0.01 µg/ml to about 25 µg/ml, from about 0.01 µg/ml to about 10 µg/ml, from about 0.01 µg/ml to about 5 µg/ml, from about 0.01 µg/ml to about 1 µg/ml, from about 0.01 µg/ml to about 0.5 µg/ml, from about 0.01 µg/ml to about 0.1 µg/ml, from about 0.05 µg/ml to about 1000 µg/ml, from about 0.05 µg/ml to about 500 µg/ml, from about 0.05 µg/ml to about 250 µg/ml, from about 0.05 µg/ml to about 100 µg/ml, from about 0.05 µg/ml to about 50 µg/ml, from about 0.05 µg/ml to about 25 µg/ml, from about 0.05 µg/ml to about 10 µg/ml, from about 0.05 µg/ml to about 5 µg/ml, from about 0.05 µg/ml to about 1 µg/ml, from about 0.05 µg/ml to about 0.5 µg/ml, from about 0.05 µg/ml to about 0.1 µg/ml, from about 0.1 µg/ml to about 1000 µg/ml, from about 0.1 µg/ml to about 500 µg/ml, from about 0.1 µg/ml to about 250 µg/ml, from about 0.1 µg/ml to about 100 µg/ml, from about 0.1 µg/ml to about 50 µg/ml, from about 0.1 µg/ml to about 25 µg/ml, from about 0.1 µg/ml to about 10 µg/ml, from about 0.1 µg/ml to about 5 µg/ml, from about 0.1 µg/ml to about 1 µg/ml, from about 1 µg/ml to about 1000 µg/ml, from about 1 µg/ml to about 500 µg/ml, from about 1 µg/ml to about 250 µg/ml, from about 1 µg/ml to about 100 µg/mi, from about 1 µg/ml to about 50 µg/ml, from about 1 µg/ml to about 25 µg/ml, from about 1 µg/ml to about 10 µg/ml, from about 1 µg/ml to about 5 µg/ml, from about 10 µg/ml to about 1000 µg/ml, from about 10 µg/ml to about 500 µg/ml, from about 10 µg/ml to about 250 µg/ml, from about 10 µg/ml to about 100 µg/ml, from about 10 µg/ml to about 50 µg/ml, from about 10 µg/nil to about 25 µg/ml, from about 50 µg/ml to about 1000 µg/ml, from about 50 µg/ml to about 500 µg/ml, from about 50 µg/ml to about 250 µg/ml, from about 50 µg/ml to about 100 µg/ml, from about 100 µg/ml to about 1000 µg/ml, from about 100 µg/ml to about 500 µg/ml, or from about 100 µg/ml to about 250 µg/ml.

In some embodiments, the mixture is re-applied at least once, at least twice, or at least three times onto the surface of the leaf at an interval of at least 24 hours after the initial application. In some embodiments, the interval of the reapplied mixture is from about 24 hours to about 14 days.

In some embodiments, at least 10%, at least 20%, at least 30%, at least 40%, at least 50%, at least 60%, at least 70%, at least 80%, or at least 90% of the total area on the surface of the leaf is in contact with the mixture.

In some embodiments, the polynucleotide can be detected in the plant cell at least about 12 hours, at least about 24 hours, at least about 48 hours, or at least about 72 hours after the application of the mixture. In some embodiments, the polynucleotide can be detected by a method selected from Southern blotting, Northern blotting, PCR, RT-PCR, in situ hybridization, a fluorescence-based assay system, a chemiluminenscence-based assay system, a phosphorescence-based assay system, and any combination thereof.

In some embodiments, the concentration of the polynucleotide in the plant cell is at least 10 femptomolar (fM), or at least 10 picomolar (pM) after 24 hours. In some embodiments, the concentration of the polynucleotide in the plant cell is at least 50 pM, 100 pM, 500 pM, or 1 micromolar (µM) after 24 hours, after 48 hours, or after 72 hours.

In some embodiments, the mRNA level of the target gene is decreased relative to the level prior to the application of the polynucleotide. In some embodiments, the mRNA level of the target gene is decreased at least 12 hours, at least 24 hours, at least 48 hours, or at least 72 hours after the application of the polynucleotide.

In some embodiments, the target gene is an endogenous gene or a transgene of the plant, and the mRNA level of the target gene in the plant cell is decreased by at least 10%, at least 20%, at least 30%, at least 40%, at least 50%, at least 60%, at least 70%, at least 80%, at least 90%, or at least 95% relative to the level in the plant cell prior to the application of the polynucleotide. In some embodiments, the mRNA level is measured by a method selected from Northern blotting, RT-PCR, in situ hybridization, a fluorescence-based assay system, a chemiluminenscence-based assay system, a phosphorescence-based assay system, and any combination thereof. In some embodiments, the mRNA level of the target gene is decreased in a plant cell that is not in direct contact with the mixture at the time of the application.

In some embodiments, the target gene is an endogenous gene of an invertebrate plant pest or a plant pathogen, and the mRNA level of the target gene in an invertebrate plant pest or a plant pathogen that has internalized a part of the plant or part thereof is decreased by at least 10%, at least 20%, at least 30%, at least 40%, at least 50%, at least 60%, at least 70%, at least 80%, at least 90%, or at least 95% relative to the level in an invertebrate plant pest or a plant pathogen that has not internalized a part of the plant or part thereof. In some embodiments, the mRNA level of the target gene is decreased at least 12 hours, at least 24 hours, at least 48 hours, or at least 72 hours after the internalization by the invertebrate plant pest of plant pathogen.

In some embodiments, the mRNA of the target gene is cleaved by an Argonaute family protein. In some embodiments, the mRNA of the target gene is cleaved in the cytoplasm of the plant cell.

In some embodiments, after the application of the polynucleotide, the plant or part thereof shows a phenotypic change relative to a plant or part thereof not applied with the polynucleotide. In some embodiments, the phenotypic change is selected from leaf withering, bleaching, size reduction, growth inhibition, and any combination thereof. In some embodiments, the plant or part thereof shows the phenotypic change at least 24 hours, at least 48 hours, or at least 72 hours after the application of the polynucleotide. In some embodiments, the plant or part thereof does not show a phenotypic change at least 24 hours, at least 48 hours, or at least 72 hours after the application of the polynucleotide relative to a plant or part thereof not applied with the polynucleotide.

In some embodiments, the target gene encodes a protein that provides resistance to a chemical herbicide, the method in the present disclosure further comprises applying the chemical herbicide to the plant or part thereof.

In some embodiments, the mixture or composition that is applied to the plant or a part thereof further comprises a surfactant. In some embodiments, the surfactant is selected from: organosilicone surfactants, pelagronic acid, ethylene oxide surfactants, polysorbate, cetostearyl alcohol, cetyl alcohol, oleyl alcohol, stearyl alcohol, cocamide DEA, cocamide MEA, polyalkylglucoside, decyl glucoside, lauryl glucoside, octyl glucoside, monolaurin, poloxamer, sorbitan monostearate, sorbitan tristearate, bio-surfactants, and any combination thereof. Examples of commercially available nonionic surfactants include, but are not limited to, silicones such as Silwet® L-77 from Momentive, alkyl polyglucosides, available under the Agnique PG brand from BASF (formerly Cognis), ethoxylated fatty acids and alcohols, available from Lamberti, BASF, Croda, Akzo Nobel, Stepan, and many other manufacturers, and ethoxylated sorbitan esters available under the Tween tradename from Croda and as Alkest® TW from Oxiteno. In some embodiments, the surfactant is at a concentration of about 0.5% to about 10%. In some embodiments, the surfactant in the composition is at a concentration of about 0.01% to about 10%, about 0.05% to about 10%, about 0.1% to about 10%, about 0.2% to about 10%, about 0.5% to about 10%, about 1% to about 10%, about 0.01% to about 5%, about 0.05% to about 5%, about 0.1% to about 5%, about 0.2% to about 5%, about 0.5% to about 5%, about 1% to about 5%, about 0.05% to about 2%, about 0.1% to about 2%, or about 0.5% to about 2%. In some embodiments, the surfactant is at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 1.2%, about 1.5%, about 2%, about 3%, about 4%, about 5%, about 6%, about 7%, about 8%, about 9%, or about 10%.

In some embodiments, the surfactant is a bio-surfactant. A bio-surfactant is a surface-active substance synthesized by living cells. In some embodiments, the bio-surfactant is produced by a microorganism. In certain embodiments, the bio-surfactant is produced by a bacterium or a fungi. Examples of bio-surfactants include, but are not limited to, Lipopeptides (e.g. *Bacillus subtilis* surfactin), glycolipids (e.g., di- and mono-rhamnolipids from *P. aeruginosa*), 1',4'-Sophorolactone 6',6'-diacetate (e.g., from *Candida* sp.), trehalose lipids (from *Rhodococcus* spp.) and mannosylerythritol lipids (*Candida* antartica). In some embodiments, the bio-surfactant is selected from a lipopeptide, a glycolipid, a trehalose lipid, a mannosylerythritol lipid, 1',4'-Sophorolactone 6',6'-diacetate, and any combination thereof.

In some embodiments, the mixture or composition that is applied to the plant or a part thereof further comprises Endoporter. In some embodiments, the Endoporter is at a concentration of about 1 μM to 1 mM. In certain embodiments, the Endoporter is at a concentration of about 1 to about 5 μM, about 1 to about 10 μM, about 1 to about 20 μM, about 1 to about 30 μM, about 1 to about 40 about 1 to about 50 μM, about 1 to about 100 μM, about 1 to about 200 μM, about 1 to about 300 μM, about 1 to about 500 μM, about 5 to about 10 μM, about 5 to about 20 about 5 to about 50 μM, about 5 to about 100 μM, about 20 to about 50 μM, about 20 to about 100 μM, about 20 to about 200 μM, about 100 to about 200 μM, about 100 to about 500 μM, about 5 μM, about 10 μM, about 15 μM, about 20 μM, about 25 μM, about 30 μM, about 35 JIM, about 40 μM, about 45 μM, about 50 μM, about 60 μM, about 70 μM, about 80 μM, about 90 μM, about 100 μM, about 150 μM, about 200 μM, about 250 μM, about 300 μM, about 350 μM, about 400 μM, about 450 μM, about 500 μM, about 600 μM, about 700 μM, about 800 μM, or about 900 μM.

A polynucleotide composition as disclosed herein may further comprise agents to facilitate transfer of a polynucleotide into a plant cell include agents that increase permeability of the exterior of the plant or that increase permeability of plant cells to oligonucleotides or polynucleotides. Such agents include, but are not limited to, a chemical agent, a physical agent, or combinations thereof. Chemical agents for conditioning includes, but are not limited to, (a) surfactants, (b) an organic solvents or an aqueous solutions or aqueous mixtures of organic solvents, (c) oxidizing agents, (d) acids, (e) bases, (f) oils, (g) enzymes, or combinations thereof. A transferring agent contemplated herein can further comprise a humectant or a chelating agent.

Exemplary agents or treatments for conditioning a plant for permeation include, but are not limited to, emulsions, reverse emulsions, liposomes, and other micellar-like compositions. Further exemplary agents or treatments include counter-ions or other molecules that are known to associate with nucleic acid molecules, e.g., inorganic ammonium ions, alkyl ammonium ions, lithium ions, polyamines such as spermine, spermidine, or putrescine, and other cations. Organic solvents useful in conditioning a plant to permeation by polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e.g., plant-sourced oils, crop oils, paraffinic oils, polyol-fatty acid esters, and oils with short-chain molecules modified with amides or polyamines such as polyethyleneimine or N-pyrrolidine. A polynucleotide composition as disclosed herein can further comprise an organic or inorganic salt. In one aspect the salt is an ammonium salt, for example, ammonium sulfate.

Exemplary surfactants which facilitate the uptake of a dsRNA into plant cells include sodium or lithium salts of fatty acids (such as tallow or tallowamines or phospholipids) and organosilicone surfactants. Further exemplary surfactants include organosilicone surfactants including nonionic organosilicone surfactants, e.g., trisiloxane ethoxylate surfactants or a silicone polyether copolymer such as a copolymer of polyalkylene oxide modified heptamethyl trisiloxane and allyloxypolypropylene glycol methylether (commercially available as Silwet L-77 surfactant). When Silwet L-77 surfactant is used to treat plant seed, leaves or other surfaces, concentrations in the range of about 0.015 to about 2% by weight (wt %) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 wt %) are efficacious in preparing a seed, leaf or other plant surface for transfer of a polynucleotide into plant cells.

Exemplary physical agents facilitating the uptake of a dsRNA into plant cells include, but are not limited to, (a) abrasives such as carborundum, corundum, sand, calcite, pumice, garnet, and the like, (b) nanoparticles such as carbon nanotubes, or (c) a physical force. Carbon nanotubes are disclosed by Kam et al. (2004) J. Am. Chem. Soc., 126 (22):6850-6851, Liu et al. (2009) Nano Lett., 9(3):1007-1010, and Khodakovskaya et al. (2009) ACS Nano, 3(10): 3221-3227. Physical force agents can include heating, chilling, the application of positive pressure, or ultrasound treatment.

A cationic polymer is a polymer having a multiplicity of ionic or ionizable functional groups having a positive charge. A non-exhaustive list of examples of cationic polymers include hexamethrine bromide, polyethyleneimine, polylysine and corresponding copolymers with neutral amino acids, aminosilanes, γ-amino-propyltriethoxysilane (GAPS), cationic dendrimers, star polymers, and polyvinylamine.

A polynucleotide composition of the instant disclosure can comprise a cationic polymer at an effective concentration selected from the group consisting of about 0.001, 0.005, 0.01, 0.02, 0.04, 0.04, 0.06, 0.08, 0.1, 0.12, 0.14, 0.14, 0.16, 0.18, 0.2, 0.22, 0.24, 0.24, 0.26, 0.28, 0.3, 0.32, 0.34, 0.34, 0.36, 0.38, 0.4, 0.42, 0.44, 0.44, 0.46, 0.48, 0.5, 0.52, 0.54, 0.54, 0.56, 0.58, 0.6, 0.7, 0.8, 0.9, 1.0, 1.2, 1.5, 1.8, 2.0 µg/µl.

A polynucleotide composition of the instant disclosure can comprise a sugar at an effective concentration selected from the group consisting of about 100, 200, 250, 300, 250, 400, 450, 500, 550, 600, 650, 700, 750, 800, 850, and 900 µg/µl.

In one aspect, a polynucleotide composition can comprise a disaccharide. In another aspect, a polynucleotide composition can comprise a sugar molecule selected from the group consisting of sucrose, mannose, mannitol, sorbitol, lactose, trehalose and salicin.

In another aspect, a polynucleotide composition of the instant disclosure can further comprise a cell-penetrating peptide which is a peptide that comprises a short (about 12-30 residues) amino acid sequence or functional motif that confers the energy-independent (e.g., non-endocytotic) translocation properties associated with transport of the membrane-permeable complex across the plasma and/or nuclear membranes of a cell. Cell-penetrating peptides used in the membrane-permeable complex of the present disclosure preferably comprise at least one non-functional cysteine residue, which is either free or derivatized to form a disulfide link with a dsRNA that has been modified for such linkage. Representative amino acid motifs conferring such properties are listed in U.S. Pat. No. 6,348,185, the contents of which are expressly incorporated herein by reference. Cell-penetrating peptides of the present disclosure preferably include, but are not limited to, penetratin, transportan, pls1, TAT(48-60), pVEC, MTS, and MAP.

A polynucleotide composition of the instant disclosure can be applied to a plant or plant part by any method known in the art, e.g., spraying, drenching, soaking, or coating with a powder, emulsion, suspension, or solution.

The instant disclosure also provides plants and parts thereof treated with a polynucleotide composition as disclosed herein.

Any commercially or scientifically valuable plant is envisaged in accordance with some aspects of the disclosure. Plants that are particularly useful in the methods of the disclosure include all plants which belong to the super family Viridiplantae, in particular monocotyledonous and dicotyledonous plants including a fodder or forage legume, ornamental plant, food crop, tree, or shrub selected from the list comprising Acacia spp., Acer spp., *Actinidia* spp., *Aesculus* spp., Agathis *australis, Albizia amara, Alsophila tricolor, Andropogon* spp., *Arachis* spp, *Areca catechu, Astelia fragrans, Astragalus* titer, Baikiaea plurijuga, *Betula* spp., *Brassica* spp., Bruguiera gymnorrhiza, Burkea *africana, Butea frondosa, Caclaba farinosa*, Calliandra spp, *Camellia sinensis, Canna indica, Capsicum* spp., *Cassia* spp., Centroema *pubescens*, Chacoorneles spp., Cinnamornum *cassia, Coffea arabica*, Colophospermum mopane, Coronillia varia, Cotoneaster *serotina, Crataegus* spp., *Cucumis* spp., *Cupressus* spp., Cyathea *dealbata, Cydonia oblonga, Cryptomeria japonica*, Cymbopogon spp., *Cynthea dealbata, Cydonia oblonga, Dalbergia* monetaria, Davallia *divaricata*, Desmodiunz spp., Dicksonia squarosa, Diheteropogon arnplectens, Dioclea *Dolichos* spp., *Dorycnium* rectum, *Echinochloa pyramidalis*, Ehraffia spp., *Eleusine coracana*, Eragrestis spp., *Erythrina* spp., *Eucalyptus* spp., Euclea *schimperi*, Eulalia vi/losa, Pagopyrum spp., Feijoa sellowlana, Fragaria spp., Flemingia spp., Freycinetia banksli, Geranium *thunbergii*, GinAgo *biloba, Glycine javanica*, Gliricidia spp., *Gossypium* hirsutunz, Grevillea spp., Guibourtia coleosperma, Hedysarum spp., Henzaffhia *altissima, Heteropogon contoffits, Hordeum vulgare, Hvparrhenia rufa, Hypericum erectum*, Hypeffhelia dissolute, Indigo incanzata, Iris spp., Leptarrhena pyrolifblia, Lespediza spp., Lettuca spp., Leucaena leucocephala, Loudetia simplex, Lotonus bainesli, Lotus spp., Macrotyloma axillare, Malus spp., *Manihot esculenta, Medicago Metasequoia* glyptostroboide.s, Musa sapientum, Nicotianum spp., *Onobrychis* spp., Ornithopus spp., *Oryza* spp., Peltophorunz *africanum, Pennisetum* spp., Pet-sea *gratissima, Petunia* spp., *Phaseolus* spp., *Phoenix canariensis, Phornziwn cookianum, Photinia* spp., *Picea glauca, Pinus* spp., *Pisum* sativam, Podocarpus *totara*, Pogonarthria fleckii, Pogonaffhria *squarrosa, Populus* spp., Prosopis *cineraria, Pseudotsuga menziesii, Pterolobium stellatum*, Pyru.s. *communis, Quercus* spp., Rhaphiolepsis *umbellata, Rhopalostylis sapida, Rhus natalensis, Ribes grossularia, Ribes* spp., *Robinia pseudoacacia*, Rosa spp., *Rubus* spp., Salix spp., Schyzachyrium sanguineum, Sciadopitys vellicillata, *Sequoia sempervirens, Sequoiadendron giganteutn, Sorghum bicolor, Spinacia* spp., *Sporobolus.fimbriatus, Stiburus alopecuroides, Stylosanthos humilis*, Tadehagi spp, *Taxodium* distichunz, Themeda *triandra*, Trifblium spp., *Triticum* spp., *Tsuga heterophylla, Vaccinium* spp., *Vicia* spp., *Vitis vinifera, Watsonia* pyramidata, Zantedeschia *aethiopica, Zea* nzays, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barley, rye, oat, peanut, pea, lentil and alfalfa, cotton, rapeseed, canola, pepper, sunflower, tobacco, eggplant, *eucalyptus*, a tree, an ornamental plant, a perennial grass and a forage crop. Alternatively algae and other non-Viridiplantae can be used for the methods of the present disclosure.

According to some aspects of the disclosure, the plant used by the method of the disclosure is a crop plant including, but not limited to, cotton, *Brassica* vegetables, oilseed rape, sesame, olive tree, palm oil, banana, wheat, corn or maize, barley, alfalfa, peanuts, sunflowers, rice, oats, sugarcane, soybean, turf grasses, barley, rye, *sorghum*, sugar cane, chicory, lettuce, tomato, zucchini, bell pepper, eggplant, cucumber, melon, watermelon, beans, hibiscus, okra, apple, rose, strawberry, chili, garlic, pea, lentil, canola, mums, *Arabidopsis*, broccoli, cabbage, beet, *quinoa*, spinach, squash, onion, leek, tobacco, potato, sugarbeet, *papaya*, pineapple, mango, *Arabidopsis thaliana*, and also plants used in horticulture, floriculture or forestry, such as, but not limited to, poplar, fir, *eucalyptus*, pine, an ornamental plant, a perennial grass and a forage crop, coniferous plants, moss, algae, as well as other plants available on the Internet at, for example, nationmaster.com/encyclopedia/Plantae.

According to a specific aspect, the plant is selected from the group consisting of corn, rice, wheat, tomato, cotton and *sorghum*. In certain aspects, the plant is a corn plant. In certain aspects, the plant is a rice plant. In certain aspects, the plant is a wheat plant. In certain aspects, the plant is a cotton plant. In certain aspects, the plant is a *sorghum* plant.

Introduction of the compositions of the present disclosure can be performed to any organs/cells of the plant (as opposed to seeds) using conventional delivery methods such as particle bombardment, grafting, soaking and the like.

Compositions and methods of the disclosure are useful for modulating the expression of an endogenous or transgenic target gene in a plant cell. In various embodiments, a target gene includes coding (protein-coding or translatable) sequence, non-coding (non-translatable) sequence, or both coding and non-coding sequence. Compositions of the disclosure can include polynucleotides and oligonucleotides designed to target multiple genes, or multiple segments of one or more genes. The target gene can include multiple consecutive segments of a target gene, multiple non-consecutive segments of a target gene, multiple alleles of a target gene, or multiple target genes from one or more species. Examples of target genes include endogenous plant genes and transgenes expressed in plant cells. Other examples of target genes include endogenous genes of plant viral pathogens or endogenous genes of invertebrate plant pests.

Target genes can include genes encoding herbicide-tolerance proteins, non-coding sequences including regulatory RNAs, and essential genes, which are genes necessary for sustaining cellular life or to support reproduction of an organism. Embodiments of essential genes include genes involved in DNA or RNA replication, gene transcription, RNA-mediated gene regulation, protein synthesis, energy production, and cell division. One example of a compendium of essential genes is described in Zhang et al. (2004) Nucleic Acids Res., 32:D271-D272, and is available at tubic.tju. edu.cn/deg/; version DEG 5.4 lists 777 essential genes for *Arabidopsis thaliana*. Examples of essential genes include translation initiation factor (TIF) and ribulose-1,5-bisphosphate carboxylase oxygenase (RuBisCO). Target genes can include genes encoding transcription factors and genes encoding enzymes involved in the biosynthesis or catabolism of molecules in plants such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin.

It is appreciated that certain features of the disclosure, which are, for clarity, described in the context of separate aspects, may also be provided in combination in a single aspect. Conversely, various features of the disclosure, which are, for brevity, described in the context of a single aspect, may also be provided separately or in any suitable subcombination or as suitable in any other described aspect of the disclosure. Certain features described in the context of various aspects are not to be considered essential features of those aspects, unless the aspect is inoperative without those elements. Various aspects and aspects of the present disclosure as delineated hereinabove and as claimed in the claims section below find experimental support in the following examples.

EXAMPLES

Example 1: PEI/MMg Mediated dsRNA Transfection of Intact Plant Cells Using dsRNA/PEI/MMg Formulation BY-2 GFP suspension cells were treated with dsRNA/PEI/MMg formulation in 'one step' treatment to deliver dsRNA into intact plant cells. Test sample compositions used for treatment are presented in Table 1. The triggers used were Control (SEQ ID NO:3/SEQ ID NO:4) and GFP22-3 (SEQ ID NO:1/SEQ ID NO:2).

TABLE 1

Experimental design for BY-2 GFP Suspension Cell Treatment

| Test Sample | Description | RNA (µg) | Rep | RNA vol (7.49 µg/µl) | PEI (5 µg/ml) | H₂O | MMg/ MS |
|---|---|---|---|---|---|---|---|
| 1 | Control/PEI/ MMg | 60 | 2 | 16.02 | 24.00 | 59.98 | 500.00 |
| 2 | GFP22-3/PEI/ MMg_W5 | 60 | 2 | 16.02 | 24.00 | 59.98 | 500.00 |
| 3 | Control/PEI/ MS | 60 | 2 | 16.02 | 24.00 | 59.98 | MS, 500.00 |
| 4 | GFP22-3/PEI/ MS_W5 | 60 | 2 | 16.02 | 24.00 | 59.98 | MS, 500.00 |

For each treatment, 500 µl of BY-2 GFP suspension cells at late exponential growth phase were collected by centrifugation and washed once with MS growth medium (Murashige and Skoog medium BY-2 suspension cells). The liquid was removed from the cell pellet and the cells resuspended in 250 µl of each of the four test samples were incubated at room temperature (approximately 25° C.) for 30 minutes. Cells were then washed twice with 5 milliliters (ml) of W5 solution (154 mM NaCl, 125 mM CaCl₂), 5 mM KCl, 2 mM MES pH5.7) and suspended in W1 (0.5 M Mannitol, 4 mM MES pH5.7, 20 mM KCl) and incubated overnight at room temperature. After overnight incubation, RNA was extracted for analysis.

Figure 1:
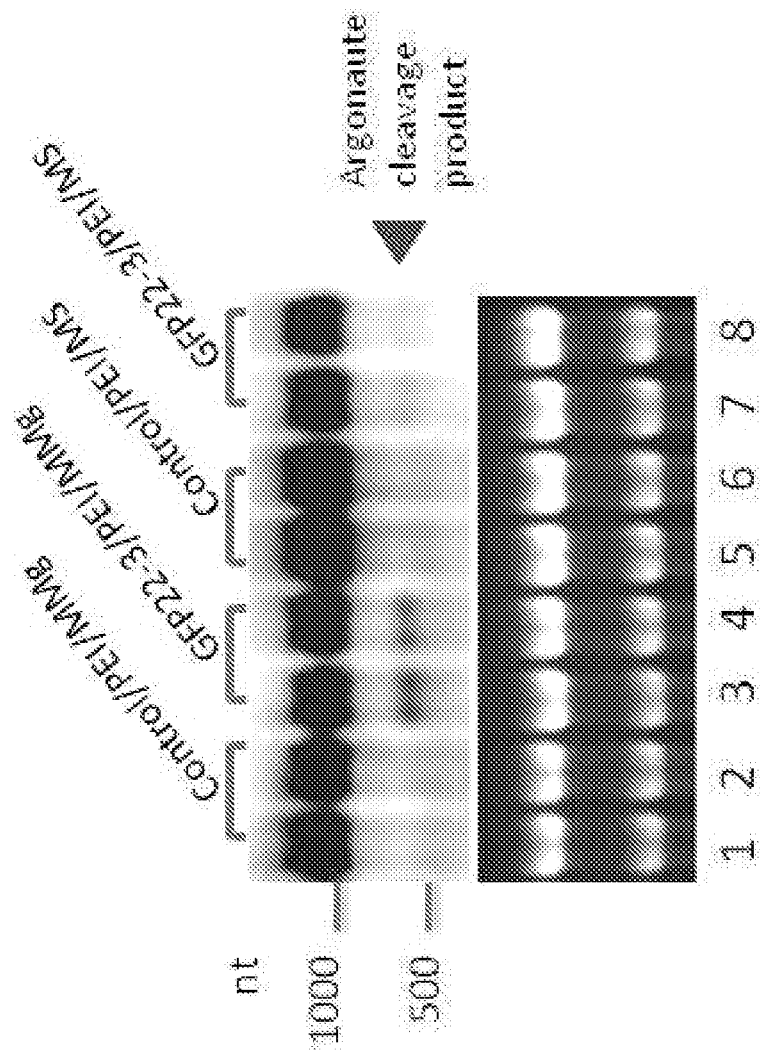
FIG. 1: Northern analysis of treated BY_2 cells after PEI mediated transfection. Extracts were analyzed for the ability to produce a sliced fragment of the RNA which is cleaved by Argonaute (AGO). A fragment was evident in the GFP22-3 (SEQ ID NO:1/SEQ ID NO:2) treated transfection carried out in the presence of PEI and MMg. A weaker band was also visible in the lanes treated with GFP22-3/PEI/MS.

The results of Northern blot analysis using 5 µg of total RNA per sample is presented in FIG. 1. The probe was a 279 base pair (bp) digoxygenin (DIG) labeled RNA probe targeting the 5' region of the target GFP message. As shown in FIG. 1, GFP22-3/PEI/MMg treated samples had a strong argonaute cleavage product (samples/lanes 3, 4) and GFP22-3/PEI/MS treated samples had a weak argonaute cleavage product (samples/lanes 7, 8). The results demonstrate that PEI and MMg based formulation provided one step delivery of a 22 mer dsRNA trigger into intact BY-2 suspension cells.

Example 2: Hexamethrine Bromide/MM400 or Hexamethrine Bromide/SM400 Mediated dsRNA Transfection of Plant Cells BY-2 GFP suspension cells were treated with dsRNA/Hexamethrine bromide/MM400 or dsRNA/hexamethrine bromide/SM400 formulations in 'one step' treatment to deliver dsRNA into intact plant cells. dsRNA delivery efficiency was significantly increased.

TABLE 2

Experimental Design for Hexamethrine bromide mediated Transfection

| Test Sample | Description | RNA (ug) | Volume (µl) | Hexa-methrine bromide (ug) | Hexa-methrine bromide volume (µl) | Buffer |
|---|---|---|---|---|---|---|
| 1 | M411/Polyb/MM400 | 60 | 8 | 180 | 18 | 274, MM400 |
| 2 | GFP22-3/Polyb/MM400 | 60 | 8 | 180 | 18 | 274, MM400 |
| 3 | GFP22-3/Polyb/SM400 | 60 | 8 | 180 | 18 | 274, SM400 |

For each treatment, 500 µl of BY-2 GFP suspension cells at late exponential growth phase were collected by centrifugation and washed once with MS growth medium (Murashige and Skoog medium BY-2 suspension cells). The liquid was removed from the cell pellet and the cells were resuspended in 150 µl of each of the four test samples. M411 (SEQ ID NO:3/SEQ ID NO:4) is a non specific dsRNA control. GFP22-3 (SEQ ID NO:1/SEQ ID NO:2) is a 22 mer dsRNA targeting GFP in BY-2 GFP cell line. A total of 30 µg of RNA was used for each sample and two replicates of each were tested. The test samples were prepared in either MM400 (400 mM Mannitol, 4 mM MES, pH5.7) or SM400 (400 mM sucrose, 4 mM MES, pH5.7). After resuspension, the samples were incubated at room temperature (approximately 25° C.) for one hour. Cells were then washed twice with 5 milliliters (ml) of W5 solution (154 mM NaCl, 125 mM CaCl$_2$), 5 mM KCl, 2 mM MES pH5.7) and suspended in W1 (0.5 M Mannitol, 4 mM MES pH5.7, 20 mM KCl) and incubated overnight at room temperature. After overnight incubation, RNA was extracted for analysis.

Figure 2:
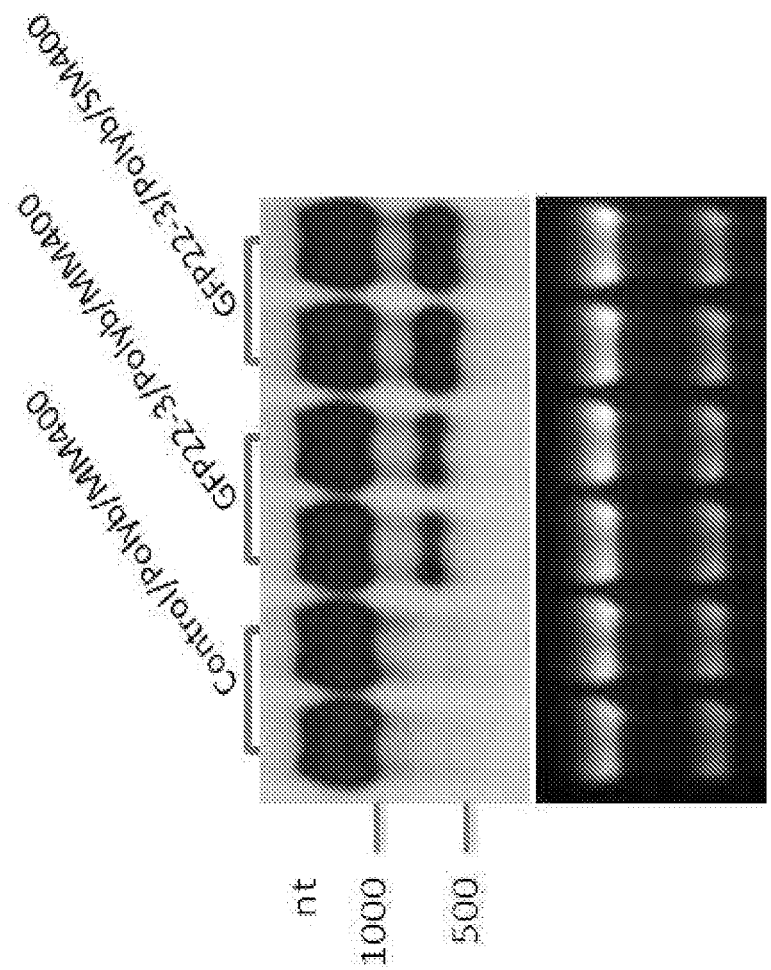
FIG. 2: Northern analysis of treated BY_2 Cells after Polybrene® (Polyb or PB) mediated transfection. Extracts were analyzed after overnight incubation in treatments with either control (non-specific dsRNA, SEQ ID NO:3/SEQ ID NO:4) or GFP22-3 (SEQ ID NO:1/SEQ ID NO:2) for the ability to produce a sliced fragment of RNA which is cleaved by Argonaute. The extracts from the BY_2 transfection treated with GFP22-3/Polyb/SM400 had a stronger AGO cleavage product than those from the transfection with GFP22-3/Polyb/MM400.
Figure 3:
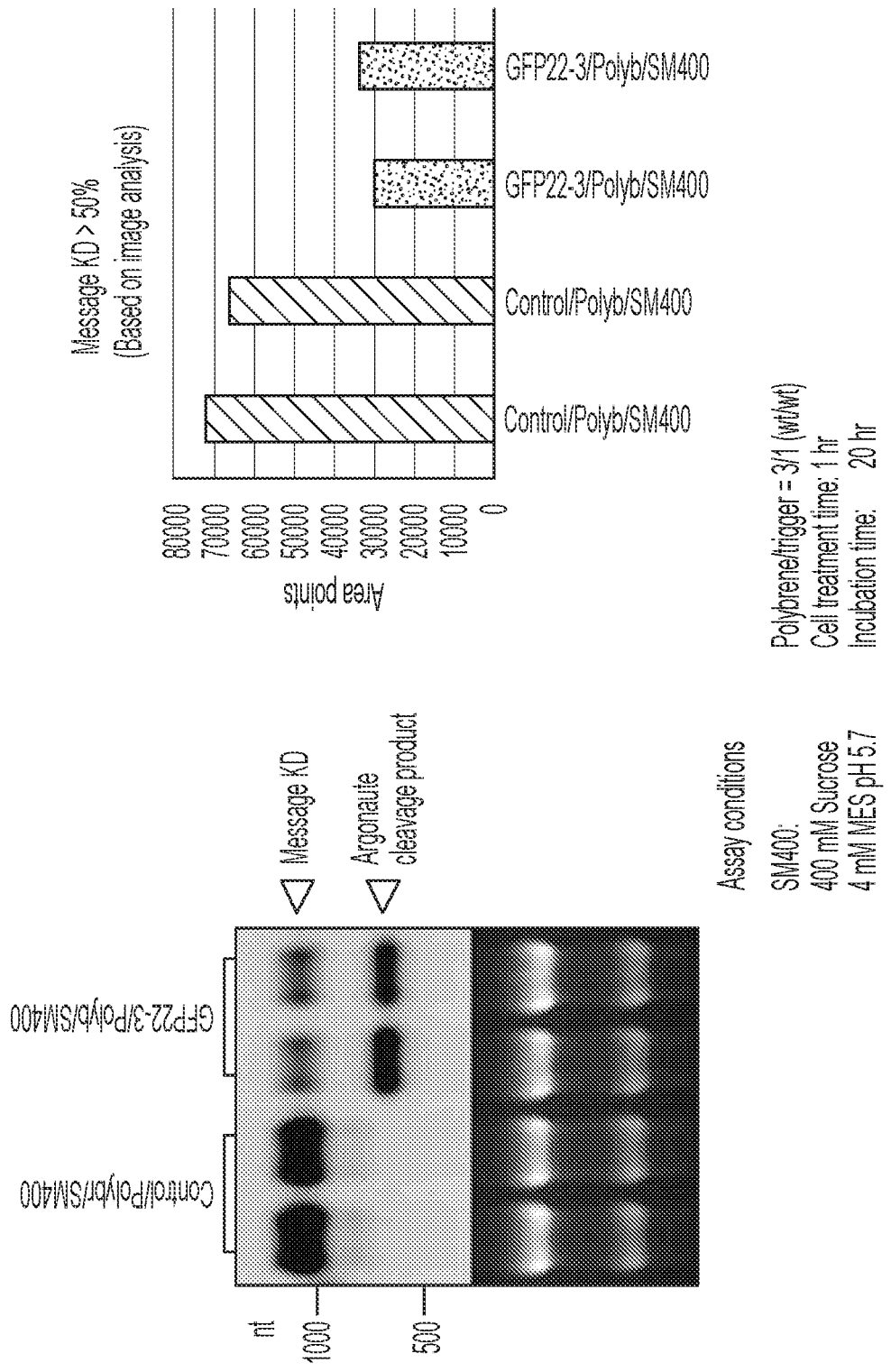
FIG. 3: Analysis of AGO knockdown in Polybrene® mediated transfected cells. The left panel shows a Northern blot analysis of a transfection using the control non-specific RNA (SEQ ID NO:3/SEQ ID NO:4) in BY_2 cells treated with Polybrene® in the presence of SM400 (400 mM sucrose, 4 mM MES, pH5.7) or the GFP22-3 (SEQ ID NO:1/SEQ ID NO:2) dsRNA. A clear reduction in message levels and concomitant increase in AGO cleavage product is visible for the GFP22-3 lanes. On the right side of the Figure the message knockdown is quantified based on image analysis. A reduction in GFP message of >50% is measured in the GFP22-3 dsRNA treated lanes.
Figure 4:
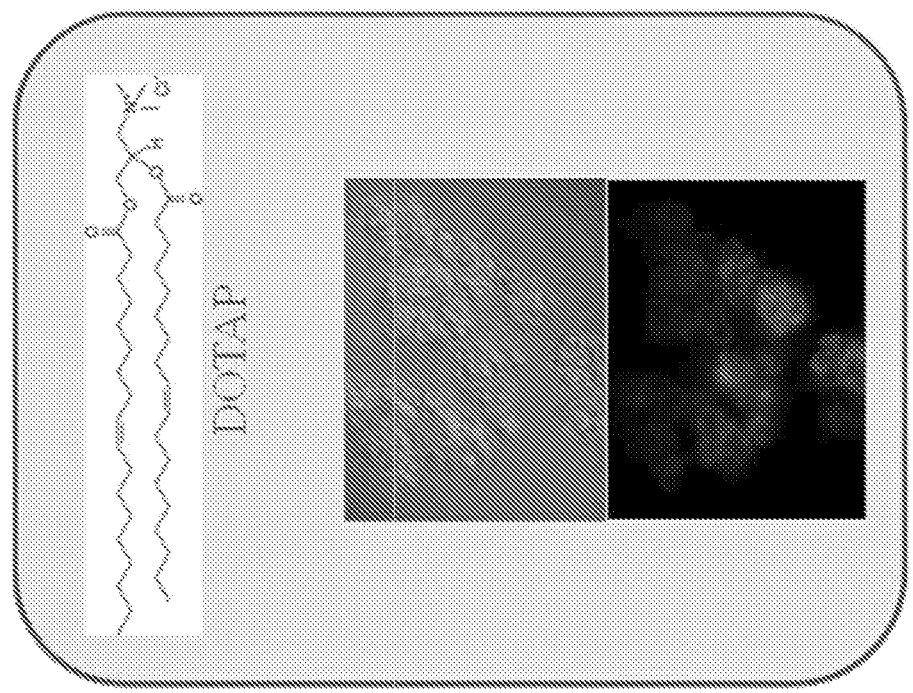
FIG. 4: Effect of DOTAP on dsRNA uptake in BY2 cells. The image shows uptake of pHrodo labeled RNA in BY2 cells. pHRodo labeled siRNA were complexed with DOTAP. The complexes were added to BY2 cells and incubated overnight. After incubation, the cells were washed and resuspended in 0.01% trypan blue to quench remaining extracellular fluorescence. Total cell associated fluorescence was then measured using a fluorometer, and the cells were photographed using epifluorescent microscopy.

The results of Northern blot analysis using 5 µg of total RNA per sample is presented in FIG. 2. The probe is a 279 base pair (bp) digoxygenin (DIG) labeled RNA probe targeting the 5' region of the target GFP message. As shown in FIG. 2, GFP22-3/Polyb/MM400 treated samples had a strong argonaute cleavage product (samples/lanes 3, 4) and GFP22-3/Polyb/SM400 treated samples had a stronger argonaute (AGO) cleavage product (samples/lanes 7, 8). In a repeat experiment shown in FIG. 3, both message knockdown and AGO cleavage product were observed. The results demonstrate that hexamethrine bromide based formulations provided one step delivery of a 22 mer dsRNA trigger into intact BY-2 suspension cells. Using the method above, treatment of BY2 cells with DOTAP promoted dsRNA uptake as shown in FIG. 4.

Example 3. Hexamethrine Bromide/SM400 Mediated dsRNA Transfection of N. Benthamiana (16c) Plants N. Benthamiana (16c) plants were transfected by application of Hexamethrine bromide/SM400 to the intact leaves using the samples prepared as shown in Table 3. M411 (SEQ ID NO:3/SEQ ID NO:4) is a non specific dsRNA control. 16cGFP22-3 (SEQ ID NO:5/SEQ ID NO:6) and 16cGFP22-4 (SEQ ID NO:7/SEQ ID NO:8) are 22 mer dsRNAs targeting GFP in the BY-2_GFP cell line.

TABLE 3

Samples for Hexamethrine bromide/SM400 mediated dsRNA transfection of N. Benthamiana

| Index | Description | Reps (leaves) | Trig/rep | Infil vol/rep | Trig (ul) | Polyb (40 ug/ul) | SM400 |
|---|---|---|---|---|---|---|---|
| 1 | M411/polyb/SM400 | 6 | 30 | 150 | 24.03 | 13.5 | 862.47 |
| 2 | 16cGFP22-3/polyb/SM400 | 6 | 30 | 150 | 24.03 | 13.5 | 862.47 |
| 3 | 16cGFP22-4/polyb/SM400 | 6 | 30 | 150 | 24.03 | 13.5 | 862.47 |

Figure 5:
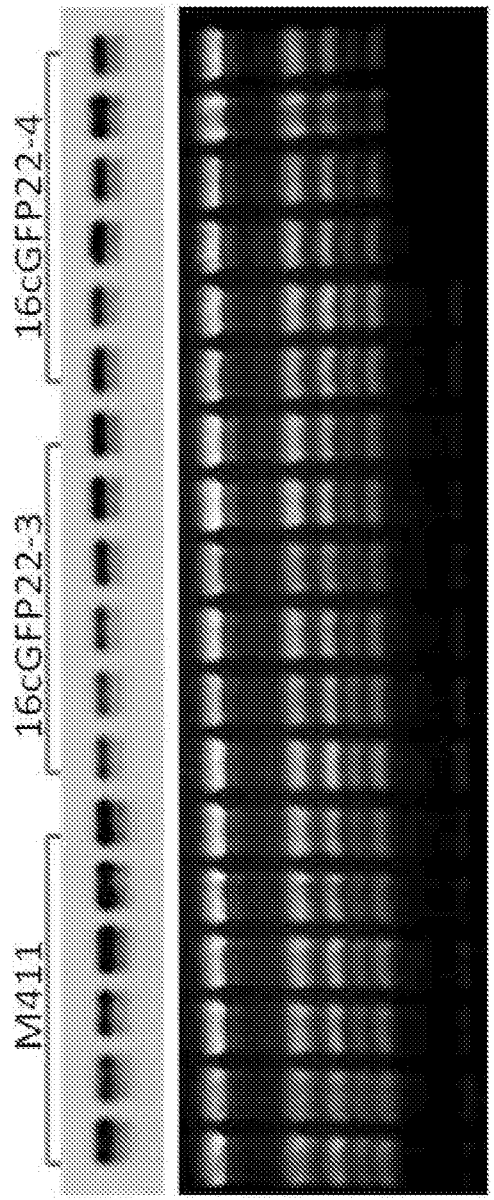
FIG. 5: Results of dsRNA infiltration of N. Benthamiana leaves. Extracts of infiltrated leaves using control dsRNA (M411; SEQ ID NO:3/SEQ ID NO:4) or 16cGFP22-3 (SEQ ID NO:5/SEQ ID NO:6) or 16cGFP22-4 (SEQ ID NO:7/SEQ ID NO:8) were analyzed after leaf infiltration with the formulations described in Table 3. In this first experiment no specific cleavage product for GFP was observed.
Figure 6:
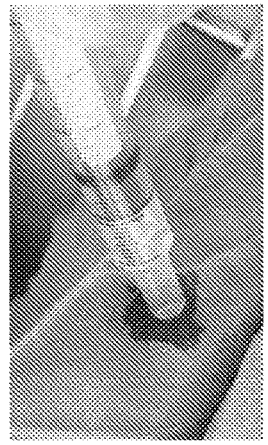
FIG. 6: Results of dsRNA infiltration of N. Benthamiana leaves. The left side of this Figure shows infiltration procedure using trigger (dsRNA)/Polyb and MM400 medium and the area collected at 20 hr post-transfection. The middle and right panel are Northern blot analyses of infiltrated leaf discs to check for the Argonaute (AGO) cleavage product. A slight band was observed in the GFP22-3 (SEQ ID NO:5/SEQ ID NO:6) treated extracts which was more prominent when no DMSO was used in the transfection procedure.
Figure 6:
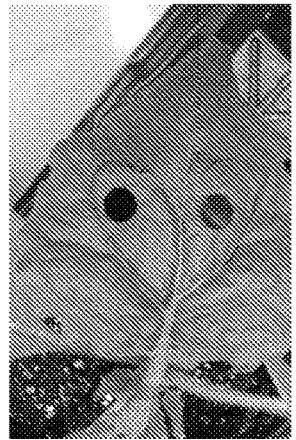
Figure 7:
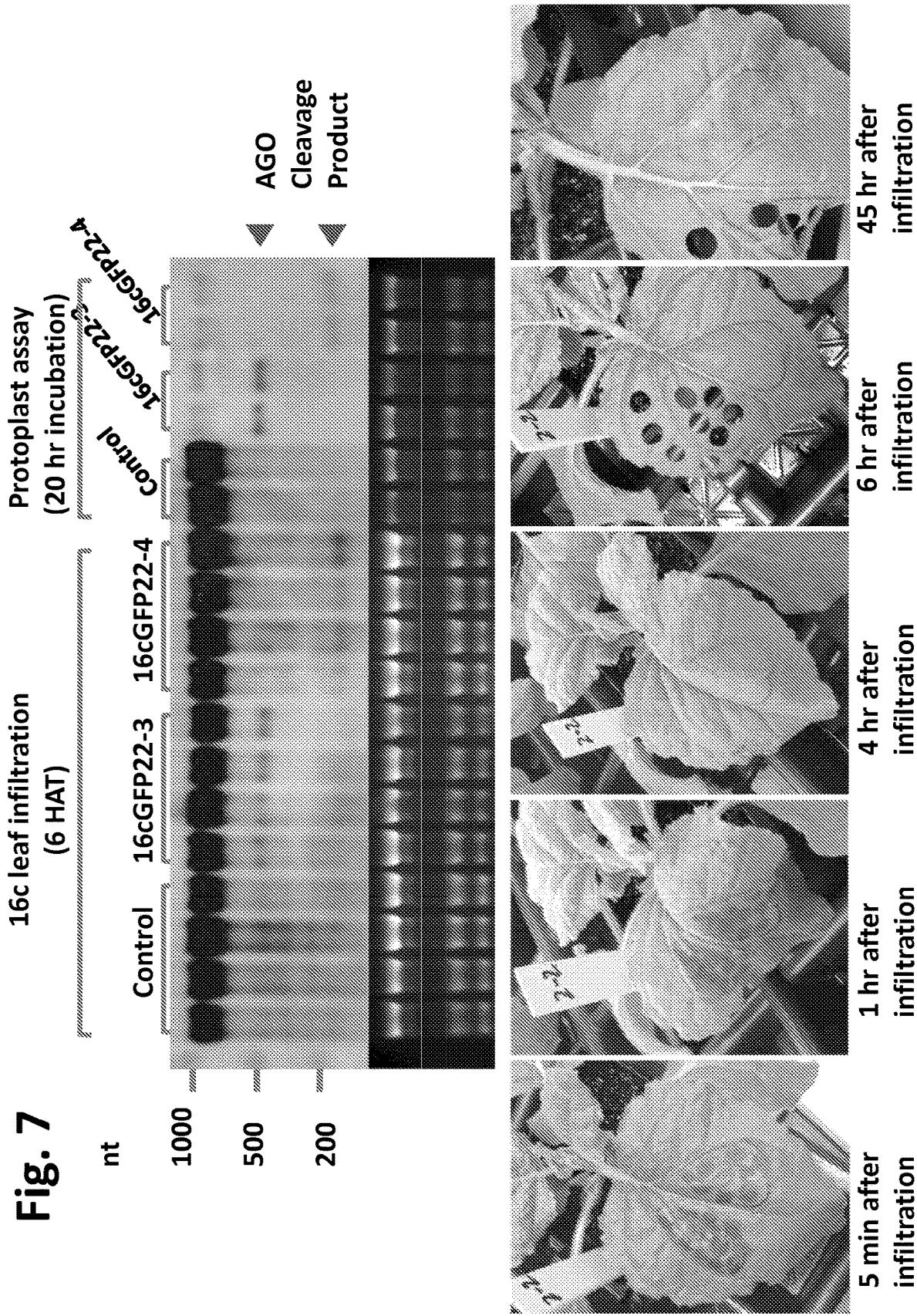
FIG. 7: Results of dsRNA infiltration of N. Benthamiana leaves after 6 hours. The top part of this Figure shows the Northern blot results of the infiltration after 6 hours or the protoplast assay at 20 hr post-transfection. AGO cleavage products (500 bp or 200 bp) are visible in the 16cGFP22-3 (SEQ ID NO:5/SEQ ID NO:6) or 16cGFP22-4 (SEQ ID NO:7/SEQ ID NO:8) but not in the control (SEQ ID NO:3/SEQ ID NO:4) treated samples.

Six leaves on each of two plants were infiltrated by treatment with the formulations. Leaf tissues were collected from the infiltrated spots 20 hours after infiltration and RNA was extracted and analyzed. The results of a Northern analysis are shown in FIG. 5. In a repeat experiment, the amount of message and the AGO cleavage product was observed FIG. 6. Additional replications present similar results after 6 hours of incubation after infiltration (FIG. 7). Both knockdown of the message and AGO cleavage products were observed for both 16cGFP22-3 and 16cGFP22-4 treated samples.

Example 4. Effects of Buffer, Concentration, pH on dsRNA Mediated Transfection by Trigger/Polyb/SM400

Figure 8:
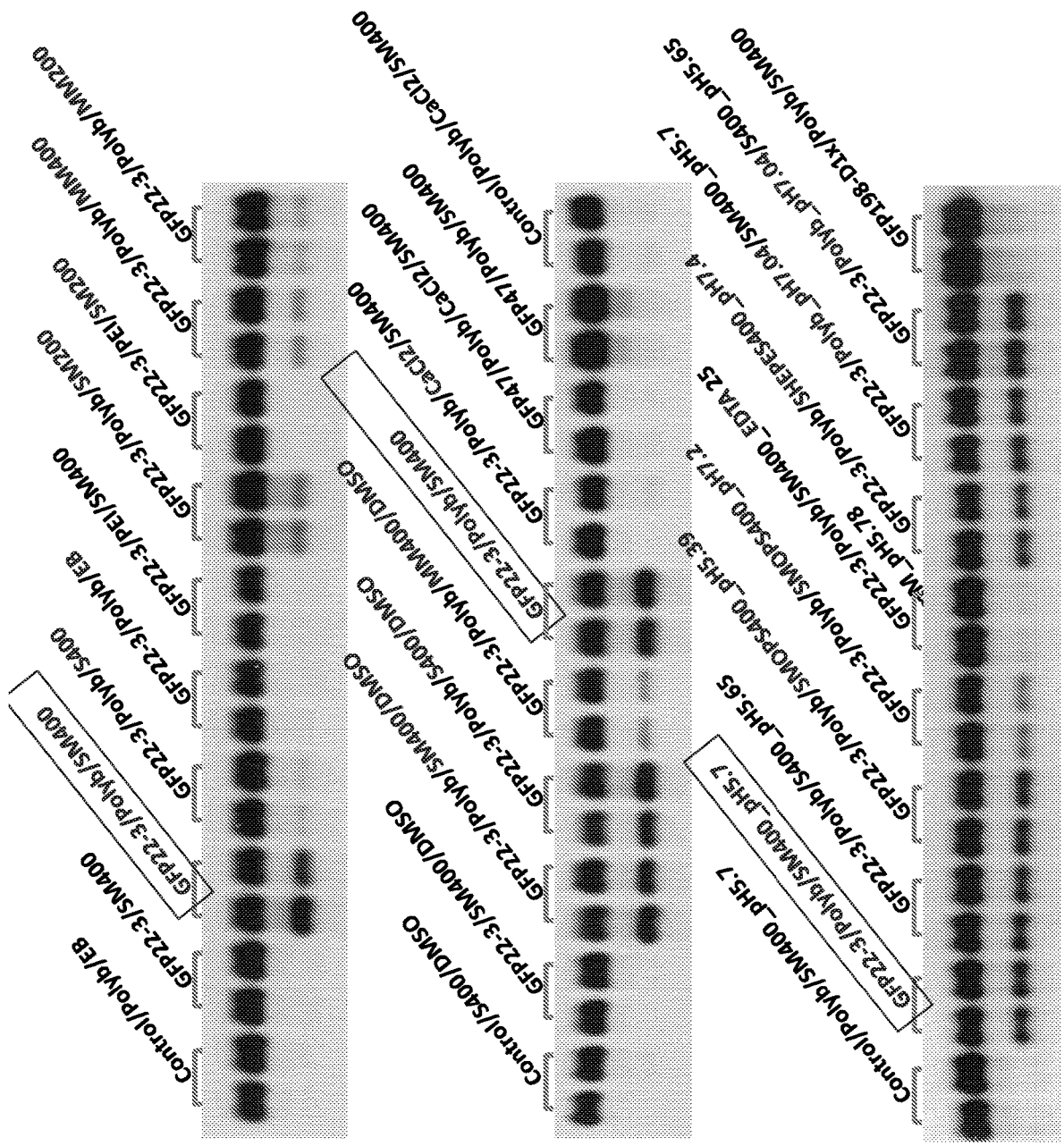
FIG. 8: Effects of buffer, concentration, and pH on transfection. In the top panel the buffer ingredients, concentration and various sugar concentrations were tested on the ability to detect a sliced fragment. In the middle panel further elements such as DMSO, $CaCl_2$) and combinations with different sucrose concentrations were analyzed. In the lower panel, the effect of varying pH and EDTA were analyzed.

Using the dsRNA infiltration methods presented in Example 3 above, the components of the transfection samples were systematically varied. The results are presented in FIG. 8. As shown in the top panel, the RNA trigger, cationic polymer, and a high concentration sugar solution were all essential in the formulation for transfection. Formulations with SM400 and hexamethrine bromide had best trigger delivery efficiency in current protocol. Formulations could be made with MES, MOPS, or HEPES and were effective at various pH at least from pH 5.7 to 7.5. EDTA may inhibit RNA cleavage suggesting a requirement for divalent cation though the presence of CaCl$_2$) may decrease delivery efficiency. DMSO could increase trigger delivery efficiency. The efficiency of trigger deliver may decrease as the size of the dsRNA is increased.

Example 5: Delivery of S1.EPSPS Midmer Trigger to Tomato Plants

Test samples were prepared as shown in Table 4. GFP (SEQ ID NO:1/SEQ ID NO:2) is a 21mer siRNA and was used as a non specific control in this experiment. The sequences for S1.EPSPS 22mer (SEQ ID NO:9/SEQ ID NO:10) and 48mer (SEQ ID NO:11) are shown in Table 5.

TABLE 4

Test samples for transfection of Tomato plants

| Index | Description | Reps | Vol/plant | Total vol | Trig con. | Trig/plant | Tot Trig vol | Tot Polyb | H2O | 2xMMg |
|---|---|---|---|---|---|---|---|---|---|---|
| 1 | GFP/Polyb | 18 | 4 | 72 | 7.49 | 3.5 | 8.41 | 4.725 | 26.46 | 32.4 |
| 2 | Sl EPSPS 22mer/polyb | 18 | 4 | 72 | 3.5 | 3.5 | 18 | 4.725 | 16.88 | 32.4 |
| 3 | Sl.EPSPS 48mer/polyb | 18 | 4 | 72 | 4.5 | 3.5 | 14 | 4.725 | 20.88 | 32.4 |

TABLE 5

Sl.EPSPS and Sl.CAC Trigger RNA sequences

| Species | Gene | Fwd Primer Synthesis Number | Rev Primer Synthesis Number | Probe Reporter | Fwd Primer Sequence | Rev Primer Sequence | Probe Sequence |
|---|---|---|---|---|---|---|---|
| Sl | Sl.EPSPS 3 | AM0017 | AM0018 | FAM | GAAGGGTCAGACTACTGCATAATCAC | TTCTGTGGTCATCATATGTATCAATCTC | CCACCAGAAAAGTTAAACGTA |
| Sl | Sl.CAC 3' | 37349 | 37350 | VIC | GACGACCCCCCTATAGATTTCTC | GCTCTTCCTCAATTCGAAACCA | TGTTTCGTCTTGTGTTGAC |

The germination and establishment media for tomato seeds was a modification of a ½ strength MS salts with full strength MS vitamins and supplemented with 15 g of sucrose as shown in Table 6. The pH was adjusted at to about pH 5.7.

TABLE 6

Germination and Establishment media

| Reagents | For 1 L of media |
|---|---|
| MS macro- and micro-nutrients | 2.2 g |
| MS vitamins (1000X) | 2.0 mL |
| Agar | 7.0 g |

Tomato seeds were disinfected by placing the seeds in a container and adding 70% ethanol. The tomato seeds were left for 1 min and rinsed once with sterile distilled water. In a transfer hood, seeds were sterilized in 2.6% NaCl plus 0.1% Tween20 for 20 min with occasional swirling. The seeds were rinsed 3-5 times with sterile distilled water and placed in a sterile filtered paper to absorb the excess of water. The resulting surface sterilized seeds were transferred to culture vessels containing the medium. The seeded culture vessels were grown in the dark at 21-25° C. for 2 days. After two days, the culture vessels were moved to a culture room and grown at 24-25° C. with a 16 hour photoperiod.

Figure 9:
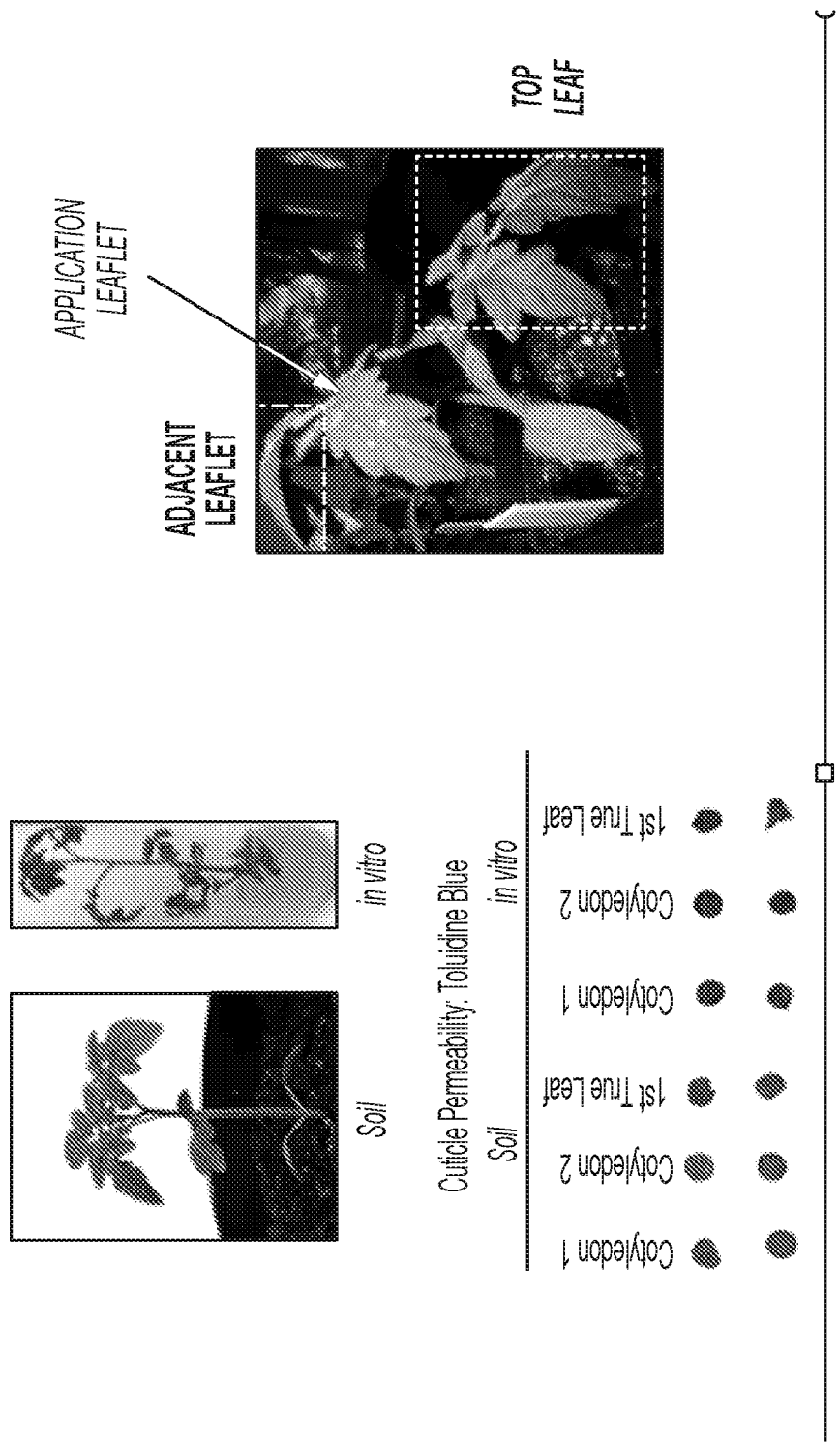
FIG. 9: Transfection of intact tomato leaves. Both wild type (Celebrity, in soil) or HP375 (GFP:LTP mutant, in vitro) tomato plants were transfected with Polybrene® formulation. A cuticle permeability test was conducted using Toluidine blue staining on both cotyledons or the first true leaf. Location of Application, adjacent and top leaf is also illustrated.
Figure 10A:
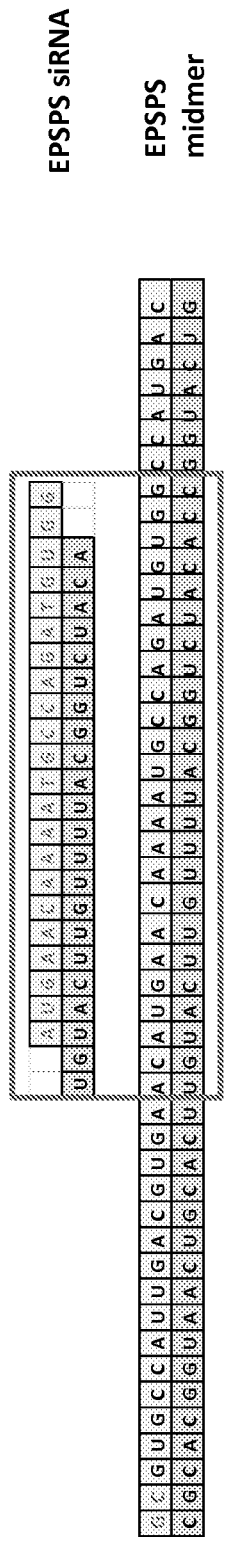
Figure 10B:
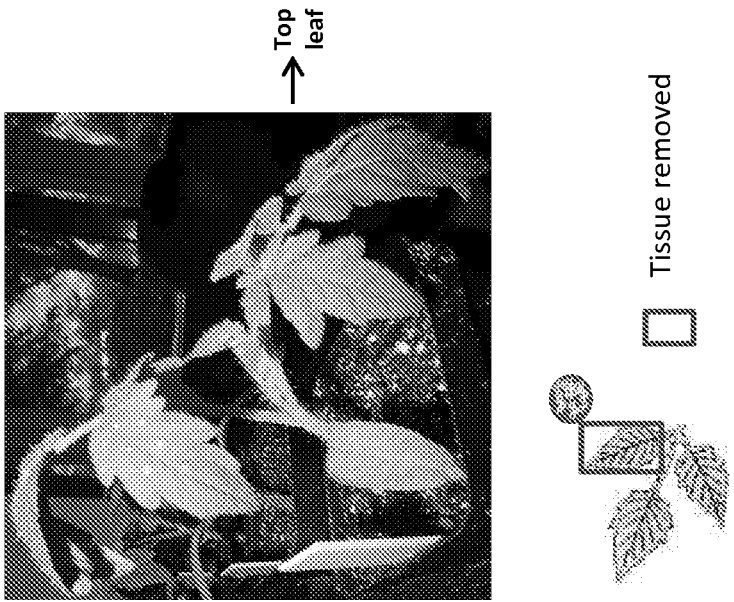
Figure 11A:
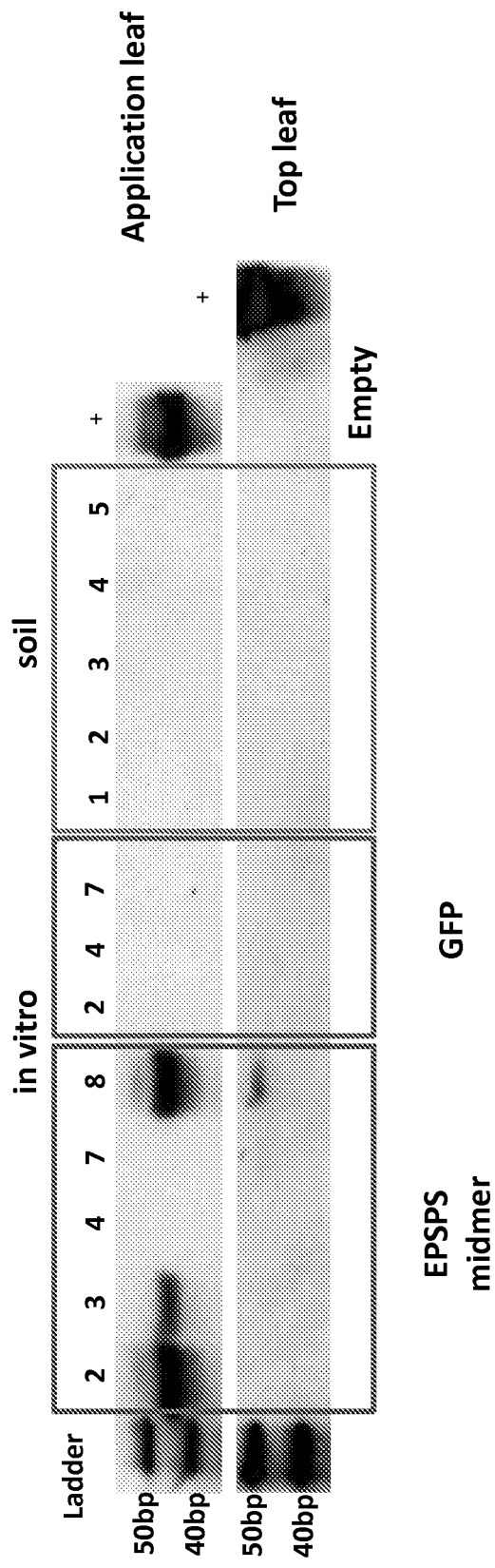

Four microliters (41.11) of each formulation (Table 5) were applied to a leaflet on the tomato plants. Two days after the application, the leaflet was removed. The rest of the leaflet was collected for molecular analysis and it was referred to as the "application leaf". The apical tissue was collected as well and was referred to as the "top leaf". The RNA was extracted by using Trizol RNA reagent (Invitrogen, Ca) and cDNA prepared for Tagman● analysis (see primers and probes below, FIG. 10). For small RNA Northern Blots, 7 μg of total RNA was used to detect the presence of the triggers in the tissue (FIG. 11). As shown in FIG. 9, FIG. 10 and FIG. 11, application of EPSPS 48mer to an intact application leave of a tomato plant resulted in the translocation of the EPSPS 48mer to the untreated top leaf. The presence of the EPSPS 48mer trigger was highly correlated with the knockdown of the gene.

Figure 12A:
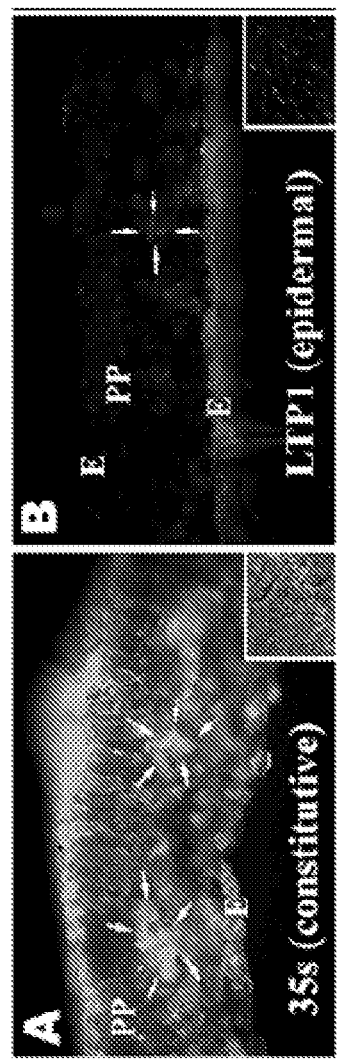
FIGS. 12A and 12B: Transfection of GFP triggers in tomato leaves.
Figure 12B:
Figure 12B:
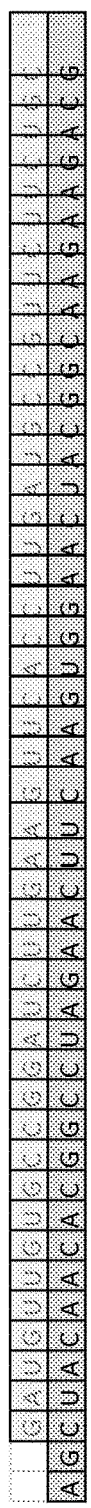

Example 6: GFP Midmer Trigger can Suppress the Expression Level of the Gene in Tomato Test samples were prepared as shown in Table 7. GFP (SEQ ID NO:1/SEQ ID NO:2) is a 21mer siRNA and was used as a non specific control in this experiment. The sequences are shown in FIG. 12.

TABLE 7

Experimental samples for transfection of intact tomato leaves

| Description | Reps | Vol/plant | Total vol | Trig con. | Trig/plant | Tot Trig vol | Tot Polyb | H2O | 2xMMg | Total |
|---|---|---|---|---|---|---|---|---|---|---|
| EPSPS/Polyb | 16 | 4 | 64 | 3.6 | 3.5 | 15.56 | 4.2 | 15.44 | 28.8 | 64 |
| LTPGFP21/polyb | 16 | 4 | 64 | 7.15 | 3.5 | 7.83 | 4.2 | 23.17 | 28.8 | 64 |
| 48mer/polyb | 16 | 4 | 64 | 8.17 | 3.5 | 6.85 | 4.2 | 24.15 | 28.8 | 64 |

Figure 13:
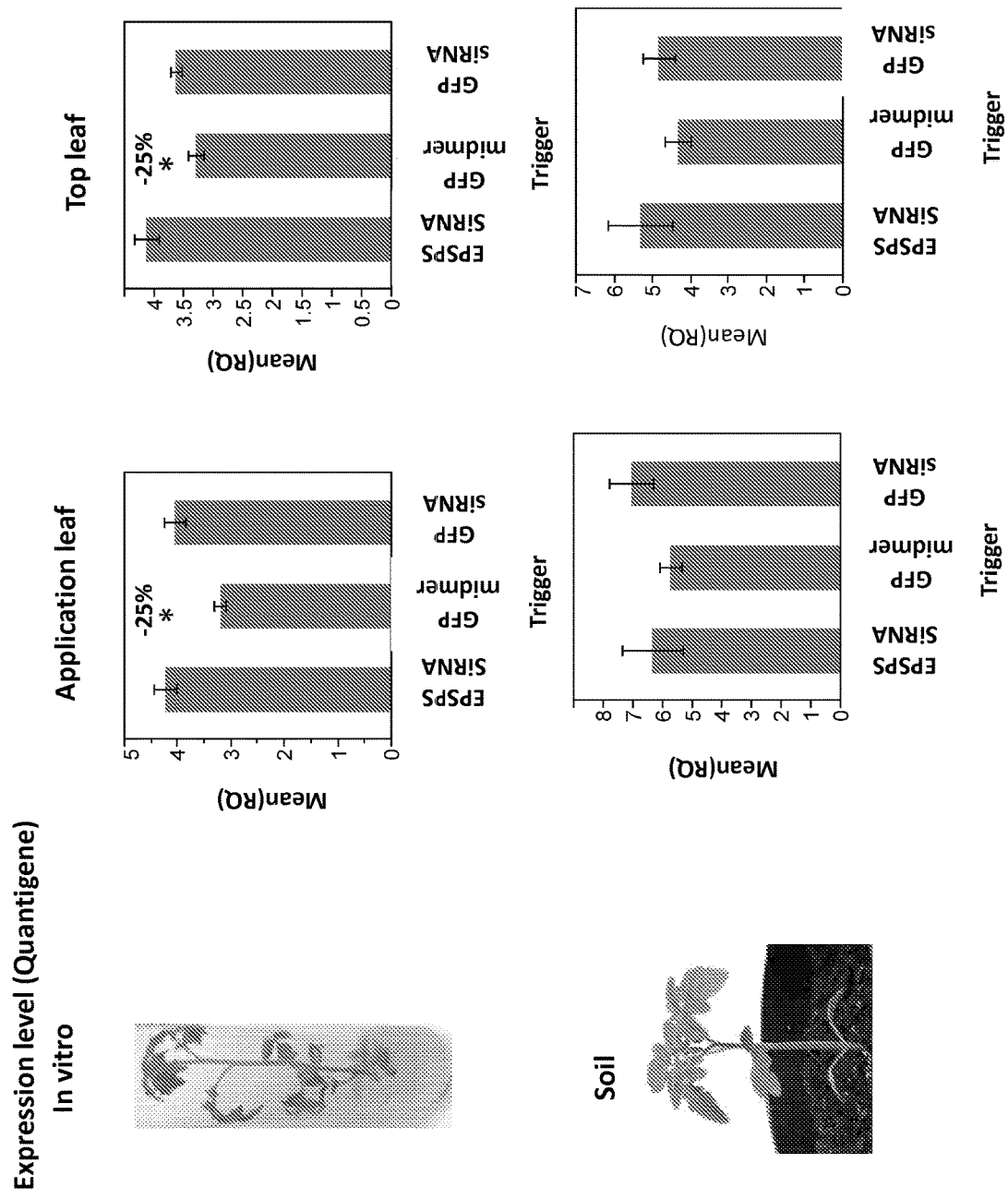
FIG. 13: Transfection of intact tomato leaves results in GFP knockdown. Tomato was grown in vitro in a small culture tube or in soil as illustrated in the Figure. Levels of GFP midmer, GFP siRNA or EPSPS siRNA were analyzed using Quantigene® for both the application leaf or the top leaf in both treatments. A significant reduction of 25% in GFP message levels was observed in both application and top leaves of treatments using GFP midmer for the plantlets grown in vitro.
Figure 14A:
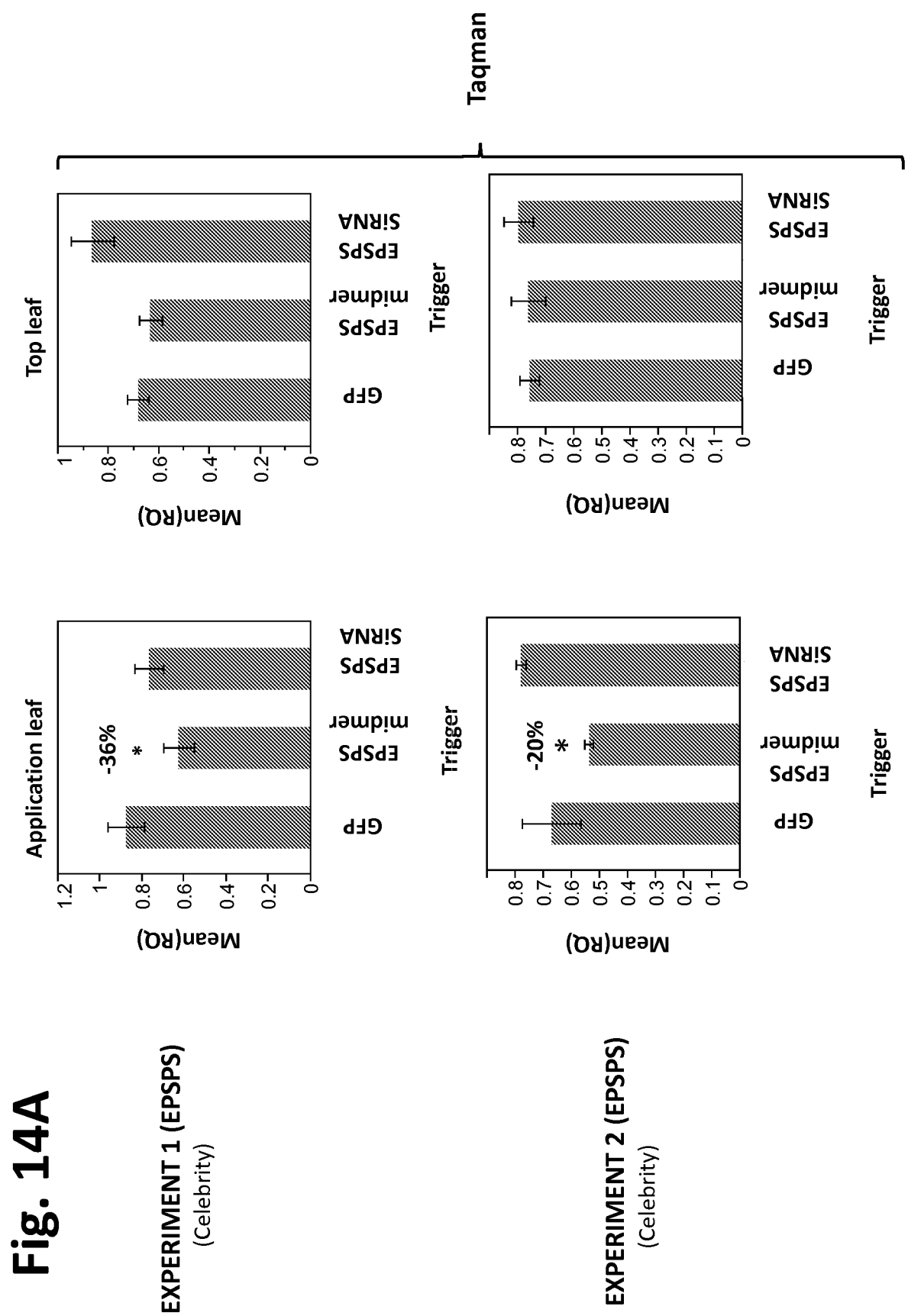
FIGS. 14A and 14B: dsRNA knockdown in adjacent leaflets in tomato. The levels of GFP (control) or EPSPS were determined in both application leaf or top leaf (FIG. 14A) for two separate experiments (1 and 2) in Tomato (cv. Celebrity) transfected with EPSPS midmer (SEQ ID NO:18/SEQ ID NO:19) or EPSPS siRNA (SEQ ID NO:9/SEQ ID NO:10). This analysis revealed a significant decrease in EPSPS RNA levels in both experiments ranging from 20-36% in the application leaf only. In a third experiment, Quantigene® analysis was performed comparing expression levels of EPSPS relative to GFP in application or top leaves transfected with either GFP midmer triggers or GFP siRNA trigger in both application leaf or top leaf. Levels of GFP midmer were decrease by 25% in both application and top leaf (FIG. 14B).
Figure 14B:
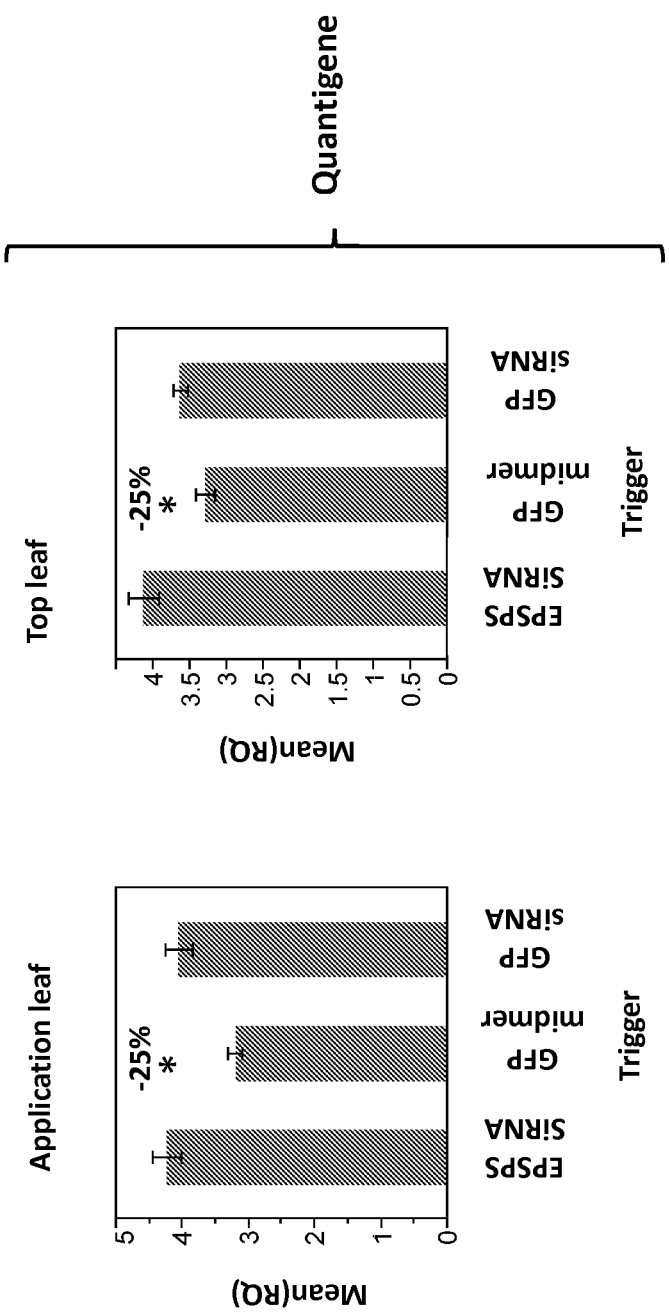

Seeds and plants were prepared as described in Example 5. RNA extraction and analysis were performed as described in Example 5. GFP expression value was measured by Quantigene®. As shown in FIG. 12 and FIG. 13, GFP knockdown was observed in both application leaves and top leaves. As shown in FIG. 14, Hexamethrine bromide plus dsRNA (48-mer) promotes specific EPSPS and GFP mRNA knockdown in adjacent leaflets of in vitro tomato.

Example 7: Glycerol-Polybrene® Mediated Delivery of dsRNA to BY-2 Suspension Cells BY-2_GFP suspension cells constitutively expressing GFP were pelleted from a 150 µL culture and washed once in fresh growth medium (MS). The cells were then resuspended in one of the following Polybrene® formulations in the presence of 10 lag of M411 (non-specific) or GFP22-3 (22mer dsRNA targeting GFP) dsRNA: 400 mM sucrose, 4 mM MES, pH5.7 (SM400); 200 mM glycerol 4 mM MES, pH5.7 (GM200); 400 mL glycerol, 4 mM MES, pH5.7 (GM400); 800 mM glycerol 4 mM MES, pH5.7 (GM800); 1200 mM glycerol 4 mM MES, pH5.7 (GM1200); 1600 mM glycerol 4 mM MES, pH5.7 (GM1600); 2000 mM glycerol 4 mM MES, pH5.7 (GM2000); 2400 mM glycerol 4 mM MES, pH5.7 (GM2400); or 3000 mM glycerol 4 mM MES, pH5.7 (GM3000) (see Table 8). Two replicates of each formulation were tested. Cells were washed with 1 mL W5 buffer and resuspended in 500 mL W1 buffer and incubated overnight.

Figure 15:
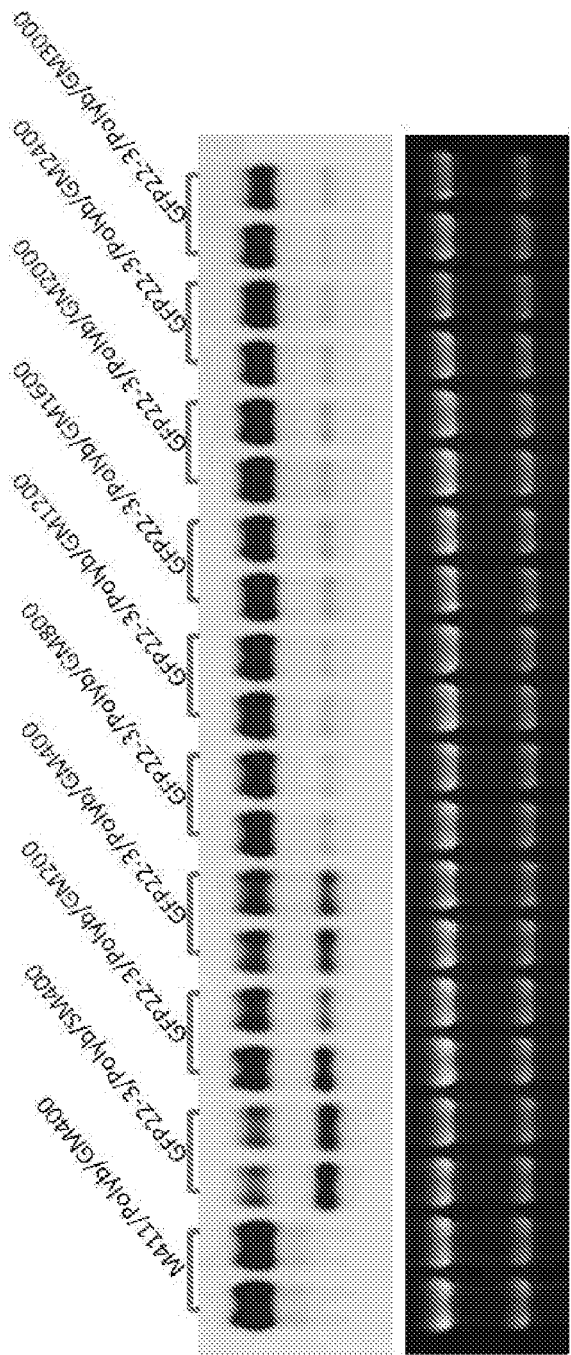
FIG. 15: Northern blot of RNA samples extracted after application of dsRNA with Polybrene®-glycerol into BY_2 suspension cells. The top panel shows the GFP RNA banding pattern with the upper band representing the full length GFP transcript and the lower band presenting the sliced product. The sliced product is present predominantly in GFP22-3/Polyb/SM400, GM200 and GM400 lanes. The lower panel shows the gel for the 18S rRNA internal control stained with ethidium bromide. M411(SEQ ID NO:3/SEQ ID NO:4) was used as control.

The treated BY-2 GFP suspension cells were collected and total RNA was extracted for analysis. A Northern blot was performed using 7 µg of total RNA to detect the presence of GFP mRNA (FIG. 15, top panel, top band) and sliced fragments (FIG. 15, top panel, bottom band) in the treated BY-2_GFP cells. As shown in FIG. 15, all tested formulations were efficacious in delivering dsRNA into the BY-2_GFP suspension cells as evidenced by detection of the sliced fragments. The highest levels of sliced fragments were detected in sucrose-based formulations and formulations with 200 mM and 400 mM glycerol.

TABLE 8

Experimental samples for transfection of dsRNA with Polybrene ®-glycerol into intact BY-2 cells

| Index | Description | Cells | trig/rep | Rep | Form vol/rep | Trigg ug | ul | nmole | Polyb ug | ul | total Gly stock (5M) | H2O/Buffer |
|---|---|---|---|---|---|---|---|---|---|---|---|---|
| 1 | M411/Polyb/GM400 | 150 ul/rep | 10 ug | 2 | 50 | 20 | 3 | 1.34 | 60 | 1.50 | 8 | 88 |
| 2 | GFP22-3/Polyb/SM400 | | | 2 | 50 | 20 | 3 | 1.34 | 60 | 1.50 | | 100 (SM400) |
| 3 | GFP22-3/Polyb/GM200 | | | 2 | 50 | 20 | 3 | 1.34 | 60 | 1.50 | 4 | 92 |
| 4 | GFP22-3/Polyb/GM400 | | | 2 | 50 | 20 | 3 | 1.34 | 60 | 1.50 | 8 | 88 |
| 5 | GFP22-3/Polyb/GM800 | | | 2 | 50 | 20 | 3 | 1.34 | 60 | 1.50 | 16 | 80 |
| 6 | GFP22-3/Polyb/GM1200 | | | 2 | 50 | 20 | 3 | 1.34 | 60 | 1.50 | 24 | 72 |
| 7 | GFP22-3/Polyb/GM1600 | | | 2 | 50 | 20 | 3 | 1.34 | 60 | 1.50 | 32 | 64 |
| 8 | GFP22-3/Polyb/GM2000 | | | 2 | 50 | 20 | 3 | 1.34 | 60 | 1.50 | 40 | 56 |
| 9 | GFP22-3/Polyb/GM2400 | | | 2 | 50 | 20 | 3 | 1.34 | 60 | 1.50 | 48 | 48 |
| 10 | GFP22-3/Polyb/GM3000 | | | 2 | 50 | 20 | 3 | 1.34 | 60 | 1.50 | 60 | 36 |

Example 8: Delivery of dsRNA in BY-2 Suspension Cell Using Transfection Reagents Transfection reagents listed in Table 9 were tested for their efficacy in delivering dsRNA into BY-2 suspension cells.

BY-2_GFP suspension cells constitutively expressing GFP were pelleted from a 150 µL culture and washed once in fresh growth medium (MS). Transfection agent formulations as detailed in Table 9 were added to the cell pellet and incubation was continued at room temperature for 1 hr. Cells were subsequently washed with 1 mL W5 buffer and resuspended in 500 mL W1 buffer overnight. The following day cells were collected for RNA extraction and analysis.

Figure 16:
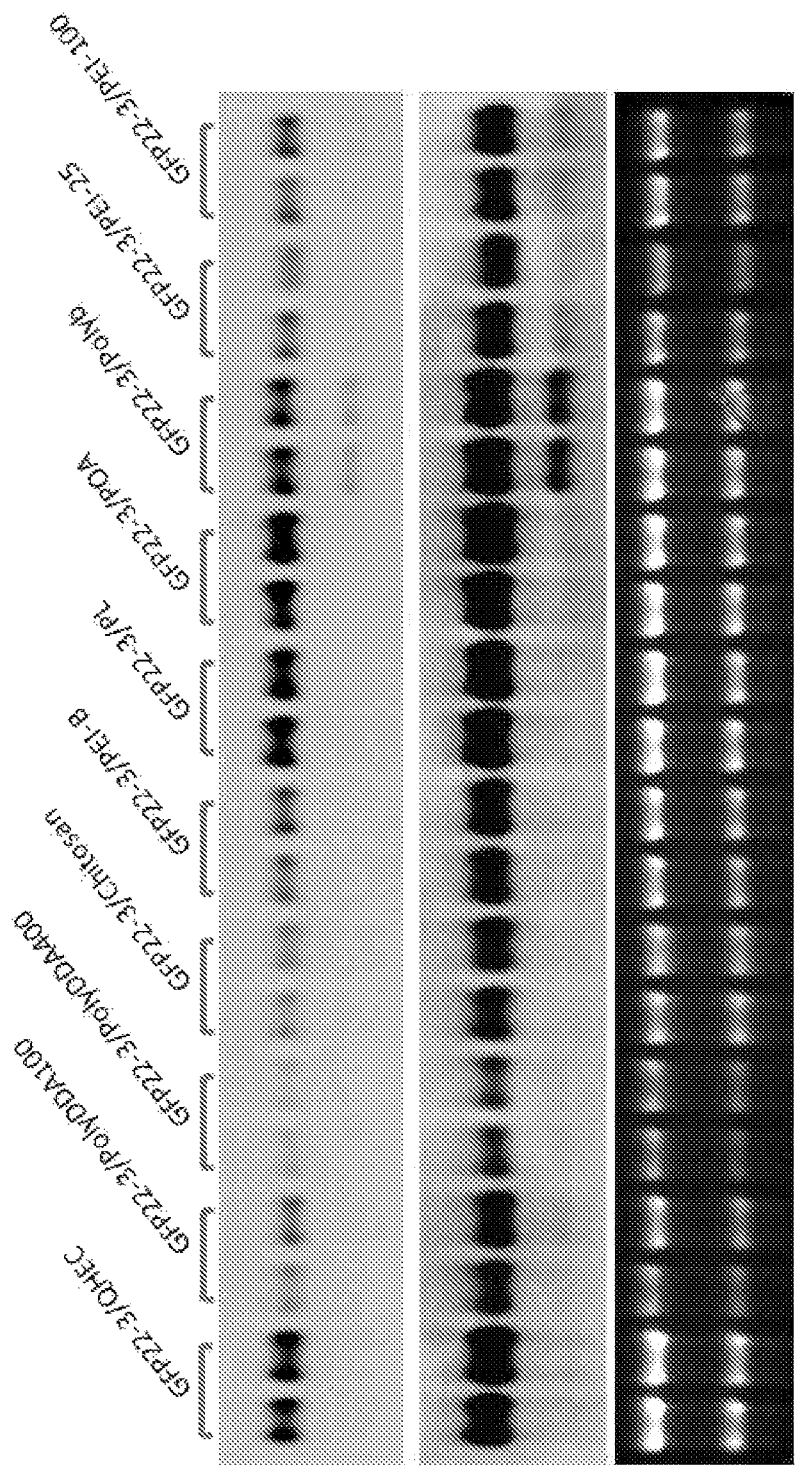
FIG. 16: Northern blot of RNA samples extracted after application of dsRNA into BY-2 cells using different delivery formulations. The top panel shows the GFP RNA banding pattern with sliced products visible in the cells treated with Polybrene® (GFP22-3/Polyb). The middle panel is a longer exposure of the same blot. The lower panel shows the ethidium bromide stained gel for the 18S rRNA internal control.

7 µg of total RNA was used for RNA Northern blots, to detect the presence of GFP mRNA and sliced product in the BY-2 GFP suspension cells. As shown in the middle panel of FIG. 16 (long exposure), weak bands corresponding to sliced fragments were observed for PolyDDA100 and PolyDDA400 formulations. Similar levels of sliced fragments were observed for the PEI-25 and PEI-100 formulations (FIG. 16). No bands corresponding to sliced fragments were observed in samples treated with formulations made with PEI-B, PL, POA and QHEC.

TABLE 9

Transfection agents used in formulation for delivery of dsRNA into BY-2 cells

| Index | Transfection Agents | Agent 1:1 | 2:1 | 3:1 | Trigger | Agt conc. | Rep | Cells/rep | Trig/rep | Trig. (ul) | Agt (ul) | SM400 | Vol/rep |
|---|---|---|---|---|---|---|---|---|---|---|---|---|---|
| 1 | QHEC | | 6 | 3 | 10 | 2 | 150 | 10 | 2.67 | 4 | 103.33 | 50 | |
| 2 | PolyDDA100 | | 6 | 3 | 10 | 2 | 150 | 10 | 2.67 | 4 | 103.33 | 50 | |
| 3 | PolyDDA400 | | 6 | 3 | 10 | 2 | 150 | 10 | 2.67 | 4 | 103.33 | 50 | |

TABLE 9-continued

Transfection agents used in formulation for delivery of dsRNA into BY-2 cells

| | | Agent | | | | | | | | | | |
|---|---|---|---|---|---|---|---|---|---|---|---|---|
| Index | Transfection Agents | 1:1 | 2:1 | 3:1 | Trigger | Agt conc. | Rep | Cells/rep | Trig/rep | Trig. (ul) | Agt (ul) | SM400 | Vol/rep |
| 4 | Chitosan | | 6 | | 3 | 2 | 2 | 150 | 10 | 2.67 | 20 | 87.33 | 50 |
| 5 | PEI-B | 3 | | | 3 | 5 | 2 | 150 | 10 | 2.67 | 4 | 103.33 | 50 |
| 6 | PolyLysin | 3 | | | 3 | 5 | 2 | 150 | 10 | 2.67 | 4 | 103.33 | 50 |
| 7 | POA | 3 | | | 3 | 5 | 2 | 150 | 10 | 2.67 | 4 | 103.33 | 50 |
| 8 | PolyB | | | 9 | 3 | 10 | 2 | 150 | 10 | 2.67 | 6 | 101.33 | 50 |
| 9 | PEI-25 | 3 | | | 3 | 5 | 2 | 150 | 10 | 2.67 | 4 | 103.33 | 50 |
| 10 | PEI-100 | 3 | | | 3 | 5 | 2 | 150 | 10 | 2.67 | 4 | 103.33 | 50 |

1. Hydroxyethylcellulose ethoxylate, quaternized (QHEC)
2. Poly(diallyldimethylammonium chloride) solution, MW 100K-200K, 20% (200 ug/ul) (PolyDDA100)
3. Poly(diallyldimethylammonium chloride) solution, MW 500K-600K, 20% (200 ug/ul) (PolyDDA400)
4. PEI-B: branched polyethyleneimine
5. POA: polyarginine
6. PolyB: Polybrene
7. PEI-25: linear polyethylenimine 25 kDa
8. PEI-100: linear polyethylenimine 100 kDa

Example 9: Endoporter Delivery of dsRNA into BY-2 Suspension Cells

Formulations of Endoporter or Endoporter and Polybrene● listed in Table 10 were tested for their efficacy in delivering dsRNA into BY-2 suspension cells.

BY-2 GFP suspension cells constitutively expressing GFP were pelleted from a 150 μL culture and washed once in fresh growth medium (MS). Formulations as detailed in Table 10 were added to the cell pellet and incubation was continued at room temperature for 1 hr. Cells were subsequently washed with 1 mL W5 buffer and resuspended in 500 mL W1 buffer overnight. The following day cells were collected for RNA extraction and Northern blot analysis.

The underside (bottom) of *Nicotiana benthamiana* leaves (2 leaves/treated plant) were pre-treated with 0.2% Silwet L-77 in H$_2$O. The leaves were allowed to dry, then m411 (non-specific) or 16cGFP22-3 (GFP-specific) dsRNA was applied in a formulation of Polyb/SM400 with 0.01% Silwet L-77 as described in Table 11, Index 1 and 2, respectively.

The upper side (top) of *Nicotiana benthamiana* leaves (2 leaves/treated plant) were pre-treated with 0.2% Silwet L-77 in H$_2$O. The leaves were allowed to dry, then 16cGFP22-3 (GFP-specific) dsRNA was applied in a formulation of Polyb/SM400 with 0.01% Silwet L-77 as described in Table 11, Index 3.

*Nicotiana benthamiana* leaves (2 leaves/treated plant) were infiltrated from the underside with 16cGFP22-3 (GFP-

TABLE 10

Combinations of Endoporter, dsRNA and Polybrene ®/sucrose

| | | | | | Trigg | | Polyb | | total Endoporter | |
|---|---|---|---|---|---|---|---|---|---|---|
| Index | Description | Cells | trig/rep | Rep | ug | ul | ug | ul | (1 mM) | Buffer |
| 1 | M411/Polyb/SM400 | 500 ul/rep | 30 ug | 2 | 60 | 8 | 180 | 18 | 0 | 274 |
| 2 | M411/5xEndoporter (38 uM) | | | 2 | 60 | 8 | 0 | 0 | 11 | 281 |
| 3 | M411/Polyb/5xEndoporter (38 uM) | | | 2 | 60 | 8 | 180 | 18 | 11 | 263 |
| 4 | GFP22-3/Polyb/SM400 | | | 2 | 60 | 8 | 180 | 18 | 0 | 274 |
| 5 | GFP22-3/5xEndoporter (38 uM)/SM400 | | | 2 | 60 | 8 | 0 | 0 | 11 | 281 |
| 6 | GFP22-3/3xEndoporter (22 uM)/SM400 | | | 2 | 60 | 8 | 0 | 0 | 7 | 285 |
| 7 | GFP22-3/1xEndoporter (7.5 uM)/SM400 | | | 2 | 60 | 8 | 0 | 0 | 2 | 290 |
| 8 | GFP22-3/Polyb/5xEndoporter (38 uM)/SM400 | | | 2 | 60 | 8 | 180 | 18 | 11 | 263 |
| 9 | GFP22-3/Polyb/3xEndoporter (22 uM)/SM400 | | | 2 | 60 | 8 | 180 | 18 | 7 | 267 |
| 10 | GFP22-3/Polyb/1xEndoporter (7.5 uM)/SM400 | | | 2 | 60 | 8 | 180 | 18 | 2 | 272 |

Figure 17:
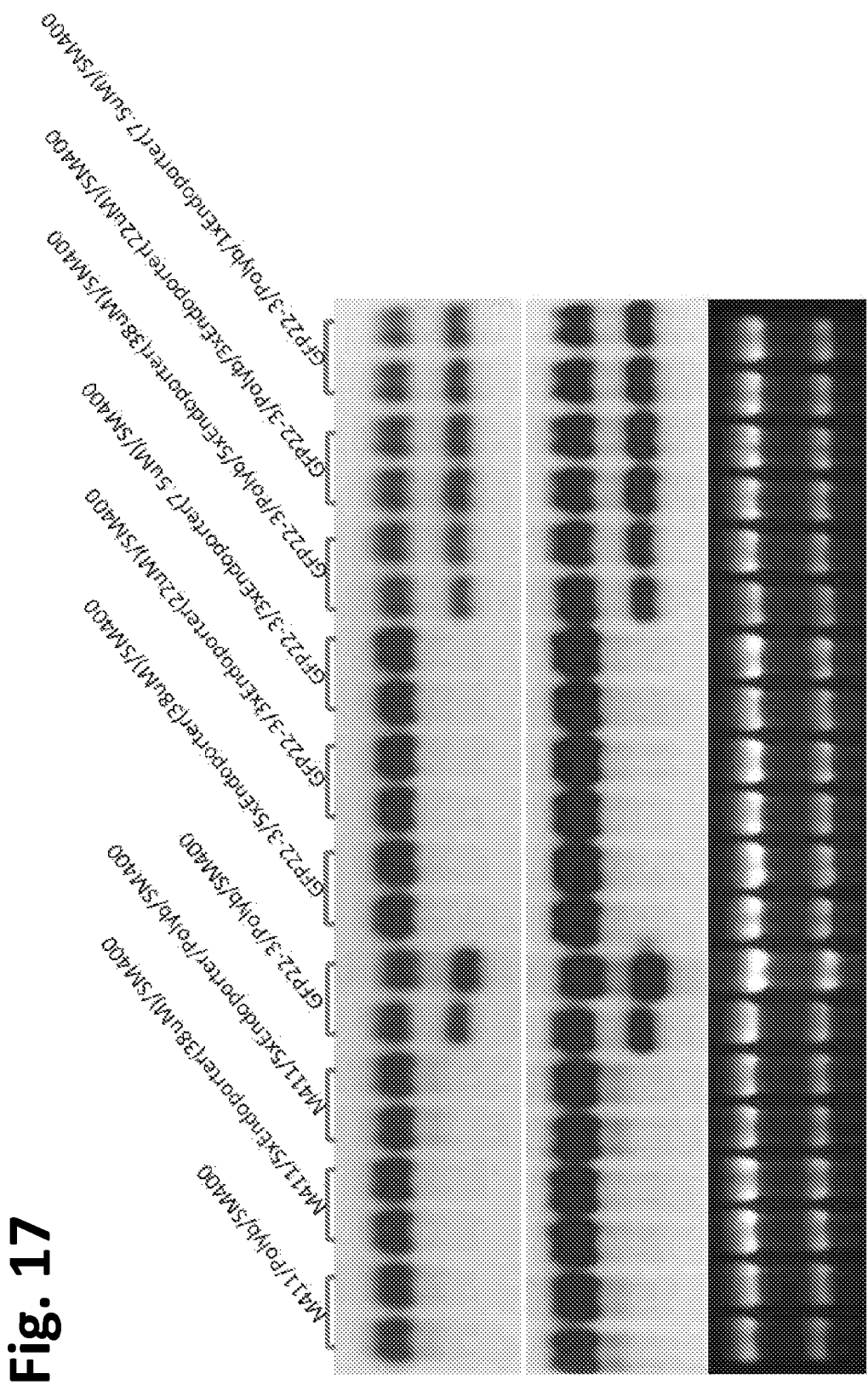
FIG. 17: Northern blot of RNA samples extracted after application of dsRNA into BY-2 cells using different combinations of Endoporter with Polybrene®. The top panel shows the GFP RNA banding pattern with the sliced products present in the GFP22-3/Polyb/SM400 lanes as well as in the lanes containing different amounts of Endoporter added to the Polyb/SM400 formulation. The middle panel is a darker exposure of the same Northern blot. The lower panel shows the ethidium bromide stained gel for the 18S rRNA internal control.

As shown in FIG. 17, sliced fragments were not observed in cells treated with formulations of dsRNA/Endoporter/SM400, while dsRNA/Polyb/Endoporter/S M400 treated cells generated sliced fragments and a visible knock down of GFP RNA levels in treated samples.

Example 10: dsRNA Delivery into Plant Leaf Cells Through Topical Application of a Sucrose/Polyb/Silwet L-77 Based Formulation Delivery of dsRNA by topical treatment of *Nicotiana benthamiana* leaves with sucrose/Polyb/Silwet based formulations was assessed.

specific) dsRNA in a formulation of Polyb/SM400 as described in Table 11, Index 4.

Figure 18:
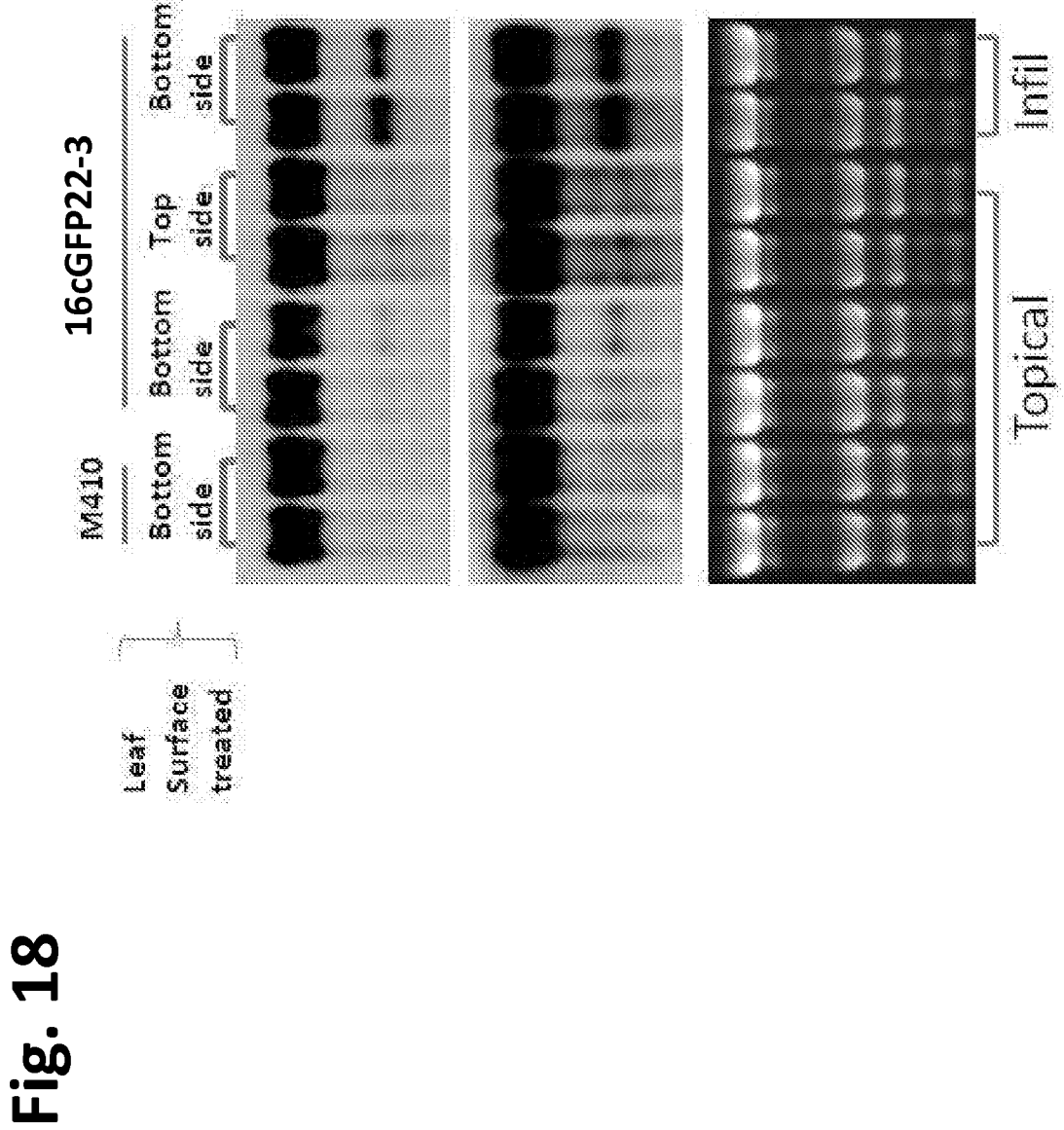
FIG. 18: Northern blot of RNA samples extracted from N. benthamiana leaves after delivery of dsRNA. The top panel shows the GFP RNA in control tissue (M410; SEQ ID NO:3/SEQ ID NO:4) and for the three separate applications with dsRNA. The top panel shows that a sliced fragment is present in the dsRNA treated leaves when the delivery was performed from the underside of the leaf (16cGFP22-3/bottom side). A less discrete, more fragmented banding pattern is visible in the treatment applied from the top side. A strong slicing pattern is visible in the treatment when dsRNA was infiltrated from the bottom side (right most lanes in the blot). The middle panel shows a darker exposure of the Northern blot. The lower panel shows the ethidium bromide stained gel for the 18S rRNA internal control.

At the completion of the experiment, plant leaf disks were collected from the treatment spots for RNA extraction and Northern Blot analysis. Sliced fragments were identified where 16cGFP22-3 (GFP-specific) dsRNA formulations were topically applied to the bottom side of leaves. See FIG. 18, lanes 3 and 4. Conversely, sliced fragments were not observed where 16cGFP22-3 (GFP-specific) dsRNA formulations were topically applied to the upper side of the leaves. See FIG. 18, lanes 5 and 6. Infiltrated 16cGFP22-3 (GFP-specific) dsRNA formulations demonstrated strong sliced fragments. See FIG. 18, lanes 7 and 8.

TABLE 11

Test samples for application on *N. benthamiana*

| Index | Description | Reps (plant) | Trig/ plant | Form vol/ plant (1 leaf/plant) | Trig (ul) | Polyb (40 ug/ul) (5:1) | SM800 | 1% silwet | H2O |
|---|---|---|---|---|---|---|---|---|---|
| 1 | M411/polyb/SM400_Silwet_0.20_0.01%_Bottom | 2 | 25 | 50 | 6.7 | 6.3 | 45.0 | 1.0 | 41.1 |
| 2 | 16cGFP22-3/polyb/SM400_Silwet_0.2%_0.01%_Bottom | 2 | 25 | 50 | 6.7 | 6.3 | 45.0 | 1.0 | 41.1 |
| 3 | 16cGFP22-3/polyb/SM400_Silwet_0.2%_0.01%_Top | 2 | 25 | 50 | 6.7 | 6.3 | 45.0 | 1.0 | 41.1 |
| 4 | 16cGFP22-3/polyb/SM400_infil | 2 | 25 | 50 | 6.7 | 6.3 | 45.0 | | 42.1 |

Example 11: Modification and Optimization of BY-2 Assay with Polybrene® Based dsRNA Formulation In this example, BY-2 cells were treated using standard assay conditions with dsRNA/Polyb/SM400 formulation for one hour followed by two washes and incubation in buffer for 24 hr. To simplify and optimize the BY-2 transfection assay, we tested the dsRNA/Polyb/SM400 formulation and the MS growth medium based formulations with "one-step" 5 hr cell treatment without washing and incubation steps as outlines in Table 12. Cells were pelleted from a 150 μl culture and washed once with MS medium, formulations were added to the cell pellet and incubation was continued for an additional 5 hr. At the completion of the incubation period cells were collected for RNA extraction and analysis.

TABLE 12

Test samples for application in BY-2 suspension cell culture

| Index | Description | Reps | Trig/ rep | Form vol/rep | Trig 7.49 (ug/ul)(ul) | Polyb (10 ug/ul) (3:1) | SM400 | SM200 | MS | Suc (2.6M) |
|---|---|---|---|---|---|---|---|---|---|---|
| 1 | M410/polyb/SM400_5 hr | 2 | 10 | 50 | 2.7 | 6.0 | 91.3 | | | |
| 2 | GFP22-3/polyb/SM400_5 hr | 2 | 10 | 50 | 2.7 | 6.0 | 91.3 | | | |
| 3 | GFP22-3/polyb/SM200_5 hr | 2 | 10 | 50 | 2.7 | 6.0 | | 91.3 | | |
| 4 | M410/polyb/MS + S300_5 hr | 2 | 10 | 50 | 2.7 | 6.0 | | | 79.79 | 11.54 |
| 5 | GFP22-3/polyb/MS_5 hr | 2 | 10 | 50 | 2.7 | 6.0 | | | 91.33 | |
| 6 | GFP22-3/polyb/MS + S100_5 hr | 2 | 10 | 50 | 2.7 | 6.0 | | | 87.48 | 3.85 |
| 7 | GFP22-3/polyb/MS + S200_5 hr | 2 | 10 | 50 | 2.7 | 6.0 | | | 83.64 | 7.69 |
| 8 | GFP22-3/polyb/MS + S300_5 hr | 2 | 10 | 50 | 2.7 | 6.0 | | | 79.79 | 11.54 |

Note:
GFP22-3 (SEQ ID NO: 1/SEQ ID NO: 2): 22 mer dsRNA targeting GFP
M410 (SEQ ID NO: 3/SEQ ID NO: 4): 24 mer dsRNA targeting EPSPS, used as nonspecific control
MS: cell growth medium
SM400: 400 mM sucrose, 4 mM MES, pH 5.7
SM200: 200 mM sucrose, 4 mM MES, pH 5.7

Figure 19:
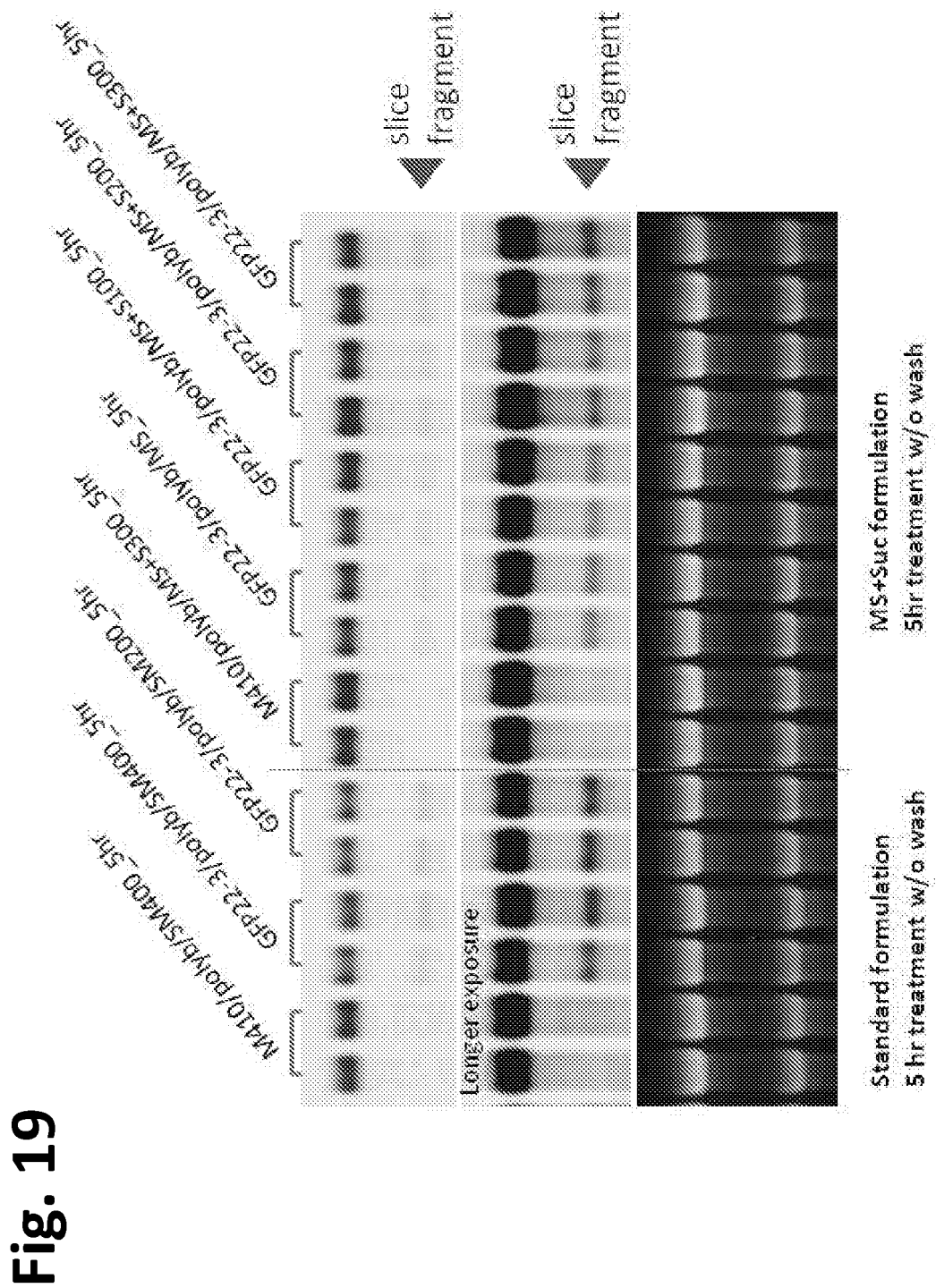
FIG. 19: Northern blot analysis on extracts from transfected BY_2 cells treated with GFP22-3 dsRNA (SEQ ID NO:3/SEQ ID NO:4) or control dsRNA (M410, SEQ ID NO:3/SEQ ID NO:4) in a modified protocol without washing and incubation steps. Argonaute (AGO) cleavage products are clearly visible for all tested GFP22-3 (SEQ ID NO:3/SEQ ID NO:4) transfected dsRNAs.

The results of this experiment are shown in FIG. 19. A sliced fragment was detectable in samples treated with standard trigger/Polyb/SM buffer for 5 hr without washing steps. Additionally, a sliced fragment was observed in samples treated with MS based formulations.

Example 12: Optimization of Polybrene® Based Trigger Formulation for Plant Assay The standard Polybrene® based formulation contains 400 mM sucrose which may cause plant leaf tissue damage when large volume of the formulation is applied to plant leaves. To optimize the formulation for reduced plant tissue damage, formulations were tested with reduced sucrose concentration and with different dsRNA:Polybrene® ratios. The modified formulations were tested in *Nicotiana benthamiana* 16c plant with leaf infiltration. One leaf of each juvenile plant was infiltrated with 501,11 of formulation as outlined in Table 13 below on 2-3 spots. Approximately 5 hr after the infiltration the infiltrated spots were collected and processed for RNA extraction and analysis.

TABLE 13

Test samples for application on *N. benthamiana* 16c leaves

| Index | Description | Reps (spots) | Trig/ plant | Form vol/plant (1 leaf/plant) | Trig (ul) | Polyb (10 ug/ul) | SM400 | SM200 | SM100 |
|---|---|---|---|---|---|---|---|---|---|
| 1 | M411/polyb/SM100 (1:5) | 3 | 25 | 50 | 10.0 | 37.5 | | | 102.5 |
| 2 | 16cGFP22-3/polyb/SM400 (1:5) | 3 | 25 | 50 | 10.0 | 37.5 | 102.5 | | |
| 3 | 16cGFP22-3/polyb/SM400 (1:3) | 3 | 25 | 50 | 10.0 | 22.5 | 117.5 | | |

TABLE 13-continued

Test samples for application on N. benthamiana 16c leaves

| Index | Description | Reps (spots) | Trig/ plant | Form vol/plant (1 leaf/plant) | Trig (ul) | Polyb (10 ug/ul) | SM400 | SM200 | SM100 |
|---|---|---|---|---|---|---|---|---|---|
| 4 | 16cGFP22-3/polyb/SM200 (1:5) | 3 | 25 | 50 | 10.0 | 37.5 | | 102.5 | |
| 5 | 16cGFP22-3/polyb/SM200 (1:3) | 3 | 25 | 50 | 10.0 | 22.5 | | 117.5 | |
| 6 | 16cGFP22-3/polyb/SM100 (1:5) | 3 | 25 | 50 | 10.0 | 37.5 | | | 102.5 |
| 7 | 16cGFP22-3/polyb/SM100 (1:3) | 3 | 25 | 50 | 10.0 | 22.5 | | | 117.5 |

Note:
16cGFP22-3 (SEQ ID NO: 5/SEQ ID NO: 6): 22 mer dsRNA targeting GFP
M410(SEQ ID NO: 3/SEQ ID NO: 4): 24 mer dsRNA targeting EPSPS, used as nonspecific control
SM400: 400 mM sucrose, 4 mM MES, pH 5.7
SM200: 200 mM sucrose, 4 mM MES, pH 5.7
SM100: 100 mM sucrose, 4 mM MES, pH 5.7

Figure 20:
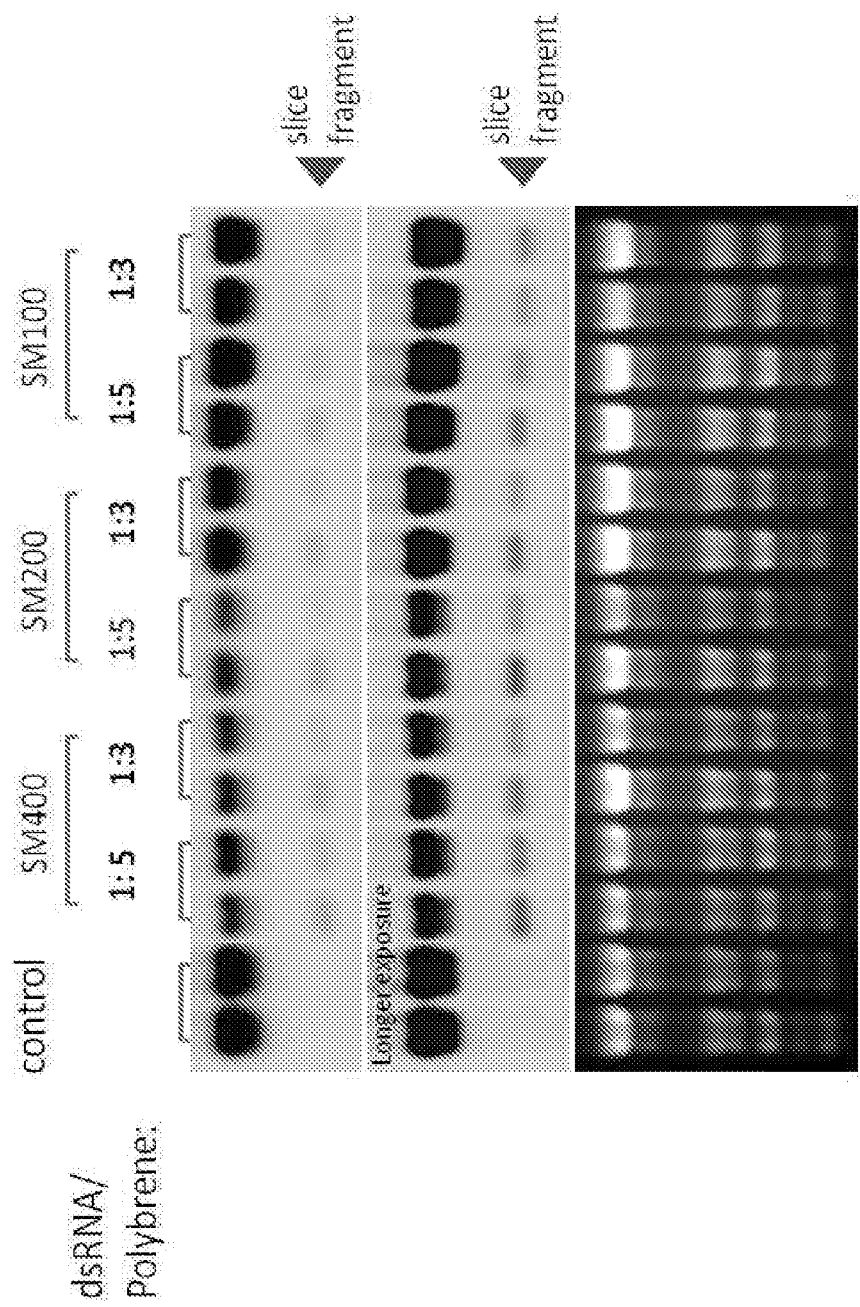
FIG. 20: Northern blot analysis of N. benthamiana infiltrated leaves using varying amounts of sucrose and different dsRNA:Polybrene® ratios. A sliced fragment was observed in all treated samples, however, significant reduction of target message was only seen in the samples treated with the standard SM400 formulation (400 mM sucrose) and the 1:5 or 1:3 dsRNA:Polybrene® ratio. A 1:5 ratio of dsRNA:Polybrene® and 200 mM sucrose (SM200) showed significant target knockdown as well.

The results are shown in FIG. 20. Sliced fragments observed in all the samples treated with different formulations. However, significant target knockdown was only observed in samples treated with SM400 with both 1:5 and 1:3 dsRNA:Polybrene® ratio and in samples treated with SM200 with 1:5 dsRNA:Polybrene® ratio. SM400 formulation treated leaves experienced some tissue damage (data not shown) while no significant tissue damage was observed on leaves treated with SM200 and SM100 formulations.

Example 13: Identification of New Efficacious Transfection Agents for the BY-2 Suspension Cell Assay A list of polymers and polypeptides were tested using the BY-2 assay conditions. A few positive agents were tested together in one assay and the assay conditions and the results are described in this example. In addition to Polybrene® (PB) the other agents tested consisted of a partial peptide of the coat protein of Cowpea Chlorotic Mottle Virus (CCMV, sequence: KLTRAQRRAAARKNKRNTR, SEQ ID NO:27), a partial peptide of the coat protein of Brome Mosaic Virus (BMV, sequence: KMTRAQRRAAARRNRWTAR, SEQ ID NO:28) and a commercially available polylysine (PLL1 1-5K) preparation. Formulations were tested as outlined in Table 14. Cells were pelleted from a 150 µl medium (MS). Formulation was added to the cell pellet and allowed to incubate at room temperature for 1 hr. Cells were washed twice with 1 ml W5 buffer and resuspended in 500 µl W1 buffer overnight. Cells were collected for RNA extraction and analysis.

TABLE 14

Test samples for application in BY-2 suspension cells.

| Index | Description | Reps | Trig/ rep | Form vol/ rep | Trig (ul) | Agents (10 mg/ml) | SM400 |
|---|---|---|---|---|---|---|---|
| 1 | M411/PB (3x)/SM400 | 3 | 10 | 50 | 4.0 | 9.0 | 137.0 |
| 2 | GFP22-3/PB (3x)/SM400 | 3 | 10 | 50 | 4.0 | 9.0 | 137.0 |
| 3 | GFP22-3/CCMV (5x)/SM400 | 3 | 10 | 50 | 4.0 | 15.0 | 131.0 |
| 4 | GFP22-3/BMV (5x)/SM400 | 3 | 10 | 50 | 4.0 | 15.0 | 131.0 |
| 5 | GFP22-3/PLL1 (5x)/SM400 | 3 | 10 | 50 | 4.0 | 15.0 | 131.0 |
| 6 | GFP22-3/BMV (3x)/SM400 | 3 | 10 | 50 | 4.0 | 9.0 | 137.0 |

The results are shown in FIG. 21. SliceD fragment and a slight decrease in target levels indicating a small knockdown were observed in samples treated with formulations containing Polybrene®, CCMV, BMV, or PLL (1-5k). The transfection activity of BMV and CCMV appeared to be close to that for Polybrene®. No significant cytotoxicity observed from samples treated with CCMV, BMV, and PPL(1-5k) as evidenced by GFP fluorescence (data not shown) and RNA quality.

Example 14: BY2 Cells Transfection Using Lipofectamine® 3000

The efficacy of Lipofectamine® 3000 (L3K) transfection reagent was evaluated in the BY2 system. GFP22.3 (SEQ ID NO: 1/SEQ ID NO:2) or Control (SEQ ID NO: 22/SEQ ID NO:23; off target control) was formulated with L3k in 400 mM sucrose and 4 mM MES pH 5.7 (SM400). The siRNA was diluted to the target concentration in SM400. P3000 was added to the diluted siRNA at a rate of 2 microliters per microgram of siRNA and mixed by vortexing. L3000 was diluted into SM400 at a rate of 0.75 ("Low") or 1.5 ("High") microliters per microgram of siRNA and mixed by vortexing. Equal volumes of the siRNA/P3000 solution and L3000 solution were combined, mixed, and incubated at RT for 5 min. 100 µl of the siRNA/L3K complexes were added to washed BY2 cells and incubated for 1-2 hrs. The cells were then washed with W5 buffer and incubated overnight in WI buffer. GFP expression was evaluated using Northern blot 18 hours after treatment.

A clear sliced fragment was observed using L3K in initial experiments (FIG. 22). Both GFP knockdown and a sliced fragment were observed in follow-up experiments (FIG. 23). In some experiments, L3k was more efficient than Polybrene® alone, but in other experiments the GFP knockdown efficiency is not enhanced relative to Polybrene® using L3K (FIG. 24).

Example 15: Effect of Wortmanin & Brefeldin A on Polybrene®/Sucrose Transfection The endomembrane trafficking inhibitors wortmanin and brefeldin A were used to investigate the role of endocytosis in sliced fragment formation and gene repression after Polybrene®/sucrose delivery of siRNA. BY2 cells were pretreated for 2 h with DMSO, wortmanin, or brefeldin A. GFP22.3 (SEQ ID NO: 1/SEQ ID NO:2) or Control (SEQ ID NO:22/SEQ ID NO:23) was complexed with Polybrene® at a 3:1 (m/m) ratio in SM400, and BY2 cells were transfected using the standard Polybrene®/sucrose procedure. In the second experiment, DMSO, wortmanin, or brefeldin A was added to the WI buffer during the overnight incubation. Gene repression and sliced fragment formation were measured at 18 h after treatment.

The results show that both gene repression and sliced fragment formation were insensitive to wortmanin and brefeldin A (FIG. 25).

Example 16: Effect of Polybrene® on dsRNA Stability in *N. benthamiana* Leaves

The effect of Polybrene® on the stability of dsRNA triggers after leaf infiltration was studied in *N. benthamiana*. Control (EPSPS5.3; SEQ ID NO:3/SEQ ID NO:4) was diluted into water and complexed with Polybrene® at a 3:1 (m/m) ratio. Approximately 50 µl of dsRNA was infiltrated into a single *benthamiana* leaf. Infiltrated leaves were harvested at 0-48 h after infiltration, washed extensively, and leaf punches were collected from the infiltrated area. Total RNA was extracted using Trizol, and trigger integrity was measured using anion exchange-HPLC or Northern blotting. Similar to previous experiments, uncomplexed dsRNA was rapidly degraded. The half-life of Polybrene® complexed 24 bp dsRNA trigger was approximately 20 hr (FIG. 26). Using longer RNAs (48 bp, GFP48, SEQ ID NO:25) the nature of the nuclease could be discerned. Similar to the BY2 system, dsRNA trigger degradation in *N. benthamiana* appears to proceed primarily via an exo-nuclease. The half-life of the 48mer complexed with Polybrene® was similar, at 16 hr, to estimates generated using the 22mer. RNAiMax formulated according to the product insert appeared to provide more protection than Polybrene®, but as with Polybrene®, degradation was only slowed, not prevented (FIG. 27).

What is claimed is:

1. A method for delivering one or more polynucleotides into a plant cell, comprising applying onto the intact surface of a plant or an intact part thereof a mixture comprising:
   a) a cationic polyelectrolyte;
   b) an osmolyte; and
   c) the one or more polynucleotides,
   wherein the cationic polyelectrolyte is hexadimethrine bromide,
   wherein the osmolyte comprises a carbohydrate or a sugar alcohol, and
   wherein the one or more polynucleotides comprise at least one segment of 18 or more contiguous nucleotides that shares about 90% to about 100% sequence identity to a fragment of a target gene, or the complement thereof.

2. The method of claim 1, wherein the polynucleotide suppresses expression of the target gene.

3. The method of claim 1, wherein the polyelectrolyte and the one or more polynucleotides form a complex.

4. The method of claim 1, wherein the carbohydrate is selected from the group consisting of glyceraldehyde, dihydroxyacetone, ribose, ribulose, glucose, fructose, galactose, and sucrose, and wherein the sugar alcohol is selected from the group consisting of ethylene glycol, glycerol, erythritol, threitol, arabitol, xylitol, ribitol, galactitol, fucitol, iditol, inositol, sorbitol, and mannitol.

5. The method of claim 1, wherein the polynucleotide is a single stranded DNA, a double-stranded DNA, a single-stranded RNA, a double-stranded RNA, or a DNA/RNA hybrid.

6. The method of claim 1, wherein the target gene is an endogenous gene.

7. The method of claim 1, wherein the target gene is
   (a) an essential gene for maintaining the growth or life of the plant;
   (b) a gene encoding a protein that provides herbicide resistance to the plant, or
   (c) a gene that transcribes to an RNA regulatory agent.

8. The method of claim 1, wherein the target gene is an endogenous gene of an invertebrate plant pest or a pathogen of the plant.

9. The method of claim 1, wherein the plant is a weed or a volunteer plant.

10. The method of claim 1, wherein the mixture further comprises a surfactant.

11. A method for delivering one or more polynucleotides into a plant cell, comprising applying onto the intact surface of a plant or an intact part thereof a mixture comprising:
   a. a cationic polyelectrolyte;
   b. the one or more polynucleotides, wherein the polynucleotide comprises at least one segment of 18 or more contiguous nucleotides that shares about 90% to about 100% sequence identity to a fragment of a target gene, or the complement thereof, wherein the cationic polyelectrolyte is hexadimethrine bromide.

12. The method of claim 11, wherein the polyelectrolyte and the one or more polynucleotides form a complex.

* * * * *

```
                            SEQUENCE LISTING

<160> NUMBER OF SEQ ID NOS: 51

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ggcucaaggc uaacuucaaa a                                                 21

<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uugaaguuag ccuugaugcc gu                                                22

<210> SEQ ID NO 3
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
augccagaug uugcuaugac ucuu                                              24

<210> SEQ ID NO 4
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
aagagucaua gcaacaucug gcau                                              24

<210> SEQ ID NO 5
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 5
ggcucaaagc caacuucaaa a                                                    21

<210> SEQ ID NO 6
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uugaaguugg cuugaugcc gu                                                    22

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
acgaaaacuu acccuuaaaa a                                                    21

<210> SEQ ID NO 8
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uuuaagggua aguuuccgu au                                                    22

<210> SEQ ID NO 9
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
augaacaaaa ugccagaugu gg                                                   22

<210> SEQ ID NO 10
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uguacuuguu uuacggucua ca                                                   22

<210> SEQ ID NO 11
<211> LENGTH: 48
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 11
gcgugccauu gacgugaaca ugaacaaaau gccagaugug gccaugac          48

<210> SEQ ID NO 12
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
gaagggucag acuacugcau aaucac                                  26

<210> SEQ ID NO 13
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
uucguggguc aucauaugua ucaaucuc                                28

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ccaccagaaa aguuaaacgu a                                       21

<210> SEQ ID NO 15
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
gacgaccccc cuauagauuu cuc                                     23

<210> SEQ ID NO 16
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gcucuuccuc aauucgaaac ca                                      22

<210> SEQ ID NO 17
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 17
uguuucgucu uguuugac                                                    19

<210> SEQ ID NO 18
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
gauguugugc cggaucuuga aguucaccuu gaugccguuc uucugc                     46

<210> SEQ ID NO 19
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gcagaagaac ggcaucaagg ugaacuucaa gauccggcac aacaucga                   48

<210> SEQ ID NO 20
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uugaaguuca ccuugaugcc gu                                               22

<210> SEQ ID NO 21
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ggcaucaagg ugaacuucaa ga                                               22

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
augccagaug uugcuaugac u                                                21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic -continued oligonucleotide

<400> SEQUENCE: 23
ucauagcaac aucuggcauu u                                               21

<210> SEQ ID NO 24
<211> LENGTH: 103
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 24
gagaggccug ugggcauuca gucuggaucg cgaaaacugu ggaauugauc agcguuggug      60
ggaaagcgcg uuacaagaaa gccgggcaau ugcugugcca ggc                      103

<210> SEQ ID NO 25
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gcagaagaac ggcaucaagg cuaacuucaa gaucaggcac aacaucaa                  48

<210> SEQ ID NO 26
<211> LENGTH: 123
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 26
gggacacaag cuggaguaca acuacaacuc ccacaacgua uacaucacgg ccgacaagca      60
gaagaacggc aucaaggcua acuucaagau caggcacaac aucgaagaug aagcgugca     120 acu                                                                  123

<210> SEQ ID NO 27
<211> LENGTH: 19
<212> TYPE: PRT
<213> ORGANISM: Cowpea chlorotic mottle virus

<400> SEQUENCE: 27

Lys Leu Thr Arg Ala Gln Arg Arg Ala Ala Ala Arg Lys Asn Lys Arg
1               5                   10                  15

Asn Thr Arg

<210> SEQ ID NO 28
<211> LENGTH: 19
<212> TYPE: PRT
<213> ORGANISM: Brome mosaic virus

<400> SEQUENCE: 28

Lys Met Thr Arg Ala Gln Arg Arg Ala Ala Ala Arg Arg Asn Arg Trp
1               5                   10                  15

Thr Ala Arg

<210> SEQ ID NO 29

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Gly Arg Lys Lys Arg Arg Gln Arg Arg Arg
1               5                   10

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Thr Arg Gln Ala Arg Arg Asn Arg Arg Arg Trp Arg Glu Arg Gln
1               5                   10                  15

Arg

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Arg Arg Arg Asn Arg Thr Arg Arg Asn Arg Arg Arg Val Arg
1               5                   10                  15

<210> SEQ ID NO 32
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Asp

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Gln Ile Lys Ile Trp Phe Gln Asn Arg Arg Met Lys Trp Lys Lys
1               5                   10                  15

<210> SEQ ID NO 34
<211> LENGTH: 23
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 34

```
Leu Ile Arg Leu Trp Ser His Leu Ile His Ile Trp Phe Gln Asn Arg
1               5                   10                  15
Arg Leu Lys Trp Lys Lys Lys
            20
```

<210> SEQ ID NO 35
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

```
Gly Ala Leu Phe Leu Gly Phe Leu Gly Ala Ala Gly Ser Thr Met Gly
1               5                   10                  15
Ala Trp Ser Gln Pro Lys Lys Lys Arg Lys Val
            20                  25
```

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

```
Phe Phe Leu Ile Pro Lys Gly Arg Arg Arg Arg Arg Arg Arg Arg Arg
1               5                   10                  15
```

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

```
Arg Arg Arg Arg Arg Arg Arg Arg Arg
1               5
```

<210> SEQ ID NO 38
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

```
Gly Leu Phe Glu Ala Ile Glu Gly Phe Ile Glu Asn Gly Trp Glu Gly
1               5                   10                  15
Met Ile Asp Gly Trp Tyr Gly Arg Arg Arg Arg Arg Arg Arg Arg Arg
            20                  25                  30
```

<210> SEQ ID NO 39
<211> LENGTH: 21
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 39

Cys His His His His Arg Arg Arg Arg Arg Arg Arg Arg His
1               5                   10                  15

His His His His Cys
            20

<210> SEQ ID NO 40
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Leu Ile Lys Lys Ala Leu Ala Ala Leu Ala Lys Leu Asn Ile Lys
1               5                   10                  15

Leu Leu Tyr Gly Ala Ser Asn Leu Thr Trp Gly
            20                  25

<210> SEQ ID NO 41
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Leu Trp Arg Ala Leu Trp Arg Leu Leu Arg Ser Leu Trp Arg Leu
1               5                   10                  15

Leu Trp Arg Ala
            20

<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Leu Leu Arg Leu Leu Leu Arg Leu Trp Arg Arg Leu Leu Arg Leu
1               5                   10                  15

Leu Arg

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Leu Trp Arg Leu Leu Trp Arg Leu Trp Arg Arg Leu Trp Arg Leu
1               5                   10                  15

Leu Arg
```

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Leu Lys Leu Leu Lys Lys Leu Leu Lys Leu Leu Lys Lys Leu Leu
1               5                   10                  15

Lys Leu Leu

<210> SEQ ID NO 45
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Ala Leu Lys Leu Lys Leu Ala Leu Ala Leu Leu Ala Lys Leu Lys
1               5                   10                  15

Leu Ala

<210> SEQ ID NO 46
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gly Gly Gly Ala Arg Lys Lys Ala Ala Lys Ala Ala Arg Lys Lys Ala
1               5                   10                  15

Ala Lys Ala Ala Arg Lys Lys Ala Ala Lys Ala Ala Arg Lys Lys Ala
                20                  25                  30

Ala Lys Ala
        35

<210> SEQ ID NO 47
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Cys His His His His His Arg Lys Lys Arg Arg Gln Arg Arg Arg Arg
1               5                   10                  15

His His His His His Cys
                20

<210> SEQ ID NO 48
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

-continued

```
Cys His His His His His Arg Arg Arg Arg Arg Arg Arg Arg His
1               5                   10                  15
His His His His Cys
            20

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Phe Phe Leu Ile Pro Lys Gly Arg Arg Arg Arg Arg Arg Arg Gly
1               5                   10                  15
Cys

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Phe Phe Leu Ile Pro Lys Gly Arg Arg Arg Arg Arg Arg Arg Arg
1               5                   10                  15

<210> SEQ ID NO 51
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Trp Glu Ala Ala Leu Ala Glu Ala Leu Ala Glu Ala Leu Ala Glu His
1               5                   10                  15
Leu Ala Glu Ala Leu Ala Glu Ala Leu Glu Ala Leu Ala Ala
            20                  25                  30
```